United States Patent
Grosveld et al.

(10) Patent No.: US 9,803,016 B2
(45) Date of Patent: Oct. 31, 2017

(54) ANTI-CD47 ANTIBODIES AND METHODS OF USE

(71) Applicant: Erasmus University Medical Center, Rotterdam (NL)

(72) Inventors: Frank Grosveld, Rotterdam (NL); Scott Chappel, Milton, MA (US); Jonathan Hill, Salem, MA (US); Pamela M. Holland, Belmont, MA (US); Andrew Lake, Westwood, MA (US); Alison Paterson, Dedham, MA (US)

(73) Assignees: Erasmus University Medical Center, Rotterdam (NL); Surface Oncology, Inc., Cambridge, MA (US)

(*) Notice: Subject to any disclaimer, the term of this patent is extended or adjusted under 35 U.S.C. 154(b) by 0 days.

(21) Appl. No.: 15/473,206

(22) Filed: Mar. 29, 2017

(65) Prior Publication Data

US 2017/0204181 A1 Jul. 20, 2017

Related U.S. Application Data

(62) Division of application No. 15/271,861, filed on Sep. 21, 2016.

(60) Provisional application No. 62/371,047, filed on Aug. 4, 2016, provisional application No. 62/221,446, filed on Sep. 21, 2015.

(51) Int. Cl.
*A61K 39/395* (2006.01)
*C07K 16/28* (2006.01)
*A61K 39/00* (2006.01)

(52) U.S. Cl.
CPC ...... *C07K 16/2803* (2013.01); *C07K 16/2887* (2013.01); *A61K 2039/505* (2013.01); *C07K 2317/24* (2013.01); *C07K 2317/33* (2013.01); *C07K 2317/52* (2013.01); *C07K 2317/56* (2013.01); *C07K 2317/565* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| 5,057,604 A | 10/1991 | Brown |
| 5,624,821 A | 4/1997 | Winter et al. |
| 5,648,260 A | 7/1997 | Winter et al. |
| 7,514,229 B2 | 4/2009 | Jamieson et al. |
| 7,696,325 B2 | 4/2010 | Fukushima et al. |
| 8,562,997 B2 | 10/2013 | Jaiswal et al. |
| 8,758,750 B2 | 6/2014 | Weissman et al. |
| 9,017,675 B2 | 4/2015 | Liu et al. |
| 9,045,541 B2 | 6/2015 | Eckelman et al. |
| 9,352,037 B2 | 5/2016 | van den Berg |
| 2003/0026803 A1 | 2/2003 | Barclay |
| 2003/0108546 A1 | 6/2003 | Fukushima et al. |
| 2004/0213792 A1 | 10/2004 | Clemmons et al. |
| 2005/0118164 A1 | 6/2005 | Herman |
| 2006/0239910 A1 | 10/2006 | Nicolaides et al. |
| 2007/0113297 A1 | 5/2007 | Yang et al. |
| 2014/0363442 A1 | 12/2014 | Frazier et al. |
| 2014/0369924 A1 | 12/2014 | Weissman et al. |

FOREIGN PATENT DOCUMENTS

| EP | 0388151 A1 | 9/1990 |
| EP | 1693385 A1 | 8/2006 |
| EP | 2111869 A1 | 10/2009 |
| EP | 2242512 A1 | 10/2010 |
| EP | 2995315 A1 | 3/2016 |
| WO | WO-9940940 A1 | 8/1999 |
| WO | WO-2009131453 A1 | 10/2009 |
| WO | WO-2013119714 A1 | 8/2013 |
| WO | WO-2014/121093 A1 | 8/2014 |
| WO | WO-2014123580 A1 | 8/2014 |
| WO | WO-2014149477 A1 | 9/2014 |
| WO | WO-2014179132 A1 | 11/2014 |
| WO | WO-2014186761 A2 | 11/2014 |
| WO | WO-2015041987 A1 | 3/2015 |

OTHER PUBLICATIONS

Alegre et al. (1992) "Effect of a single amino acid mutation on the activating and immunosuppressive properties of a 'humanized' OKT3 monoclonal antibody," J. Immunol., 148: 3461-3468.

Armour et al. (1999) "Recombinant human IgG molecules lacking Fcgamma receptor I binding and monocyte triggering activities," Eur. J. Immunol., 29(8): 2613-24.

Avent et al. (1988) "Monoclonal antibodies that recognize different membrane proteins that are deficient in Rhnull human erythrocytes. One group of antibodies reacts with a variety of cells and tissues whereas the other group is erythroid-specific," Biochem. J., 251: 499-505.

Boerman et al. (1989) "Monoclonal antibodies against ovarian carcinoma-associated antigens, raised by immunization with cyst fluids," Anticancer Res., 9(3): 551-8.

Brooke et al. (2004) "Human lymphocytes interact directly with CD47 through a novel member of the signal regulatory protein (SIRP) family," J Immunol., 173(4): 2562-70.

Bullinger et al. (2008) "An FLT3 gene-expression signature predicts clinical outcome in normal karyotype AML," Blood, vol. 111, pp. 4490-4495.

Carter (2001) "Bispecific human IgG by design," J. Immunol. Methods, 248: 7-15.

Chao et al. (2010) "Anti-CD47 antibody synergizes with rituximab to promote phagocytosis and eradicate non-Hodgkin lymphoma," Cell, 42(5): 699-713.

(Continued)

*Primary Examiner* — Sheela J Huff
(74) *Attorney, Agent, or Firm* — Nelson Mullins Riley & Scarborough LLP; Amy E. Mandragouras, Esq.; Ariana D. Harris

(57) ABSTRACT

Disclosed herein are anti-CD47 antibody molecules, their manufacture and use in treating disorders associated with CD47 expression, for example, certain hematological cancers and solid tumors.

30 Claims, 21 Drawing Sheets

(56) References Cited

OTHER PUBLICATIONS

Chao et al. (2010) "Calreticulin is the dominant pro-phagocytic signal on multiple human cancers and is counterbalanced by CD47," Sci Transl Med. 2(63):63ra94.

Chao et al. (2011) "Therapeutic antibody targeting of CD47 eliminates human acute lymphoblastic leukemia," Cancer Res., 71(4): 1374-84.

Dall'Acqua et al.(2006) "Properties of human IgG1s engineered for enhanced binding to the neonatal Fc receptor (FcRn)," J. Biol. Chem., 281(33): 23514-23524.

De Oliveira et al. (2012) "Integrin-associated protein (CD47) is a putative mediator for soluble fibrinogen interaction with human red blood cells membrane," Biochim Biophys Acta, 1818(3):481-90.

Edris et al.(2012) "Antibody therapy targeting the CD47 protein is effective in a model of aggressive metastatic leiomyosarcoma," Proc. Natl. Acad. Sci. USA, 109(17):6656-61.

Fadeel et al. (2004) "Buried alive: a novel approach to cancer treatment," FASEB J., 18(1): 1-4.

Frazier et al. (2010) "CD47," UCSD Nature Molecule Pages.

Ho et al. (2015) "'Velcro' Engineering of High Affinity CD47 Ectodomain as Signal Regulatory Protein α (SIRPα) Antagonists That Enhance Antibody-dependent Cellular Phagocytosis," J Biol. Chem., 290(20): 12650-12663.

Idusogie et al. (2001) "Engineered antibodies with increased activity to recruit complement," J. Immunol., 166(4): 2571-5.

International Search Report and Written Opinion for International Patent Application No. PCT/US2016/052878, mailed on Dec. 12, 2016 (14 pages).

Jaiswal et al. (2009) "CD47 is upregulated on circulating hematopoietic stem cells and leukemia cells to avoid phagocytosis," Cell, 138(2):271-85.

Jaiswal et al. (2010) "Macrophages as mediators of tumor immunosurveillance," Trends Immunol., 31(6):212-9.

Jamieson (2007) "Cancer stem cell targeted therapy: Removing the sword of Damocles," Cancer Res., AACR Annual Meeting, Abstract SY26-01.

Jamieson et al. (2005) "Increased Expression of CD47 is a Constant Marker in Mouse and Human Myeloid Leukemias," Blood, 106(11): 3260 (Leukemias: Cyogenetics and Molecular Markers in Diagnosis and Prognosis III, 911a, Poster Board #-Session: 511-111).

Kikuchi et al. (2004) "A bivalent single-chain Fv fragment against CD47 induces apoptosis for leukemic cells," Biochem. Biophys. Res. Commun., 315(4): 912-8.

Kojima et al. (2016) "CD47-blocking antibodies restore phagocytosis and prevent atherosclerosis," Nature, 536(7614):86-90 and including 15 pagees of Supplemental Data.

Latour et al. (2011) "Bidirectional negative regulation of human T and dendritic cells by CD47 and its cognate receptor signal-regulator protein-alpha: down-regulation of IL-12 responsiveness and inhibition of dendritic cell activation," J Immunol., 167(5):2547-54.

Lazar et al.(2006) "Engineered antibody Fc variants with enhanced effector function," Proc. Natl. Acad. Sci. USA, 103(11): 4005-4010.

Liu et al. (2002) "Signal regulatory protein (SIRPalpha), a cellular ligand for CD47, regulates neutrophil transmigration," J. Biol. Chem., 277(12):10028-36.

Liu et al. (2015) "Pre-Clinical Development of a Humanized Anti-CD47 Antibody with Anti-Cancer Therapeutic Potential," PLoS One, 10(9):e0137345.

Majeti et al, (2009) "CD47 is an adverse prognostic factor and therapeutic antibody target on human acute myeloid leukemia stem cells," Cell.138(2): 286-99.

Majeti et al. (2008) "CD47 is an Independent Prognostic Factor and Therapeutic Antibody Target on Human Acute Myeloid Leukemia Stem Cells," Blood, 112(11): 766 (2008 Ash Annual Meeting Abstracts, vol. 112, Issue 11, Nov. 16, 2008).

Manna et al. (2003) "The mechanism of CD47-dependent killing of T cells: heterotrimeric Gi-dependent inhibition of protein kinase A," J. Immunol., 170(7): 3544-53.

Manna et al. (2004) "CD47 mediates killing of breast tumor cells via Gi-dependent inhibition of protein kinase A," Cancer Res., 64(3): 1026-36.

Mateo et al. (1999) "CD47 ligation induces caspase-independent cell death in chronic lymphocytic leukemia," Nature Med., 5(11): 1277-84.

Mateo et al. (2002) "Mechanisms of CD47-induced caspase-independent cell death in normal and leukemic cells: link between phosphatidylserine exposure and cytoskeleton organization," Blood, 100(8):2882-90.

Moore et al. (2010) "Engineered Fc variant antibodies with enhanced ability to recruit complement and mediate effector functions," MABS, 2(2): 181-189.

Natsume et al. (2008) "Engineered antibodies of IgG1/IgG3 mixed isotype with enhanced cytotoxic activities," Cancer Res. 68(10): 3863-72.

Ngo et al. (2016) "Antibody Therapy Targeting CD47 and CD271 Effectively Suppresses Melanoma Metastasis in Patient-Derived Xenografts," Cell Rep., 16(6):1701-16.

Okazawa et al. (2005) "Negative Regulation of Phagocytosis in Macrophages by the CD47-SHPS-1 System," J. Immunol., 174: 2004-11.

Oldenborg et al. (2000) "Role of CD47 as a marker of self on red blood cells," Science, 288(5473): 2051-4.

Oldenborg et al. (2001) "CD47-signal regulatory protein alpha (SIRPalpha) regulates Fcgamma and complement receptor-mediated phagocytosis," J. Exp. Med., 193(7): 855-62.

Overdijk et al. (2015) "Antibody-mediated phagocytosdis contributes to the anti-tumor activity of the therapeutic antibody daratumumab in lymphoma and multiple myeloma," mAbs, 7(2):311-320.

Petrova et al. (2016) "TTI-621 (SIRPαFc): A CD47-Blocking Innate Immune Checkpoint Inhibitor With Broad Anti-Tumor Activity and Minimal Erythrocyte Binding," Clin. Cancer Res., Epub ahead of print.

Pettersen et al. (1999) "CD47 signals T cell death," J Immunol., 162(12): 7031-40.

Reya et al. (2001) "Stem cells, cancer, and cancer stem cells," Nature, 414(6859): 105-11.

Sagawa et al.(2011) "A new disulfide-linked dimer of a single-chain antibody fragment against human CD47 induces apoptosis in lymphoid malignant cells via the hypoxia inducible factor-1α pathway," Cancer Sci., 102(6):1208-15.

Seiffert et al. (1999) "Human signal-regulatory protein is expressed on normal, but not on subsets of leukemic myeloid cells and mediates cellular adhesion involving its counterreceptor CD47," Blood, 94(11): 3633-43.

Shields et al. (2001) "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276(9): 6591-6604.

Stavenhagen et al. (2007) "Fc optimization of therapeutic antibodies enhances their ability to kill tumor cells in vitro and controls tumor expansion in vivo via low-affinity activating Fcgamma receptors," Cancer Res., 67(18): 8882-8890.

Stavenhagen et al. (2008) "Enhancing the potency of therapeutic monoclonal antibodies via Fc optimization," Advan. Enzyme Regul., 48: 152-164.

Subramanian et al. (2006) "Species- and cell type-specific interactions between CD47 and human SIRPalpha," Blood, 107(6): 2548-56.

Tabas et al. (2016) "Heart disease: Death-defying plaque cells," Nature, 536(7614):32-3.

Tada et al. (2003) "Tethering of Apoptotic Cells to Phagocytes through Binding of CD47 to Src Homology 2 Domain-Bearing Protein Tyrosine Phosphatase Substrate-1," J. Immunol., 171: 5718-26.

Tazzari et al. (2007) "The insulin-like growth factor-I receptor kinase inhibitor NVP-AEW541 induces apoptosis in acute myeloid leukemia cells exhibiting autocrine insulin-like growth factor-I secretion," Leukemia, 21(5): 886-96.

(56) References Cited

OTHER PUBLICATIONS

Tseng et al. (2013) "Anti-CD47 antibody-mediated phagocytosis of cancer by macrophages primes an effective antitumor T-cell response," Proc. Natl. Acad. Sci. USA, 110(27):11103-8.

Uno et al. (2007) "Antitumor Activity of a Monoclonal Antibody Against CD47 in Xenograft Models of Human Leukemia," Onc. Rep., 17: 1189-94.

van Beek et al. (2005) "Signal regulatory proteins in the immune system," J. Immunol., 175(12): 7781-7.

Vernon-Wilson et al. (2000) "CD47 is a ligand for rat macrophage membrane signal regulatory protein SIRP (OX41) and human SIRPalpha 1," Eur. J. Immunol., 30(8): 2130-7.

Wang et al. (2007) "Attenuation of phagocytosis of xenogeneic cells by manipulating CD47," Blood, 109(2): 836-42.

Ward et al. (1989) "Binding activities of a repertoire of single immunoglobulin variable domains secreted from *Escherichia coli*," Nature, 341: 544-546.

Weiskopf et al. (2013) "Engineered SIRPα variants as immunotherapeutic adjuvants to anticancer antibodies," Science, 341(6141): 88-91.

Weiskopf et al. (2015) "CD47-blocking therapies stimulate macrophage cytokine secretion and are effective in a model of peritoneal carcinomatosis," J. Immunother. Cancer., 3(Suppl 2): P248.

Weiskopf et al. (2016) "CD47-blocking immunotherapies stimulate macrophage-mediated destruction of small-cell lung cancer," J. Clin. Investigation 126(7): 2610-2620.

Willingham et al. (2012) "The CD47-signal regulatory protein alpha (SIRPa) interaction is a therapeutic target for human solid tumors," Proc. Natl. Acad. Sci. USA, 109(17):6662-7.

Zalevsky et al. (2010) "Enhanced antibody half-life improves in vivo activity," Nature Biotech., 28(2): 157-159.

Zeng et al. (2016) "A fully human anti-CD47 blocking antibody with therapeutic potential for cancer," Oncotarget, vol. 7, pp. 83040-83050.

Zhao et al (2012) "Is targeting of CD47-SIRPα enough for treating hematopoietic malignancy?" Blood, 119(18):4333-4.

Zhao et al. (2011) "CD47-signal regulatory protein-α (SIRPα) interactions form a barrier for antibody-mediated tumor cell destruction," Proc. Natl. Acad. Sci. USA, 108(45)18342-7.

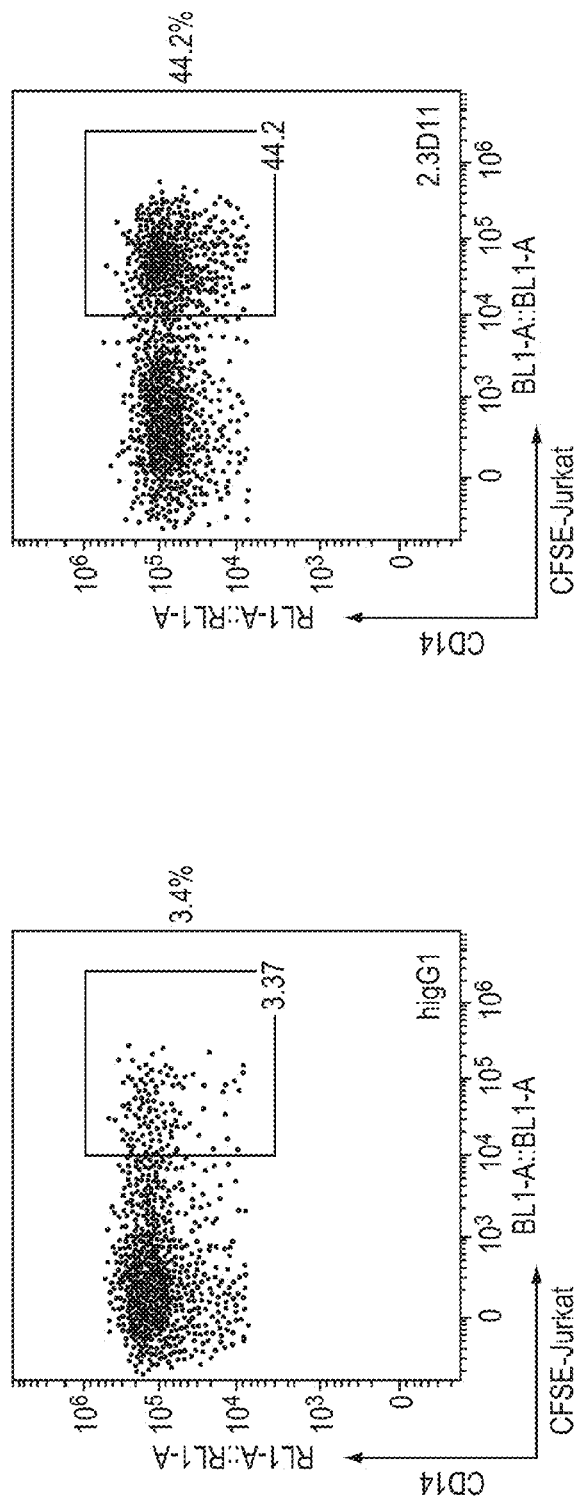
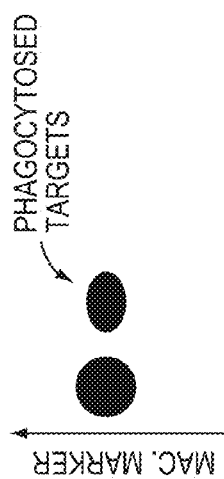

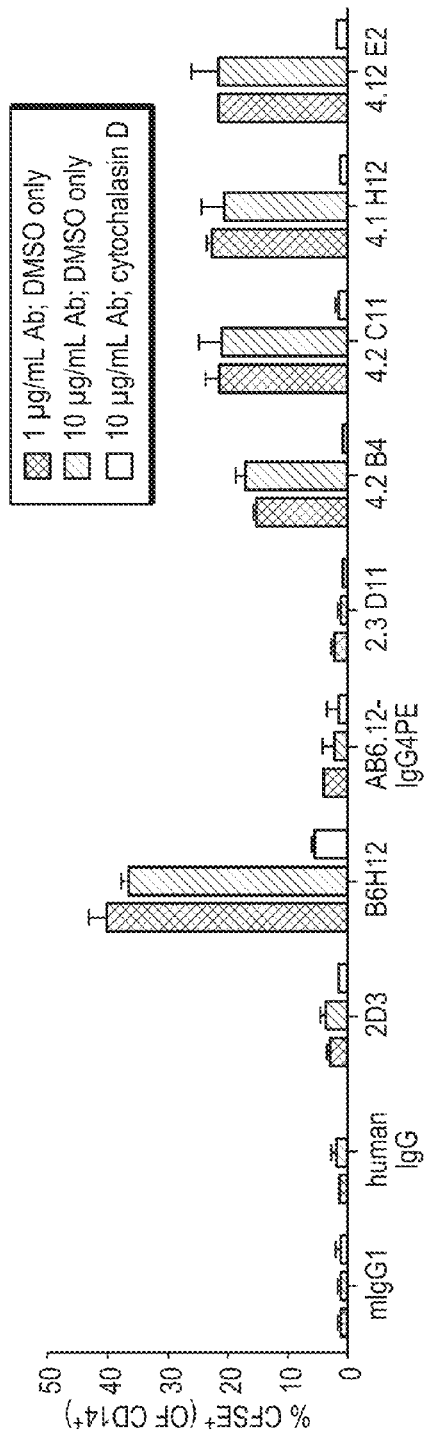
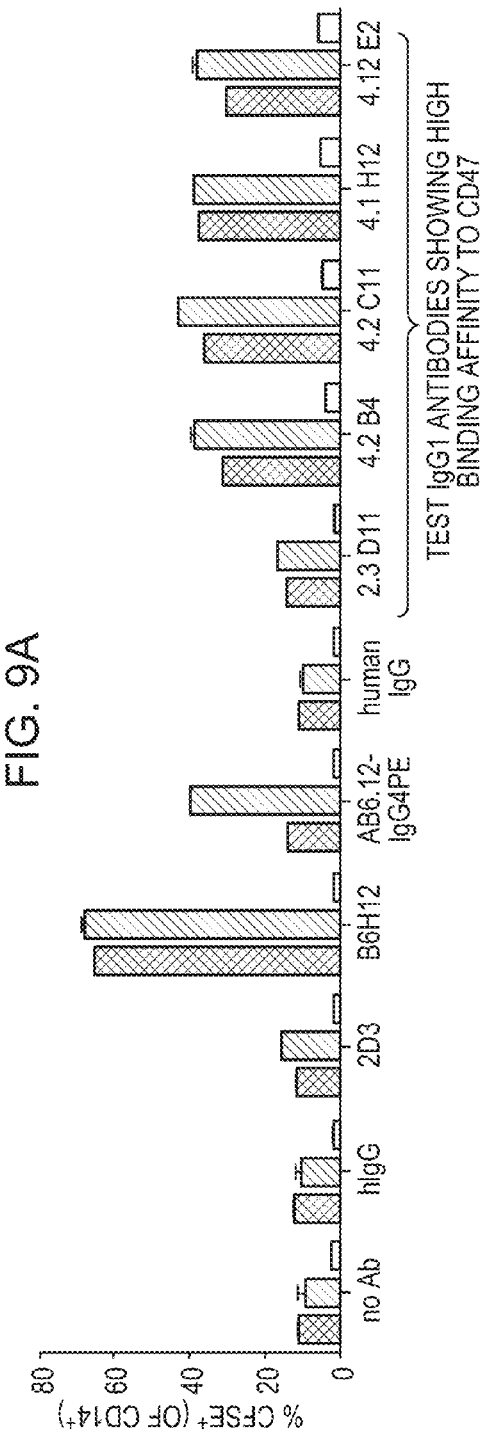
FIG. 9A
FIG. 9B

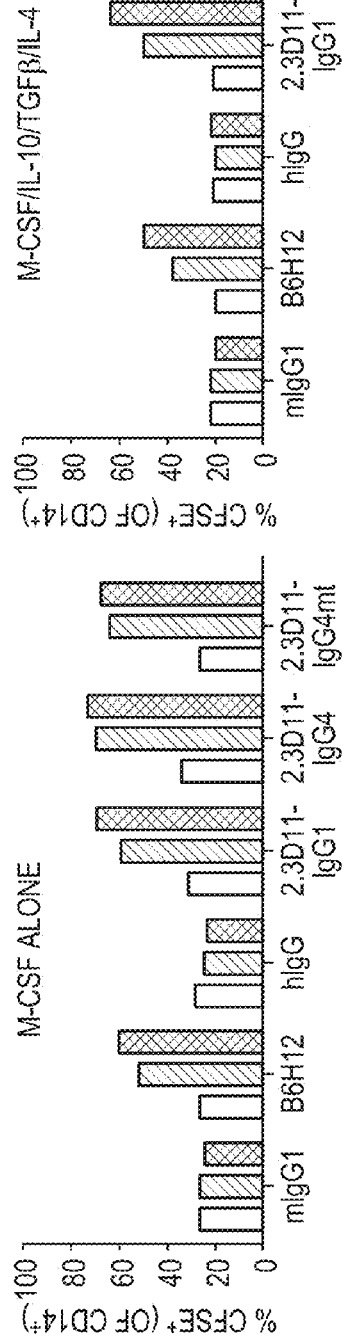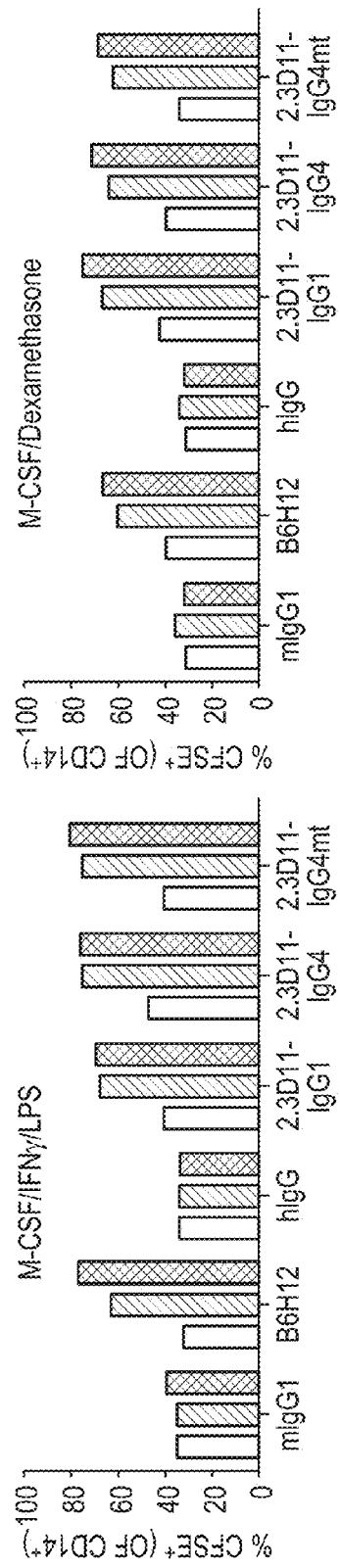
FIG. 12A  M-CSF ALONE
FIG. 12B  M-CSF/IL-10/TGFβ/IL-4
FIG. 12C  M-CSF/IFNγ/LPS
FIG. 12D  M-CSF/Dexamethasone

SEQUENCE LISTING

```
<160> NUMBER OF SEQ ID NOS: 38

<210> SEQ ID NO 1
<211> LENGTH: 323
<212> TYPE: PRT
<213> ORGANISM: Homo sapiens

<400> SEQUENCE: 1

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45
```

Gln Asn Thr Thr Glu Val Tyr Val Lys Trp Lys Phe Lys Gly Arg Asp
            50                  55                  60
Ile Tyr Thr Phe Asp Gly Ala Leu Asn Lys Ser Thr Val Pro Thr Asp
 65                  70                  75                  80
Phe Ser Ser Ala Lys Ile Glu Val Ser Gln Leu Leu Lys Gly Asp Ala
                 85                  90                  95
Ser Leu Lys Met Asp Lys Ser Asp Ala Val Ser His Thr Gly Asn Tyr
            100                 105                 110
Thr Cys Glu Val Thr Glu Leu Thr Arg Glu Gly Glu Thr Ile Ile Glu
        115                 120                 125
Leu Lys Tyr Arg Val Val Ser Trp Phe Ser Pro Asn Glu Asn Ile Leu
130                 135                 140
Ile Val Ile Phe Pro Ile Phe Ala Ile Leu Leu Phe Trp Gly Gln Phe
145                 150                 155                 160
Gly Ile Lys Thr Leu Lys Tyr Arg Ser Gly Gly Met Asp Glu Lys Thr
                165                 170                 175
Ile Ala Leu Leu Val Ala Gly Leu Val Ile Thr Val Ile Val Ile Val
            180                 185                 190
Gly Ala Ile Leu Phe Val Pro Gly Glu Tyr Ser Leu Lys Asn Ala Thr
        195                 200                 205
Gly Leu Gly Leu Ile Val Thr Ser Thr Gly Ile Leu Ile Leu Leu His
    210                 215                 220
Tyr Tyr Val Phe Ser Thr Ala Ile Gly Leu Thr Ser Phe Val Ile Ala
225                 230                 235                 240
Ile Leu Val Ile Gln Val Ala Tyr Ile Leu Ala Val Val Gly Leu
                245                 250                 255
Ser Leu Cys Ile Ala Ala Cys Ile Pro Met His Gly Pro Leu Leu Ile
            260                 265                 270
Ser Gly Leu Ser Ile Leu Ala Leu Ala Gln Leu Leu Gly Leu Val Tyr
        275                 280                 285
Met Lys Phe Val Ala Ser Asn Gln Lys Thr Ile Gln Pro Pro Arg Lys
290                 295                 300
Ala Val Glu Glu Pro Leu Asn Ala Phe Lys Glu Ser Lys Gly Met Met
305                 310                 315                 320
Asn Asp Glu

<210> SEQ ID NO 2
<211> LENGTH: 5346
<212> TYPE: DNA
<213> ORGANISM: Homo sapiens

<400> SEQUENCE: 2

| | | | | | |
|---|---|---|---|---|---|
| ggggagcagg | cggggagcg | ggcgggaagc | agtgggagcg | cgcgtgcgcg | cggccgtgca | 60 |
| gcctgggcag | tgggtcctgc | ctgtgacgcg | cggcggcggt | cggtcctgcc | tgtaacggcg | 120 |
| gcggcggctg | ctgctccaga | cacctgcggc | ggcggcggca | accccgcggc | gggcgcggag | 180 |
| atgtggcccc | tggtagcggc | gctgttgctg | ggctcggcgt | gctgcggatc | agctcagcta | 240 |
| ctatttaata | aaacaaaatc | tgtagaattc | acgttttgta | atgacactgt | cgtcattcca | 300 |
| tgctttgtta | ctaatatgga | ggcacaaaac | actactgaag | tatacgtaaa | gtggaaattt | 360 |
| aaaggaagag | atatttacac | ctttgatgga | gctctaaaca | agtccactgt | ccccactgac | 420 |
| tttagtagtg | caaaaattga | agtctcacaa | ttactaaaag | gagatgcctc | tttgaagatg | 480 |
| gataagagtg | atgctgtctc | acacacagga | aactacactt | gtgaagtaac | agaattaacc | 540 |

-continued

```
agagaaggtg aaacgatcat cgagctaaaa tatcgtgttg tttcatggtt ttctccaaat      600
gaaatattc  ttattgttat tttcccaatt tttgctatac tcctgttctg gggacagttt      660
ggtattaaaa cacttaaata tagatccggt ggtatggatg agaaaacaat tgctttactt     720
gttgctggac tagtgatcac tgtcattgtc attgttggag ccattctttt cgtcccaggt     780
gaatattcat aaagaatgc  tactggcctt ggtttaattg tgacttctac agggatatta     840
atattacttc actactatgt gtttagtaca gcgattggat taacctcctt cgtcattgcc     900
atattggtta ttcaggtgat agcctatatc ctcgctgtgg ttggactgag tctctgtatt     960
gcggcgtgta taccaatgca tggccctctt ctgatttcag gtttgagtat cttagctcta    1020
gcacaattac ttggactagt ttatatgaaa tttgtggctt ccaatcagaa gactatacaa    1080
cctcctagga aagctgtaga ggaaccccctt aatgcattca aagaatcaaa aggaatgatg   1140
aatgatgaat aactgaagtg aagtgatgga ctccgatttg gagagtagta agacgtgaaa    1200
ggaatacact tgtgtttaag caccatggcc ttgatgattc actgttgggg agaagaaaca   1260
agaaaagtaa ctggttgtca cctatgagac ccttacgtga ttgttagtta agttttatt    1320
caaagcagct gtaatttagt taataaaata attatgatct atgttgtttg cccaattgag    1380
atccagtttt tgttgttat ttttaatcaa ttaggggcaa tagtagaatg gacaatttcc     1440
aagaatgatg cctttcaggt cctagggcct ctggcctcta ggtaaccagt ttaaattggt    1500
tcagggtgat aactacttag cactgccctg gtgattaccc agagatatct atgaaaacca   1560
gtggcttcca tcaaaccttt gccaactcag gttcacagca gctttgggca gttatggcag   1620
tatggcatta gctgagaggt gtctgccact tctgggtcaa tggaataata aattaagtac   1680
aggcaggaat ttggttggga gcatcttgta tgatctccgt atgatgtgat attgatggag   1740
atagtggtcc tcattcttgg gggttgccat tcccacattc cccttcaac  aaacagtgta    1800
acaggtcctt cccagattta gggtactttt attgatggat atgttttcct tttattcaca    1860
taaccccttg aaaccctgtc ttgtcctcct gttacttgct tctgctgtac aagatgtagc    1920
acctttctc  ctctttgaac atggtctagt gacacggtag caccagttgc aggaaggagc    1980
cagacttgtt ctcagagcac tgtgttcaca cttttcagca aaaatagcta tggttgtaac   2040
atatgtattc ccttcctctg atttgaaggc aaaaatctac agtgtttctt cacttctttt    2100
ctgatctggg gcatgaaaaa agcaagattg aaatttgaac tatgagtctc ctgcatggca    2160
acaaaatgtg tgtcaccatc aggccaacag gccagccctt gaatgggat  ttattactgt    2220
tgtatctatg ttgcatgata acattcatc  accttcctcc tgtagtcctg cctcgtactc    2280
cccttcccct atgattgaaa agtaaacaaa acccacattt cctatcctgg ttagaagaaa    2340
attaatgttc tgacagttgt gatcgcctgg agtactttta gacttttagc attcgttttt    2400
tacctgtttg tggatgtgtg tttgtatgtg catacgtatg agataggcac atgcatcttc    2460
tgtatggaca aaggtggggt acctacagga gagcaaggt  taattttgtg cttttagtaa   2520
aaacatttaa atacaaagtt ctttattggg tggaattata tttgatgcaa atatttgatc   2580
acttaaaact tttaaaactt ctaggtaatt tgccacgctt tttgactgct caccaatacc    2640
ctgtaaaaat acgtaattct tcctgttgt  gtaataagat attcatattt gtagttcat    2700
taataatagt tatttcttag tccatcagat gttcccgtgt gcctctttta tgccaaattg    2760
attgtcatat ttcatgttgg gaccaagtag tttgcccatg gcaaacctaa atttatgacc   2820
tgctgaggcc tctcagaaaa ctgagcatac tagcaagaca gctcttcttg aaaaaaaaaa   2880
```

```
tatgtataca caaatatata cgtatatcta tatatacgta tgtatataca cacatgtata    2940
ttcttccttg attgtgtagc tgtccaaaat aataacatat atagagggag ctgtattcct    3000
ttatacaaat ctgatggctc ctgcagcact ttttccttct gaaaatattt acattttgct    3060
aacctagttt gttactttaa aaatcagttt tgatgaaagg agggaaaagc agatggactt    3120
gaaaagatc caagctccta ttagaaaagg tatgaaaatc tttatagtaa aattttttat    3180
aaactaaagt tgtaccttt aatatgtagt aaactctcat ttatttgggg ttcgctcttg    3240
gatctcatcc atccattgtg ttctctttaa tgctgcctgc cttttgaggc attcactgcc    3300
ctagacaatg ccaccagaga tagtggggga atgccagat gaaaccaact cttgctctca    3360
ctagttgtca gcttctctgg ataagtgacc acagaagcag gagtcctcct gcttgggcat    3420
cattgggcca gttccttctc tttaaatcag atttgtaatg ctcccaaat tccatcacat    3480
cacatttaaa ttgcagacag tgttttgcac atcatgtatc tgttttgtcc cataatatgc    3540
tttttactcc ctgatcccag tttctgctgt tgactcttcc attcagtttt atttattgtg    3600
tgttctcaca gtgacaccat tgtcctttt ctgcaacaac ctttccagct acttttgcca    3660
aattctattt gtcttctcct tcaaaacatt ctcctttgca gttcctcttc atctgtgtag    3720
ctgctctttt gtctcttaac ttaccattcc tatagtactt tatgcatctc tgcttagttc    3780
tattagtttt ttggccttgc tcttctcctt gattttaaaa ttccttctat agctagagct    3840
tttctttctt tcattctctc ttcctgcagt gttttgcata catcagaagc taggtacata    3900
agttaaatga ttgagagttg gctgtattta gatttatcac ttttaatag ggtgagcttg    3960
agagtttct ttctttctgt ttttttttt tgttttttt ttttttttt ttttttttt    4020
ttttgactaa tttcacatgc tctaaaaacc ttcaaggtg attatttttc tcctggaaac    4080
tccaggtcca ttctgtttaa atccctaaga atgtcagaat taaataaca gggctatccc    4140
gtaattggaa atatttcttt tttcaggatg ctatagtcaa tttagtaagt gaccaccaaa    4200
ttgttatttg cactaacaaa gctcaaaaca cgataagttt actcctccat ctcagtaata    4260
aaaattaagc tgtaatcaac cttctaggtt tctcttgtct aaaatgggt attcaaaaat    4320
ggggatctgt ggtgtatgta tggaaacaca tactccttaa tttacctgtt gttggaaact    4380
ggagaaatga ttgtcgggca accgtttatt ttttattgta ttttatttgg ttgagggatt    4440
tttttataaa cagtttact tgtgtcatat tttaaaatta ctaactgcca tcacctgctg    4500
gggtcctttg ttaggtcatt ttcagtgact aatagggata atccaggtaa ctttgaagag    4560
atgagcagtg agtgaccagg cagttttct gcctttagct ttgacagttc ttaattaaga    4620
tcattgaaga ccagctttct cataaatttc tctttttgaa aaaagaaag catttgtact    4680
aagctcctct gtaagacaac atcttaaatc ttaaaagtgt tgttatcatg actggtgaga    4740
gaagaaaaca ttttgttttt attaaatgga gcattattta caaaaagcca ttgttgagaa    4800
ttagatccca catcgtataa atatctatta accattctaa ataaagagaa ctccagtgtt    4860
gctatgtgca agatcctctc ttggagcttt tttgcatagc aattaaaggt gtgctatttg    4920
tcagtagcca ttttttttgca gtgatttgaa gaccaaagtt gttttacagc tgtgttaccg    4980
ttaaaggttt ttttttttat atgtattaaa tcaattatc actgtttaaa gctttgaata    5040
tctgcaatct ttgccaaggt acttttttat ttaaaaaaaa acataacttt gtaaatatta    5100
ccctgtaata ttatatatac ttaataaaac attttaagct attttgttgg gctatttcta    5160
ttgctgctac agcagaccac aagcacattt ctgaaaaatt taatttatta atgtattttt    5220
aagttgctta tattctaggt aacaatgtaa agaatgattt aaaatattaa ttatgaattt    5280
```

```
tttgagtata ataccaata agcttttaat tagagcagag ttttaattaa aagttttaaa    5340
tcagtc                                                              5346
```

<210> SEQ ID NO 3
<211> LENGTH: 144
<212> TYPE: PRT
<213> ORGANISM: Artificial Sequence
<220> FEATURE:
<223> OTHER INFORMATION: 2.3D11 Heavy Chain Variable Region (With
      Leader Sequence)

<400> SEQUENCE: 3

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gly Thr Leu Ser Leu Thr Cys Ala Val Ser Gly Val Ser Ile
        35                  40                  45

Arg Ser Ile Asn Trp Trp Asn Trp Val Arg Gln Pro Pro Gly Lys Gly
    50                  55                  60

Leu Glu Trp Ile Gly Glu Ile Tyr His Ser Gly Ser Thr Asn Tyr Asn
65                  70                  75                  80

Pro Ser Leu Lys Ser Arg Val Thr Ile Ser Val Asp Lys Ser Lys Asn
                85                  90                  95

Gln Phe Ser Leu Lys Leu Asn Ser Val Thr Ala Ala Asp Thr Ala Val
            100                 105                 110

Tyr Tyr Cys Ala Arg Asp Gly Gly Ile Ala Val Thr Asp Tyr Tyr Tyr
        115                 120                 125

Tyr Gly Leu Asp Val Trp Gly Gln Gly Thr Thr Val Thr Val Ser Ser
    130                 135                 140
```

<210> SEQ ID NO 4
<211> LENGTH: 125
<212> TYPE: PRT
<213> ORGANISM: Artificial Sequence
<220> FEATURE:
<223> OTHER INFORMATION: 2.3D11 Light Chain Variable Region (With Leader
      Sequence)

<400> SEQUENCE: 4

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Val Ser Ile Arg Ser Ile
            20                  25                  30

Asn Trp Trp Asn Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Asn Ser Val Thr Ala Ala Asp Thr Ala Val Tyr Tyr Cys
                85                  90                  95

Ala Arg Asp Gly Gly Ile Ala Val Thr Asp Tyr Tyr Tyr Tyr Gly Leu
            100                 105                 110

Asp Val Trp Gly Gln Gly Thr Thr Val Thr Val Ser Ser
    115                 120                 125
```

```
<210> SEQ ID NO 5
<211> LENGTH: 126
<212> TYPE: PRT
<213> ORGANISM: Artificial Sequence
<220> FEATURE:
<223> OTHER INFORMATION: 2.3D11 Light Chain Variable Region (With
      Leader Sequence)

<400> SEQUENCE: 5

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Ser
        35                  40                  45

Val Ser Ser Asn Leu Ala Trp Tyr Gln Gln Lys Pro Gly Gln Ala Pro
    50                  55                  60

Arg Leu Leu Ile Tyr Gly Ala Phe Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asp Trp Phe Thr Phe Gly Gly Gly Thr Lys Val Glu Ile Lys
        115                 120                 125

<210> SEQ ID NO 6
<211> LENGTH: 106
<212> TYPE: PRT
<213> ORGANISM: Artificial Sequence
<220> FEATURE:
<223> OTHER INFORMATION: 2.3D11 Light Chain Variable Region (Without
      Leader Sequence)

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Phe Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Phe Thr
                85                  90                  95

Phe Gly Gly Gly Thr Lys Val Glu Ile Lys
            100                 105

<210> SEQ ID NO 7
<211> LENGTH: 6
<212> TYPE: PRT
<213> ORGANISM: Artificial Sequence
<220> FEATURE:
<223> OTHER INFORMATION: 2.3D11 Heavy Chain CDR1

<400> SEQUENCE: 7

Ser Ile Asn Trp Trp Asn
1               5
```

<210> SEQ ID NO 8
<211> LENGTH: 16
<212> TYPE: PRT
<213> ORGANISM: Artificial Sequence
<220> FEATURE:
<223> OTHER INFORMATION: 2.3D11 Heavy Chain CDR2

<400> SEQUENCE: 8

Glu Ile Tyr His Ser Gly Ser Thr Asn Tyr Asn Pro Ser Leu Lys Ser
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: 2.3D11 Heavy Chain CDR3

<400> SEQUENCE: 9

Asp Gly Gly Ile Ala Val Thr Asp Tyr Tyr Tyr Gly Leu Asp Val
1               5                   10                  15

<210> SEQ ID NO 10
<211> LENGTH: 11
<212> TYPE: PRT
<213> ORGANISM: Artificial Sequence
<220> FEATURE:
<223> OTHER INFORMATION: 2.3D11 Light Chain CDR1

<400> SEQUENCE: 10

Arg Ala Ser Glu Ser Val Ser Ser Asn Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: 2.3D11 Light Chain CDR2

<400> SEQUENCE: 11

Gly Ala Phe Asn Arg Ala Thr
1               5

<210> SEQ ID NO 12
<211> LENGTH: 8
<212> TYPE: PRT
<213> ORGANISM: Artificial Sequence
<220> FEATURE:
<223> OTHER INFORMATION: 2.3D11 Light Chain CDR3

<400> SEQUENCE: 12

Gln Gln Arg Ser Asp Trp Phe Thr
1               5

<210> SEQ ID NO 13
<211> LENGTH: 469
<212> TYPE: PRT
<213> ORGANISM: Artificial Sequence
<220> FEATURE:
<223> OTHER INFORMATION: 2.3D11 Heavy Chain (With Leader Sequence)

<400> SEQUENCE: 13

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys

```
                    20                  25                  30
Pro Ser Gly Thr Leu Ser Leu Thr Cys Ala Val Ser Gly Val Ser Ile
                35                  40                  45
Arg Ser Ile Asn Trp Trp Asn Trp Val Arg Gln Pro Pro Gly Lys Gly
            50                  55                  60
Leu Glu Trp Ile Gly Glu Ile Tyr His Ser Gly Ser Thr Asn Tyr Asn
 65                  70                  75                  80
Pro Ser Leu Lys Ser Arg Val Thr Ile Ser Val Asp Lys Ser Lys Asn
                85                  90                  95
Gln Phe Ser Leu Lys Leu Asn Ser Val Thr Ala Ala Asp Thr Ala Val
            100                 105                 110
Tyr Tyr Cys Ala Arg Asp Gly Gly Ile Ala Val Thr Asp Tyr Tyr Tyr
            115                 120                 125
Tyr Gly Leu Asp Val Trp Gly Gln Gly Thr Thr Val Thr Val Ser Ser
            130                 135                 140
Ala Glu Thr Thr Ala Pro Ser Val Tyr Pro Leu Ala Pro Gly Thr Ala
145                 150                 155                 160
Leu Lys Ser Asn Ser Met Val Thr Leu Gly Cys Leu Val Lys Gly Tyr
                165                 170                 175
Phe Pro Glu Pro Val Thr Val Thr Trp Asn Ser Gly Ala Leu Ser Ser
            180                 185                 190
Gly Val His Thr Phe Pro Ala Val Leu Gln Ser Gly Leu Tyr Thr Leu
            195                 200                 205
Thr Ser Ser Val Thr Val Pro Ser Ser Thr Trp Pro Ser Gln Thr Val
            210                 215                 220
Thr Cys Asn Val Ala His Pro Ala Ser Ser Thr Lys Val Asp Lys Lys
225                 230                 235                 240
Ile Val Pro Arg Asn Cys Gly Gly Asp Cys Lys Pro Cys Ile Cys Thr
                245                 250                 255
Gly Ser Glu Val Ser Ser Val Phe Ile Phe Pro Pro Lys Pro Lys Asp
            260                 265                 270
Val Leu Thr Ile Thr Leu Thr Pro Lys Val Thr Cys Val Val Val Asp
            275                 280                 285
Ile Ser Gln Asp Asp Pro Glu Val His Phe Ser Trp Phe Val Asp Asp
            290                 295                 300
Val Glu Val His Thr Ala Gln Thr Arg Pro Pro Glu Glu Gln Phe Asn
305                 310                 315                 320
Ser Thr Phe Arg Ser Val Ser Glu Leu Pro Ile Leu His Gln Asp Trp
                325                 330                 335
Leu Asn Gly Arg Thr Phe Arg Cys Lys Val Thr Ser Ala Ala Phe Pro
            340                 345                 350
Ser Pro Ile Glu Lys Thr Ile Ser Lys Pro Glu Gly Arg Thr Gln Val
            355                 360                 365
Pro His Val Tyr Thr Met Ser Pro Thr Lys Glu Glu Met Thr Gln Asn
            370                 375                 380
Glu Val Ser Ile Thr Cys Met Val Lys Gly Phe Tyr Pro Pro Asp Ile
385                 390                 395                 400
Tyr Val Glu Trp Gln Met Asn Gly Gln Pro Gln Glu Asn Tyr Lys Asn
                405                 410                 415
Thr Pro Pro Thr Met Asp Thr Asp Gly Ser Tyr Phe Leu Tyr Ser Lys
            420                 425                 430
Leu Asn Val Lys Lys Glu Lys Trp Gln Gln Gly Asn Thr Phe Thr Cys
            435                 440                 445
```

```
Ser Val Leu His Glu Gly Leu His Asn His Thr Glu Lys Ser Leu
    450                 455                 460
Ser His Ser Pro Gly
465
```

<210> SEQ ID NO 14
<211> LENGTH: 233
<212> TYPE: PRT
<213> ORGANISM: Artificial Sequence
<220> FEATURE:
<223> OTHER INFORMATION: 2.3D11 Light Chain (With Leader Sequence)

<400> SEQUENCE: 14

```
Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Ser
        35                  40                  45

Val Ser Ser Asn Leu Ala Trp Tyr Gln Gln Lys Pro Gly Gln Ala Pro
    50                  55                  60

Arg Leu Leu Ile Tyr Gly Ala Phe Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asp Trp Phe Thr Phe Gly Gly Gly Thr Lys Val Glu Ile Lys Arg Ala
        115                 120                 125

Asp Ala Ala Pro Thr Val Ser Ile Phe Pro Pro Ser Thr Glu Gln Leu
    130                 135                 140

Ala Thr Gly Gly Ala Ser Val Val Cys Leu Met Asn Asn Phe Tyr Pro
145                 150                 155                 160

Arg Asp Ile Ser Val Lys Trp Lys Ile Asp Gly Thr Glu Arg Arg Asp
                165                 170                 175

Gly Val Leu Asp Ser Val Thr Asp Gln Asp Ser Lys Asp Ser Thr Tyr
            180                 185                 190

Ser Met Ser Ser Thr Leu Ser Leu Thr Lys Ala Asp Tyr Glu Ser His
        195                 200                 205

Asn Leu Tyr Thr Cys Glu Val Val His Lys Thr Ser Ser Ser Pro Val
    210                 215                 220

Val Lys Ser Phe Asn Arg Asn Glu Cys
225                 230
```

<210> SEQ ID NO 15
<211> LENGTH: 450
<212> TYPE: PRT
<213> ORGANISM: Artificial Sequence
<220> FEATURE:
<223> OTHER INFORMATION: 2.3D11 Heavy Chain (Without Leader Sequence)

<400> SEQUENCE: 15

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Val Ser Ile Arg Ser Ile
            20                  25                  30

Asn Trp Trp Asn Trp Val Arg Gln Pro Pro Gly Lys Gly Leu Glu Trp
```

```
                35                  40                  45
Ile Gly Glu Ile Tyr His Ser Gly Ser Thr Asn Tyr Asn Pro Ser Leu
 50                  55                  60
Lys Ser Arg Val Thr Ile Ser Val Asp Lys Ser Lys Asn Gln Phe Ser
 65                  70                  75                  80
Leu Lys Leu Asn Ser Val Thr Ala Ala Asp Thr Ala Val Tyr Tyr Cys
                 85                  90                  95
Ala Arg Asp Gly Gly Ile Ala Val Thr Asp Tyr Tyr Tyr Gly Leu
                100                 105                 110
Asp Val Trp Gly Gln Gly Thr Thr Val Thr Val Ser Ser Ala Glu Thr
            115                 120                 125
Thr Ala Pro Ser Val Tyr Pro Leu Ala Pro Gly Thr Ala Leu Lys Ser
130                 135                 140
Asn Ser Met Val Thr Leu Gly Cys Leu Val Lys Gly Tyr Phe Pro Glu
145                 150                 155                 160
Pro Val Thr Val Thr Trp Asn Ser Gly Ala Leu Ser Ser Gly Val His
                165                 170                 175
Thr Phe Pro Ala Val Leu Gln Ser Gly Leu Tyr Thr Leu Thr Ser Ser
            180                 185                 190
Val Thr Val Pro Ser Ser Thr Trp Pro Ser Gln Thr Val Thr Cys Asn
        195                 200                 205
Val Ala His Pro Ala Ser Ser Thr Lys Val Asp Lys Lys Ile Val Pro
210                 215                 220
Arg Asn Cys Gly Gly Asp Cys Lys Pro Cys Ile Cys Thr Gly Ser Glu
225                 230                 235                 240
Val Ser Ser Val Phe Ile Phe Pro Pro Lys Pro Lys Asp Val Leu Thr
                245                 250                 255
Ile Thr Leu Thr Pro Lys Val Thr Cys Val Val Val Asp Ile Ser Gln
            260                 265                 270
Asp Asp Pro Glu Val His Phe Ser Trp Phe Val Asp Asp Val Glu Val
        275                 280                 285
His Thr Ala Gln Thr Arg Pro Pro Glu Glu Gln Phe Asn Ser Thr Phe
290                 295                 300
Arg Ser Val Ser Glu Leu Pro Ile Leu His Gln Asp Trp Leu Asn Gly
305                 310                 315                 320
Arg Thr Phe Arg Cys Lys Val Thr Ser Ala Ala Phe Pro Ser Pro Ile
                325                 330                 335
Glu Lys Thr Ile Ser Lys Pro Glu Gly Arg Thr Gln Val Pro His Val
            340                 345                 350
Tyr Thr Met Ser Pro Thr Lys Glu Glu Met Thr Gln Asn Glu Val Ser
        355                 360                 365
Ile Thr Cys Met Val Lys Gly Phe Tyr Pro Pro Asp Ile Tyr Val Glu
            370                 375                 380
Trp Gln Met Asn Gly Gln Pro Gln Glu Asn Tyr Lys Asn Thr Pro Pro
385                 390                 395                 400
Thr Met Asp Thr Asp Gly Ser Tyr Phe Leu Tyr Ser Lys Leu Asn Val
                405                 410                 415
Lys Lys Glu Lys Trp Gln Gln Gly Asn Thr Phe Thr Cys Ser Val Leu
            420                 425                 430
His Glu Gly Leu His Asn His His Thr Glu Lys Ser Leu Ser His Ser
        435                 440                 445
Pro Gly
450
```

<210> SEQ ID NO 16
<211> LENGTH: 213
<212> TYPE: PRT
<213> ORGANISM: Artificial Sequence
<220> FEATURE:
<223> OTHER INFORMATION: 2.3D11 Light Chain (Without Leader Sequence)

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Phe Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Phe Thr
                85                  90                  95

Phe Gly Gly Gly Thr Lys Val Glu Ile Lys Arg Ala Asp Ala Ala Pro
            100                 105                 110

Thr Val Ser Ile Phe Pro Pro Ser Thr Glu Gln Leu Ala Thr Gly Gly
        115                 120                 125

Ala Ser Val Val Cys Leu Met Asn Asn Phe Tyr Pro Arg Asp Ile Ser
130                 135                 140

Val Lys Trp Lys Ile Asp Gly Thr Glu Arg Arg Asp Gly Val Leu Asp
145                 150                 155                 160

Ser Val Thr Asp Gln Asp Ser Lys Asp Ser Thr Tyr Ser Met Ser Ser
                165                 170                 175

Thr Leu Ser Leu Thr Lys Ala Asp Tyr Glu Ser His Asn Leu Tyr Thr
            180                 185                 190

Cys Glu Val Val His Lys Thr Ser Ser Pro Val Val Lys Ser Phe
        195                 200                 205

Asn Arg Asn Glu Cys
    210

<210> SEQ ID NO 17
<211> LENGTH: 330
<212> TYPE: PRT
<213> ORGANISM: Homo sapiens

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 18
<211> LENGTH: 326
<212> TYPE: PRT
<213> ORGANISM: Homo sapiens

<400> SEQUENCE: 18

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140
```

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
    195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
            245                 250                 255

Ser Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 19
<211> LENGTH: 377
<212> TYPE: PRT
<213> ORGANISM: Homo sapiens

<400> SEQUENCE: 19

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val

```
                180                 185                 190
Val Val Asp Val Ser His Glu Asp Pro Glu Val Gln Phe Lys Trp Tyr
            195                 200                 205
Val Asp Gly Val Glu Val His Asn Ala Lys Thr Lys Pro Arg Glu Glu
            210                 215                 220
Gln Tyr Asn Ser Thr Phe Arg Val Val Ser Val Leu Thr Val Leu His
225                 230                 235                 240
Gln Asp Trp Leu Asn Gly Lys Glu Tyr Lys Cys Lys Val Ser Asn Lys
            245                 250                 255
Ala Leu Pro Ala Pro Ile Glu Lys Thr Ile Ser Lys Thr Lys Gly Gln
            260                 265                 270
Pro Arg Glu Pro Gln Val Tyr Thr Leu Pro Pro Ser Arg Glu Glu Met
            275                 280                 285
Thr Lys Asn Gln Val Ser Leu Thr Cys Leu Val Lys Gly Phe Tyr Pro
            290                 295                 300
Ser Asp Ile Ala Val Glu Trp Glu Ser Ser Gly Gln Pro Glu Asn Asn
305                 310                 315                 320
Tyr Asn Thr Thr Pro Pro Met Leu Asp Ser Asp Gly Ser Phe Phe Leu
            325                 330                 335
Tyr Ser Lys Leu Thr Val Asp Lys Ser Arg Trp Gln Gln Gly Asn Ile
            340                 345                 350
Phe Ser Cys Ser Val Met His Glu Ala Leu His Asn Arg Phe Thr Gln
            355                 360                 365
Lys Ser Leu Ser Leu Ser Pro Gly Lys
            370                 375

<210> SEQ ID NO 20
<211> LENGTH: 327
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
            130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 21
<211> LENGTH: 327
<212> TYPE: PRT
<213> ORGANISM: Artificial Sequence
<220> FEATURE:
<223> OTHER INFORMATION: Mutated IgG4 Constant Region (S228P/L235E)

<400> SEQUENCE: 21

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
        195                 200                 205
```

```
Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 22
<211> LENGTH: 106
<212> TYPE: PRT
<213> ORGANISM: Homo sapiens

<400> SEQUENCE: 22

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 23
<211> LENGTH: 455
<212> TYPE: PRT
<213> ORGANISM: Artificial Sequence
<220> FEATURE:
<223> OTHER INFORMATION: 2.3D11 IgG1 Heavy Chain (Without Leader
      Sequence)

<400> SEQUENCE: 23

Gln Val Gln Leu Gln Glu Ser Gly Pro Gly Leu Val Lys Pro Ser Gly
1               5                   10                  15

Thr Leu Ser Leu Thr Cys Ala Val Ser Gly Val Ser Ile Arg Ser Ile
            20                  25                  30

Asn Trp Trp Asn Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80
```

Leu Lys Leu Asn Ser Val Thr Ala Ala Asp Thr Ala Val Tyr Tyr Cys
            85                  90                  95

Ala Arg Asp Gly Gly Ile Ala Val Thr Asp Tyr Tyr Tyr Gly Leu
        100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
450                 455

<210> SEQ ID NO 24
<211> LENGTH: 452
<212> TYPE: PRT
<213> ORGANISM: Artificial Sequence
<220> FEATURE:
<223> OTHER INFORMATION: 2.3D11 IgG4 Heavy Chain (Without Leader

<400> SEQUENCE: 24

```
Gln Val Gln Leu Gln Glu Ser Gly Pro Gly Leu Val Lys Pro Ser Gly
  1               5                  10                  15
Thr Leu Ser Leu Thr Cys Ala Val Ser Gly Val Ser Ile Arg Ser Ile
             20                  25                  30
Asn Trp Trp Asn Trp Val Arg Gln Pro Pro Gly Lys Gly Leu Glu Trp
         35                  40                  45
Ile Gly Glu Ile Tyr His Ser Gly Ser Thr Asn Tyr Asn Pro Ser Leu
     50                  55                  60
Lys Ser Arg Val Thr Ile Ser Val Asp Lys Ser Lys Asn Gln Phe Ser
 65                  70                  75                  80
Leu Lys Leu Asn Ser Val Thr Ala Ala Asp Thr Ala Val Tyr Tyr Cys
                 85                  90                  95
Ala Arg Asp Gly Gly Ile Ala Val Thr Asp Tyr Tyr Tyr Gly Leu
            100                 105                 110
Asp Val Trp Gly Gln Gly Thr Thr Val Thr Val Ser Ser Ala Ser Thr
            115                 120                 125
Lys Gly Pro Ser Val Phe Pro Leu Ala Pro Cys Ser Arg Ser Thr Ser
130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
        195                 200                 205
Asn Val Asp His Lys Pro Ser Asn Thr Lys Val Asp Lys Arg Val Glu
    210                 215                 220
Ser Lys Tyr Gly Pro Pro Cys Pro Ser Cys Pro Ala Pro Glu Phe Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
Gln Glu Asp Pro Glu Val Gln Phe Asn Trp Tyr Val Asp Gly Val Glu
        275                 280                 285
Val His Asn Ala Lys Thr Lys Pro Arg Glu Glu Gln Phe Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Gln Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
```

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 25
<211> LENGTH: 452
<212> TYPE: PRT
<213> ORGANISM: Artificial Sequence
<220> FEATURE:
<223> OTHER INFORMATION: 2.3D11 IgG4mt Heavy Chain (Without Leader
      Sequence)

<400> SEQUENCE: 25

Gln Val Gln Leu Gln Glu Ser Gly Pro Gly Leu Val Lys Pro Ser Gly
1               5                   10                  15

Thr Leu Ser Leu Thr Cys Ala Val Ser Gly Val Ser Ile Arg Ser Ile
            20                  25                  30

Asn Trp Trp Asn Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
50                  55                  60

Lys Ser Arg Val Thr Ile Ser Val Asp Lys Ser Lys Asn Gln Phe Ser
65                  70                  75                  80

Leu Lys Leu Asn Ser Val Thr Ala Ala Asp Thr Ala Val Tyr Tyr Cys
            85                  90                  95

Ala Arg Asp Gly Gly Ile Ala Val Thr Asp Tyr Tyr Tyr Gly Leu
        100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

```
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Gln Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 26
<211> LENGTH: 212
<212> TYPE: PRT
<213> ORGANISM: Artificial Sequence
<220> FEATURE:
<223> OTHER INFORMATION: 2.3D11 Kappa Light Chain

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Phe Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Phe Thr
                85                  90                  95

Phe Gly Gly Gly Thr Lys Val Glu Ile Lys Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205
```

Arg Gly Glu Cys
    210

<210> SEQ ID NO 27
<211> LENGTH: 118
<212> TYPE: PRT
<213> ORGANISM: Artificial Sequence
<220> FEATURE:
<223> OTHER INFORMATION: AB6.12-IgG4PE Heavy Chain Variable Region

<400> SEQUENCE: 27

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Gln Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 28
<211> LENGTH: 107
<212> TYPE: PRT
<213> ORGANISM: Artificial Sequence
<220> FEATURE:
<223> OTHER INFORMATION: AB6.12-IgG4PE Light Chain Variable Region

<400> SEQUENCE: 28

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys His Leu Ile
        35                  40                  45

Tyr Arg Ala Asn Arg Leu Val Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 29
<211> LENGTH: 117
<212> TYPE: PRT
<213> ORGANISM: Artificial Sequence
<220> FEATURE:
<223> OTHER INFORMATION: 5F9G4 Heavy Chain Variable Region

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser
            115

<210> SEQ ID NO 30
<211> LENGTH: 112
<212> TYPE: PRT
<213> ORGANISM: Artificial Sequence
<220> FEATURE:
<223> OTHER INFORMATION: 5F9G4 Light Chain Variable Region

<400> SEQUENCE: 30

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
            100                 105                 110

<210> SEQ ID NO 31
<211> LENGTH: 118
<212> TYPE: PRT
<213> ORGANISM: Artificial Sequence
<220> FEATURE:
<223> OTHER INFORMATION: B6H12 Heavy Chain Variable Region

<400> SEQUENCE: 31

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Asp Lys Arg Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Lys Ser Glu Asp Thr Ala Ile Tyr Phe Cys
                85                  90                  95

Ala Arg Ser Leu Ala Gly Asn Ala Met Asp Tyr Trp Gly Gln Gly Thr
            100                 105                 110

Ser Val Thr Val Ser Ser
        115

<210> SEQ ID NO 32
<211> LENGTH: 107
<212> TYPE: PRT
<213> ORGANISM: Artificial Sequence
<220> FEATURE:
<223> OTHER INFORMATION: B6H12 Light Chain Variable Region

<400> SEQUENCE: 32

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Gly Phe Pro Arg
                85                  90                  95

Thr Phe Gly Gly Gly Thr Lys Leu Glu Ile Lys
            100                 105

<210> SEQ ID NO 33
<211> LENGTH: 452
<212> TYPE: PRT
<213> ORGANISM: Homo sapiens

<400> SEQUENCE: 33

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
        435                 440                 445

Gly Thr Cys Tyr
    450

<210> SEQ ID NO 34
<211> LENGTH: 105
<212> TYPE: PRT
<213> ORGANISM: Homo sapiens

<400> SEQUENCE: 34

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
            85                  90                  95

Glu Lys Thr Val Ala Pro Thr Glu Cys
            100                 105

<210> SEQ ID NO 35
<211> LENGTH: 1465
<212> TYPE: DNA
<213> ORGANISM: Artificial Sequence
<220> FEATURE:
<223> OTHER INFORMATION: 2.3D11 IgG1 Heavy Chain

<400> SEQUENCE: 35
aagcttaccg ccaccatggg ttggtcctgc atcatcctgt tcctggtggc cacggccacc      60
ggcgtgcact cccaagtcca actccaggag tccggcccg ggctggtcaa gccgtccggc     120
acactgtccc tgacgtgcgc cgtctccggg gtctctatcc ggagcatcaa ctggtggaat    180
tgggtgcggc agccgcccgg taagggcctc gagtggattg gcgagatcta ccactcaggc    240
agcaccaact acaaccectc cctcaagtcg cgcgtcacga tctcggtcga caagtccaag    300
aaccagttct cgctcaagct caacagcgtg accgcggcgg acaccgccgt gtactactgt    360
gcccgggacg gcggcatcgc agtcactgac tactactatt acggcctcga cgtgtggggc    420
caggggacga cggtcacggt gagctccgcc tccaccaaag gcccagcgt cttccctc       480 gcgccgtcct ccaagtccac ctcgggtggc accgccgccc tgggctgcct ggtcaaggac    540
tacttcccgg agcctgtgac cgtgtcctgg aactcgggcg cgctcacgag cggcgtacac    600
accttcccgg cggtgctcca gtcctccggg ctgtactcgc tctcgtcggt cgtcacggtg    660
ccgtcctcct ccctgggcac ccagacctac atctgcaacg tgaaccacaa gccgtccaac    720
accaaggtgg ataagaaggt cgagcccaag tcgtgcgaca agacgcacac gtgcccgccg    780
tgccccgccc cggagctgct gggcggcccc tcggtcttcc tgttcccccc gaagcccaag    840
gatacgctga tgatctcccg cacccggag gtcacctgcg tggtggtgga cgtctcccac    900
gaggacccgg aggtgaaatt caactggtac gtcgacggag tggaggtcca caacgccaag    960
accaagcccc gggaggagca gtacaactcc acgtaccgcg tcgtctccgt cctgaccgtc   1020
ctccaccagg actggctgaa cggcaaggag tacaagtgta aggtctccaa caaggcgctg   1080
cccgccccca tcgagaagac catctccaag gcaaagggtc agccgcggga gccgcaggtc   1140 tatacctcc ccccgtcccg cgacgagctg acgaaaaacc aggtctccct gacctgcctg   1200
gtgaagggtt tctaccctc cgacatcgcg gtcgagtggg agtcgaacgg ccagccggag   1260
aacaactaca agaccacccc ccccgtgctc gacagtgacg gctcgttctt cctgtactcg   1320
aagctgaccg tcgacaagtc gcgctggcag cagggcaacg tcttctcgtg ctccgttatg   1380
cacgaggccc tgcacaacca ctacacgcag aagagtcttt cgctgtcccc ggggaagtga   1440
taatctagag tcggggcggc cggcc                                         1465

<210> SEQ ID NO 36
<211> LENGTH: 1456
<212> TYPE: DNA
<213> ORGANISM: Artificial Sequence
<220> FEATURE:
<223> OTHER INFORMATION: 2.3D11 IgG4 Heavy Chain

<400> SEQUENCE: 36
aagcttaccg ccaccatggg gtggtcgtgc atcatcctct tcctggtcgc caccgcgacc      60

| | |
|---|---:|
| ggcgtgcatt cgcaggtcca gctccaggag agcggcccgg gcctggtgaa gccctccggc | 120 |
| acgctctctc tgacgtgcgc cgtctcggga gtgagtatcc gctcgatcaa ctggtggaac | 180 |
| tgggtgcggc agccgccggg caagggcctg aatggatcg gggagatcta ccactccggg | 240 |
| tcgaccaact acaacccgag cctgaagtcc cgggtcacga tcagcgtgga caagtccaag | 300 |
| aaccagttct ccctgaagct gaacagtgta acggcggcgg acacggcggt ctactactgt | 360 |
| gcgcgcgacg gcggcatcgc cgtgaccgat tactactact acggcctcga cgtatggggc | 420 |
| cagggcacca ccgtcacggt gtcgagcgca tcgacgaagg gccctccgt gttccccta | 480 |
| gccccgtgct cccgcagcac ctctgagtcc acggcggcct gggctgcct cgtgaaggac | 540 |
| tacttcccgg agccggtcac tgtgtcgtgg aactccggcg cgctgaccag cggggtccac | 600 |
| accttccccg ccgtcctgca gtcgtcgggc ctgtactccc tgagctcggt ggtgaccgtc | 660 |
| ccctccagct ccctcggcac taagacctat acctgcaacg tcgaccacaa gccgtccaac | 720 |
| accaaggtgg acaagcgagt ggaatcgaag tacggcccgc cctgcccctc ctgccccgcc | 780 |
| cccgagttcc tgggggcccc gagcgtcttc ctgttcccgc cgaagccgaa ggacacgctg | 840 |
| atgatcagcc ggacgccgga agtgacgtgc gtcgtcgtgg acgtgtccca ggaagaccct | 900 |
| gaggtgcagt tcaactggta cgtggacggc gtggaggtgc acaacgcgaa aaccaagccg | 960 |
| cgcgaggagc agttcaacag cacctaccgc gtcgtgagcg tcctgacggt gctgcaccag | 1020 |
| gactggctca acggcaagga gtacaagtgc aaggtatcca acaagggact gccgtcgtcc | 1080 |
| atcgagaaga ccatctccaa ggccaagggc cagccccggg agcccaagt ctacaccctc | 1140 |
| cccccgtcgc aggaggagat gacgaagaac caggtctccc tgacctgtct cgtcaagggc | 1200 |
| ttctacccct ccgacatcgc cgtcgagtgg gagtccaacg gcagcccga gaacaactac | 1260 |
| aagaccaccc cgccagtcct ggacagtgac gggtcgttct cctgtactc ccgactcact | 1320 |
| gtggacaaga gccgctggca agaggggaac gtcttctcct gctcagtgat gcacgaggcc | 1380 |
| ctccacaacc actacaccca aaagtcgctg tccctgtccc tcgggaaatg ataatctaga | 1440 |
| gtcggggcgg ccggcc | 1456 |

<210> SEQ ID NO 37
<211> LENGTH: 1456
<212> TYPE: DNA
<213> ORGANISM: Artificial Sequence
<220> FEATURE:
<223> OTHER INFORMATION: 2.3D11 IgG4mt Heavy Chain

<400> SEQUENCE: 37

| | |
|---|---:|
| aagcttaccg ccaccatggg gtggtcgtgc atcatcctct tcctggtcgc caccgcgacc | 60 |
| ggcgtgcatt cgcaggtcca gctccaggag agcggcccgg gcctggtgaa gccctccggc | 120 |
| acgctctctc tgacgtgcgc cgtctcggga gtgagtatcc gctcgatcaa ctggtggaac | 180 |
| tgggtgcggc agccgccggg caagggcctg aatggatcg gggagatcta ccactccggg | 240 |
| tcgaccaact acaacccgag cctgaagtcc cgggtcacga tcagcgtgga caagtccaag | 300 |
| aaccagttct ccctgaagct gaacagtgta acggcggcgg acacggcggt ctactactgt | 360 |
| gcgcgcgacg gcggcatcgc cgtgaccgat tactactact acggcctcga cgtatggggc | 420 |
| cagggcacca ccgtcacggt gtcgagcgca tcgacgaagg gccctccgt gttccccta | 480 |
| gccccgtgct cccgcagcac ctctgagtcc acggcggcct gggctgcct cgtgaaggac | 540 |
| tacttcccgg agccggtcac tgtgtcgtgg aactccggcg cgctgaccag cggggtccac | 600 |
| accttccccg ccgtcctgca gtcgtcgggc ctgtactccc tgagctcggt ggtgaccgtc | 660 |

```
ccctccagct ccctcggcac taagacctat acctgcaacg tcgaccacaa gccgtccaac    720
accaaggtgg acaagcgagt ggaatcgaag tacggcccgc cctgccccc  ctgccccgcc    780 cccgagttcg agggcgggcc gagcgtcttc ctgttcccgc cgaagccgaa ggacacgctg    840
atgatcagcc ggacgccgga agtgacgtgc gtcgtcgtgg acgtgtccca ggaagaccct    900
gaggtgcagt tcaactggta cgtggacggc gtggaggtgc acaacgcgaa aaccaagccg    960
cgcgaggagc agttcaacag cacctaccgc gtcgtgagcg tcctgacggt gctgcaccag   1020
gactggctca acggcaagga gtacaagtgc aaggtatcca caagggact  gccgtcgtcc   1080 atcgagaaga ccatctccaa ggccaagggc cagccccggg agcccaagt  ctacaccctc   1140 cccccgtcgc aggaggagat gacgaagaac caggtctccc tgacctgtct cgtcaagggc   1200
ttctacccct ccgacatcgc cgtcgagtgg gagtccaacg ggcagcccga gaacaactac   1260
aagaccaccc cgccagtcct ggacagtgac gggtcgttct tcctgtactc ccgactcact   1320
gtggacaaga gccgctggca agaggggaac gtcttctcct gctcagtgat gcacgaggcc   1380
ctccacaacc actacaccca aaagtcgctg tccctgtccc tcgggaaatg ataatctaga   1440
gtcggggcgg ccggcc                                                   1456

<210> SEQ ID NO 38
<211> LENGTH: 736
<212> TYPE: DNA
<213> ORGANISM: Artificial Sequence
<220> FEATURE:
<223> OTHER INFORMATION: 2.3D11 Kappa Light Chain

<400> SEQUENCE: 38
aagcttaccg ccaccatggg gtggtcgtgc atcatcctct tcctggtggc caccgccacg     60
ggcgtccact ccgagatcgt cctgacccag tcccccgcca ccctctccct gtcgccgggc    120
gagcgggcca cgctgtcgtg ccgggcgtcc gagtcggtct cgtcgaacct cgcctggtat    180
cagcagaagc ccggccaggc gccgcgcctc ctcatctacg gcgccttcaa tcgcgccacg    240
ggcatccccg ccggttctc  cggctccgga tcggggaccg acttcaccct caccatctcc    300
tcgctggagc cggaggactt cgccgtctac tactgccagc aacggtcgga ctggttcacc    360
ttcggaggcg gcaccaaggt cgagatcaag acggtggccg cgccgagcgt cttcatcttc    420
ccgccttccg acgagcagct caagtccggg accgcctccg tagtatgcct cctcaataac    480
ttctaccccc gggaggcgaa ggtccagtgg aaggtcgaca cgccctcca  atcgggcaac    540 tcccaggagt cggtgaccga gcaggattcc aaggactcga cctacagtct aagctccacc    600
ctcacactgt cgaaggcgga ctacgagaag cacaaggtgt acgcctgcga ggtcacccac    660
cagggcctga gcagcccggt caccaagtcc ttcaaccggg gcgagtgctg ataatctaga    720
gtcggggcgg ccggcc                                                   736
```

ANTI-CD47 ANTIBODIES AND METHODS OF USE

CROSS REFERENCE TO RELATED APPLICATIONS

This application is a divisional of U.S. patent application Ser. No. 15/271,861, filed Sep. 21, 2016, which claims the benefit of, and priority to, U.S. provisional patent application Ser. No. 62/221,446, filed Sep. 21, 2015, and U.S. provisional patent application Ser. No. 62/371,047 filed Aug. 4, 2016, each of which are hereby incorporated by reference herein in their entirety.

FIELD OF THE INVENTION

The invention relates generally to molecular biology, immunology and oncology, and, more particularly, the invention relates to antibodies that bind CD47.

BACKGROUND OF THE INVENTION

The transmembrane protein CD47, also known as integrin-associated protein (IAP), ovarian cancer antigen OA3, Rh-related antigen and MER6, is an immunoglobulin superfamily member involved in multiple cellular processes, including cell migration, adhesion and T cell function. CD47 was originally identified as a tumor antigen on human ovarian cancer and was subsequently shown to be expressed on multiple human tumor types, including both hematologic and solid tumors. The interaction between CD47 and signal regulatory protein alpha (SIRPα), an inhibitory protein expressed on macrophages, prevents phagocytosis of CD47-expressing cells. CD47 is expressed at low levels on virtually all non-malignant cells, and loss of expression or changes in membrane distribution can serve as markers of aged or damaged cells, particularly on red blood cells (RBC).

However, high expression of CD47 on cancer cells blocks phagocytic uptake, subsequent antigen cross-presentation and T cell activation, which collectively contribute to tumor immune evasion. Certain human leukemias upregulate CD47 to evade macrophage killing (U.S. Pat. No. 8,562,997). In many hematologic cancers, high CD47 expression is believed to be associated with poor clinical outcomes, for example, Non-Hodgkin Lymphoma, Acute Lymphocytic Leukemia, etc. (U.S. Pat. No. 9,045,541). Similarly, high CD47 expression has been observed in solid tumors such as small cell lung cancer (see, Weiskopf et al. (2016) J. CLIN. INVESTIGATION 126(7): 2610-2620). Agents that block the CD47-SIRPα interaction can restore phagocytic uptake of CD47$^+$ target cells and lower the threshold for macrophage activation, which can enhance the efficacy of therapeutic antibodies with ADCC-enabling activity.

Despite the advances made to date, there is still ongoing need for additional agents that block the CD47-SIRPα interaction for use in the treatment of various diseases, including cancers, that are associated with elevated levels of CD47 expression.

SUMMARY OF THE INVENTION

Many CD47 antibodies developed to date have been reported to cause aggregation of cells, for example, hemagglutination of human erythrocytes (see, U.S. Pat. No. 9,045,541). As a consequence, the aggregation of cells, for example, erythrocytes, can limit the therapeutic utility of anti-CD47 antibodies that have this feature. The invention provides antibodies that bind CD47 and disrupt the interaction between CD47 and SIRPα, but have little or no hemagglutination activity at the dosage at which the antibody is administered to a subject in need of therapy with an anti-CD47 antibody, for example, a subject with a cancer, for example, a hematologic cancer or solid tumor.

The invention is based, in part, on the development and characterization of a series of antibody molecules that bind with high affinity to human CD47, block the CD47-SIRPα interaction, and promote macrophage-mediated phagocytic clearance of CD47-expressing cancer cells while inducing little or no hemagglutination of red blood cells. The anti-CD47 antibody molecules disclosed herein display significant tumor growth inhibition in models for multiple myeloma, diffuse large B cell lymphoma (DLBCL), and Burkitt's lymphoma, as a single agent and in combination with an opsonizing antibody. The anti-CD47 antibody molecules disclosed herein can be used (alone or in combination with other agents or therapeutic modalities) to treat, prevent and/or diagnose disorders such as cancer and precancerous conditions. The CD47 antibodies described herein are useful in treating, delaying the progression of, preventing relapse of, or alleviating one or more symptoms of a cancer or a precancerous lesion, and are useful in treating hematological malignancies and/or tumors.

In certain embodiments, the anti-CD47 antibody molecules described herein are capable of blocking the interaction between CD47 and its cognate SIRPα ligand, without causing significant, or detectable, hemagglutination of erythrocytes, e.g., human erythrocytes. For example, the antibody molecules cause less hemagglutination of human erythrocytes than a reference anti-CD47 antibody, or cause less than 90%, 80%, 70%, 60%, 50%, 40%, 30%, 20%, or 10% or less hemagglutination of human erythrocytes relative to a reference anti-CD47 antibody. Exemplary reference antibodies include B6H12, MABL, BRIC126, and CC2C6.

In one embodiment, the anti-CD47 antibody molecules described herein cause a potent blocking of the interaction between CD47 and SIRPα without causing a significant level of hemagglutination of erythrocytes, as well as potent anti-cancer activity. For example, the anti-CD47 antibody molecules described block at least 40%, at least 50%, at least 55%, at least 60%, at least 65%, at least 70%, at least 75%, at least 80%, at least 85%, at least 90%, at least 95%, at least 99% of the interaction between CD47 and SIRPα as compared to the level of interaction between CD47 and SIRPα in the absence of the anti-CD47 antibody molecules described herein. Optionally, the antibody molecules also cause less hemagglutination of human erythrocytes than a reference anti-CD47 antibody, or cause less than 90%, 80%, 70%, 60%, 50%, 40%, 30%, 20%, or 10% or less hemagglutination of human erythrocytes relative to a reference anti-CD47 antibody. Exemplary reference antibodies include B6H12, MABL, BRIC126, and CC2C6.

In one embodiment, the anti-CD47 antibody molecules described herein do not phagocytose red blood cells to a significant or detectable level. In another embodiment, the anti-CD47 antibody molecules have reduced (e.g., 10%, 20%, 30%, 40%, 50%, 60%, 70%, 80%, or 90% reduced) phagocytic activity towards red blood cells relative to a reference anti-CD47 antibody, e.g., as determined by a phagocytosis assay described herein. Exemplary reference antibodies include B6H12, MABL, BRIC126, and CC2C6.

In another embodiment, the anti-CD47 antibody molecules described herein enhance macrophage activity. For example, the antibody molecules enhance the phagocytic activity of a macrophage, e.g., an unpolarized macrophage, or an M1 or M2 polarized macrophage. In one embodiment, the phagocytic activity is enhanced, e.g., 1%, 5%, 10%, 20%, 30%, 40%, 50%, 60%, 70%, 80%, or 90%, relative to a macrophage in the absence of an anti-CD47 antibody molecule described herein.

In one embodiment, the anti-CD47 antibody molecules described herein enhance macrophage phagocytic activity towards a cancer cell, e.g., an AML cell. In one embodiment, the phagocytic activity is enhanced, e.g., 1%, 5%, 10%, 20%, 30%, 40%, 50%, 60%, 70%, 80%, or 90%, relative to a macrophage in the absence of an anti-CD47 antibody molecule described herein.

In one embodiment, the anti-CD47 antibody molecules described herein, when used in combination with an opsonizing antibody (e.g., one or more of, an anti-CD19 antibody, an anti-CD20 antibody, an anti-CD38 antibody, or an anti-HER2/neu receptor antibody) enhance the anti-tumor effect of the combination, relative to the anti-tumor effect of each antibody individually. In another embodiment, the anti-tumor effect of the combination is enhanced, e.g., 10%, 20%, 30%, 40%, 50%, 60%, 70%, 80%, or 90% or higher, relative to the activity of either the anti-CD47 antibody molecule or the opsonizing antibody individually.

In one aspect, the anti-CD47 antibody molecule comprises: a heavy chain complementarity determining region 1 (HC CDR1) of the amino acid sequence set forth in SEQ ID NO: 7, a heavy chain complementarity determining region 2 (HC CDR2) of the amino acid sequence set forth in SEQ ID NO: 8, a heavy chain complementarity determining region 3 (HC CDR3) of the amino acid sequence set forth in SEQ ID NO: 9; and a light chain complementarity determining region 1 (LC CDR1) of the amino acid sequence set forth in SEQ ID NO: 10, a light chain complementarity determining region 2 (LC CDR2) of the amino acid sequence set forth in SEQ ID NO: 11, and a light chain complementarity determining region 3 (LC CDR3) of the amino acid sequence set forth in SEQ ID NO: 12.

In an embodiment, an antibody molecule of the invention comprises one or both of (a) and (b), wherein (a) and (b) are as follows:

(a)(i) light chain CDR1, CDR2 and CDR3, e.g., Chothia or Kabat light chain CDRs, from SEQ ID NO: 16, (a)(ii) light chain CDR1 of SEQ ID NO: 10, light chain CDR2 of SEQ ID NO: 11, and light chain CDR3 of SEQ ID NO: 12, (a)(iii) light chain CDRs CDR1, CDR2 and CDR3, that collectively, differ by no more than 1, 2, 3, 4, 5, or 6 amino acid residues from the light chain CDRs of (a)(i) and (a)(ii);

(a)(iv) a light chain variable region of SEQ ID NO: 6;

(a)(v) an antigen binding fragment of SEQ ID NO: 6;

(a)(vi) an amino acid sequence that differs by no more than 1, 2, 3, 4, 5, 6, 7, 8, 9, or 10, residues from the sequence of (a)(iv) or a)(v);

(a)(vii) an amino acid sequence that is substantially identical (e.g., at least 85%, 90%, 92%, 95%, 97%, 98%, or 99% identical) to the sequence of (a)(iv) or (a)(v); and (b)(i) heavy chain CDR1, CDR2 and CDR3, e.g., Chothia or Kabat heavy chain CDRs, from SEQ ID NO: 15, (b)(ii) heavy chain CDR1 of SEQ ID NO: 7, heavy chain CDR2 of SEQ ID NO: 8, and heavy chain CDR3 of SEQ ID NO: 9, (b)(iii) heavy chain CDRs CDR1, CDR2 and CDR3, that collectively, differ by no more than 1, 2, 3, 4, 5, or 6 amino acid residues from the heavy chain CDRs of (b)(i) and (b)(ii);

(b)(iv) a heavy chain variable region of SEQ ID NO: 4;

(b)(v) an antigen binding fragment of SEQ ID NO: 4;

(b)(vi) an amino acid sequence that differs by no more than 1, 2, 3, 4, 5, 6, 7, 8, 9, or 10, residues from the sequence of (b)(iv) or (b)(v); and (b)(vii) an amino acid sequence that is substantially identical (e.g., at least 85%, 90%, 92%, 95%, 97%, 98%, or 99% identical) to the sequence of (b)(iv) or (b)(v).

In an embodiment, the antibody molecule comprises (a)(i) and (b)(i).

In an embodiment, the antibody molecule comprises (a)(ii) and (b)(ii).

In an embodiment, the antibody molecule comprises (a)(iii) and (b)(iii).

In an embodiment, the antibody molecule comprises (a)(iv) and (b)(iv).

In an embodiment, the antibody molecule comprises (a)(v) and (b)(v).

In an embodiment, the antibody molecule comprises (a)(vi) and (b)(vi).

In an embodiment, the antibody molecule competes for binding to CD47 with an antibody described herein, e.g., competes for binding with the antibody 2.3D11, discussed hereinbelow.

In an embodiment, the antibody molecule described herein binds the same or an overlapping epitope on CD47 as an antibody described herein, e.g., the antibody 2.3D11.

In an embodiment, the anti-CD47 antibody molecule is a bispecific antibody molecule. For example, the bispecific antibody molecule can comprise a first binding specificity to CD47, e.g., an antibody that binds CD47 as described herein, and a second binding specificity. The second binding specificity can be imparted via a binding domain obtained from an opsonizing antibody, e.g., an antibody that binds CD19, CD20, CD38, or HER2/neu receptor.

It is understood that the variable region sequences of the antibodies described herein can be linked to a variety of constant region sequences. For example, in one embodiment, the anti-CD47 antibody molecule can have a wild-type heavy chain constant region (Fc). In another embodiment, the anti-CD47 antibody molecule can have a mutated form of a heavy chain constant region. In one embodiment, the heavy chain constant region is chosen from, e.g., a heavy chain constant region of an IgG1, IgG2, IgG3, IgG4, IgM, IgA1, IgA2, IgD, and IgE; preferably, chosen from, e.g., a heavy chain constant region of IgG1, IgG2, IgG3, and IgG4. In one embodiment, the anti-CD47 antibody molecule has an IgG1 heavy chain constant region, e.g., a wild-type or mutant IgG1 heavy chain constant region. In another embodiment, the anti-CD47 antibody molecule has an IgG4 heavy chain constant region, e.g., a wild-type or mutant IgG4 heavy chain constant region. In one embodiment, the IgG4 heavy chain constant region comprises one or both of the substitutions, serine to proline at position 228 (S228P) and leucine to glutamate at position 235 (L235E), e.g., according to EU numbering.

In another embodiment, the anti-CD47 antibody molecule has a light chain constant region chosen from, e.g., the light chain constant regions of kappa or lambda.

In another aspect, the invention also provides compositions comprising an anti-CD47 antibody molecule described herein and at least one pharmaceutically acceptable carrier or diluent. For example, the composition comprises an isolated anti-CD47 antibody molecule, comprising: a heavy chain complementarity determining region 1 (HC CDR1) of the amino acid sequence set forth in SEQ ID NO: 7, a heavy chain complementarity determining region 2 (HC CDR2) of the amino acid sequence set forth in SEQ ID NO: 8, a heavy chain complementarity determining region 3 (HC CDR3) of the amino acid sequence set forth in SEQ ID NO: 9; and a light chain complementarity determining region 1 (LC CDR1) of the amino acid sequence set forth in SEQ ID NO: 10, a light chain complementarity determining region 2 (LC CDR2) of the amino acid sequence set forth in SEQ ID NO: 11, and a light chain complementarity determining region 3 (LC CDR3) of the amino acid sequence set forth in SEQ ID NO: 12, and at least one pharmaceutically acceptable carrier or diluent.

In one embodiment, the isolated anti-CD47 antibody molecules disclosed herein, comprise a heavy chain variable region (VH) of the amino acid sequence set forth in SEQ ID NO: 4, or a sequence substantially identical (e.g., at least 85%, 90%, 92%, 95%, 97%, 98%, or 99% identical) to SEQ ID NO: 4; and a light chain variable region (VL) of the amino acid sequence set forth in SEQ ID NO: 6, or a sequence substantially identical (e.g., at least 85%, 90%, 92%, 95%, 97%, 98%, or 99% identical) to SEQ ID NO: 6.

In one embodiment, the composition comprises an isolated anti-CD47 antibody molecule having a heavy chain variable region (VH) of the amino acid sequence set forth in SEQ ID NO: 4, or a sequence substantially identical (e.g., at least 85%, 90%, 92%, 95%, 97%, 98%, or 99% identical) to SEQ ID NO: 4; and a light chain variable region (VL) of the amino acid sequence set forth in SEQ ID NO: 6, or a sequence substantially identical (e.g., at least 85%, 90%, 92%, 95%, 97%, 98%, or 99% identical) to SEQ ID NO: 6, and at least one pharmaceutically acceptable carrier or diluent.

In one embodiment, the isolated anti-CD47 antibody molecule comprises: a heavy chain of the amino acid sequence set forth in SEQ ID NO: 15, or a sequence substantially identical (e.g., at least 85%, 90%, 92%, 95%, 97%, 98%, or 99% identical) to SEQ ID NO: 15; and a light chain of the amino acid sequence set forth in SEQ ID NO: 16, or a sequence substantially identical (e.g., at least 85%, 90%, 92%, 95%, 97%, 98%, or 99% identical) to SEQ ID NO: 16.

In one embodiment, the composition comprises an isolated anti-CD47 antibody molecule comprising: a heavy chain of the amino acid sequence set forth in SEQ ID NO: 15, or a sequence substantially identical (e.g., at least 85%, 90%, 92%, 95%, 97%, or 98%, 99% identical) to SEQ ID NO: 15; and a light chain of the amino acid sequence set forth in SEQ ID NO: 16, or a sequence substantially identical (e.g., at least 85%, 90%, 92%, 95%, 97%, 98%, or 99% identical) to SEQ ID NO: 16, and at least one pharmaceutically acceptable carrier or diluent.

In embodiments of any of the aforementioned antibody molecules or compositions, an anti-CD47 antibody molecule comprising a substantially identical heavy chain and/or light chain sequence to a reference SEQ ID NO (e.g., the heavy chain of SEQ ID NO: 15 or the light chain of SEQ ID NO: 16) comprises one, two, or three VH CDRs, and/or one, two, or three VL CDRs, having an amino acid sequence that is identical to the corresponding reference CDR sequence.

In another aspect, the invention provides a method of treating (or preventing) cancer in a subject, the method comprising administering an anti-CD47 antibody molecule or a composition comprising an isolated anti-CD47 antibody molecule to the subject. For example, the invention provides a method of treating (or preventing) cancer in a subject, the method comprising: administering an anti-CD47 antibody molecule described herein, or a composition comprising an isolated anti-CD47 antibody molecule described herein, to the subject.

In one embodiment, the anti-CD47 antibody molecule comprises: a heavy chain complementarity determining region 1 (HC CDR1) of the amino acid sequence set forth in SEQ ID NO: 7, a heavy chain complementarity determining region 2 (HC CDR2) of the amino acid sequence set forth in SEQ ID NO: 8, a heavy chain complementarity determining region 3 (HC CDR3) of the amino acid sequence set forth in SEQ ID NO: 9; and a light chain complementarity determining region 1 (LC CDR1) of the amino acid sequence set forth in SEQ ID NO: 10, a light chain complementarity determining region 2 (LC CDR2) of the amino acid sequence set forth in SEQ ID NO: 11, and a light chain complementarity determining region 3 (LC CDR3) of the amino acid sequence set forth in SEQ ID NO: 12.

In certain embodiments, a composition, e.g., a composition comprising an anti-CD47 antibody described herein, is administered by a mode selected from the group consisting of: parenteral, subcutaneous, intramuscular, intravenous, intra-articular, intra-abdominal, intracapsular, intracartilaginous, intracavitary, intracelial, intracolic, intracervical, intragastric, intrahepatic, intramyocardial, intraosteal, intrapelvic, intraperitoneal, intrapleural, intraprostatic, intrapulmonary, intrarectal, intraspinal, intrasynovial, rectal, buccal, sublingual, intranasal, and transdermal delivery. In certain embodiments, the composition is administered subcutaneously. In certain embodiments, the composition is administered intravenously.

In certain embodiments, an anti-CD47 antibody molecule, for example, an anti-CD47 antibody described herein or a composition comprising an anti-CD47 antibody molecule or a composition comprising an anti-CD47 antibody described herein, is administered in combination with a chemotherapeutic agent or a second therapeutic antibody molecule. For example, in one embodiment, an anti-CD47 antibody molecule or composition, e.g., an anti-CD47 antibody molecule or composition described herein, is administered in combination with an opsonizing antibody. Without wishing to be bound by theory, the opsonizing antibody can facilitate phagocytosis or antibody dependent cellular cytotoxicity (ADCC), or both, of a target cell, e.g., a cancer cell. In one embodiment, the antigen binding portion of the opsonizing antibody binds to a target antigen, whereas the Fc portion of the opsonizing antibody binds to an Fc receptor on a phagocyte. In other embodiments, the antigen binding portion of the opsonizing antibody binds to a target antigen, whereas the Fc portion of the opsonizing antibody binds to an immune effector cell, e.g., via its Fc domain, thus triggering target cell lysis by the bound effector cell (e.g., monocytes, neutrophils and natural killer cells).

In certain embodiments, the opsonizing antibody is an anti-CD20 antibody molecule, for example, rituximab. In certain embodiments, the opsonizing antibody is an anti-CD19 antibody molecule. In certain embodiments, the opsonizing antibody is an anti-CD38 antibody molecule. In certain embodiments, the opsonizing antibody is an anti-HER2/neu receptor antibody molecule.

In certain embodiments, the antibody molecules can be used to treat a hematological cancer, for example, a hematological cancer selected from the group consisting of: acute lymphoblastic leukemia (ALL), acute myelogenous leukemia (AML), Non-Hodgkin lymphoma (e.g., diffuse large B cell lymphoma, chronic lymphocytic leukemia, mantle cell lymphoma, B lymphoblastic leukemia/lymphoma, and Burkitt's lymphoma), B-lymphoblastic leukemia/lymphoma; B-cell chronic lymphocytic leukemia/small lymphocytic lymphoma, chronic lymphocytic leukemia (CLL), e.g., transformed CLL, Richter's syndrome, chronic myelocytic leukemia (CML), follicular lymphoma, multiple myeloma, myelofibrosis, polycythemia vera, cutaneous T-cell lymphoma, monoclonal gammopathy of unknown significance (MGUS), myelodysplastic syndrome (MDS), immunoblastic large cell lymphoma, precursor B-lymphoblastic lymphoma and anaplastic large cell lymphoma.

In one embodiment, the cancer is a hematological cancer chosen from multiple myeloma, diffuse large B cell lymphoma, AML, CLL, e.g., transformed CLL, Richter's syndrome, or follicular lymphoma. In certain embodiments, the antibody molecules can be used to treat a solid tumor. In certain embodiments, the cancer is selected from the group consisting of lung (e.g., non-small cell lung cancer, small cell lung cancer), pancreas, breast, liver, ovary, testicle, kidney, bladder, spine, brain, cervix, endometrial, colon/rectum, anus, endometrium, esophagus, gallbladder, gastrointestinal tract, skin, prostate, pituitary, stomach, uterus, vagina, and thyroid. In certain embodiments, the solid tumor is N-methyl-D-aspartate receptor (NMDA receptor) positive teratoma. In certain embodiments, the cancer is a cancer associated with ascites selected from breast cancer, colon cancer, stomach cancer, pancreatic cancer, uterine cancer, and ovarian cancer. In one embodiment, the cancer associated with ascites is an adenocarcinoma.

In certain embodiments, the method of preventing a cancer comprises treating a precancerous condition or a condition associated with increased risk of developing cancer. Exemplary precancerous conditions include plasma cell dyscrasias, including a monoclonal gammopathy of unknown significance (MGUS), which are associated with an increased risk for development of multiple myeloma and other hematologic malignancies.

In another aspect, the invention provides one or more isolated nucleic acid molecules that encode at least a portion (for example, one of the heavy or light chain sequences) of the anti-CD47 antibody molecules described herein.

In one embodiment, the nucleic acid molecule comprises a nucleic acid sequence encoding a heavy chain complementarity determining region 1 (HC CDR1) of the amino acid sequence set forth in SEQ ID NO: 7, a heavy chain complementarity determining region 2 (HC CDR2) of the amino acid sequence set forth in SEQ ID NO: 8, and a heavy chain complementarity determining region 3 (HC CDR3) of the amino acid sequence set forth in SEQ ID NO: 9, and/or a light chain complementarity determining region 1 (LC CDR1) of the amino acid sequence set forth in SEQ ID NO: 10, a light chain complementarity determining region 2 (LC CDR2) of the amino acid sequence set forth in SEQ ID NO: 11, and a light chain complementarity determining region 3 (LC CDR3) of the amino acid sequence set forth in SEQ ID NO: 12. It is contemplated that the nucleic acid encodes (i) HC CDR1, HC CDR2, and HC CDR3; (ii) LC CDR1, LC CDR2, and LC CDR3; or (iii) HC CDR1, HC CDR2, HC CDR3, LC CDR1, LC CDR2, and LC CDR3.

In certain embodiments, the one or more isolated nucleic acid molecules encode an anti-CD47 antibody molecule comprising: a heavy chain variable region (VH) of the amino acid sequence set forth in SEQ ID NO: 4, or a sequence substantially identical (e.g., at least 85%, 90%, 92%, 95%, 97%, 98%, or 99% identical) to SEQ ID NO: 4; and/or a light chain variable region (VL) of the amino acid sequence set forth in SEQ ID NO: 6, or a sequence substantially identical (e.g., at least 85%, 90%, 92%, 95%, 97%, 98%, or 99% identical) to SEQ ID NO: 6.

In certain embodiments, the one or more isolated nucleic acid molecules encode an anti-CD47 antibody molecule comprising: a heavy chain of the amino acid sequence set forth in SEQ ID NO: 15, or a sequence substantially identical (e.g., at least 85%, 90%, 92%, 95%, 97%, 98%, or 99% identical) to SEQ ID NO: 15; and/or a light chain of the amino acid sequence set forth in SEQ ID NO: 16, or a sequence substantially identical (e.g., at least 85%, 90%, 92%, 95%, 97%, 98%, or 99% identical) to SEQ ID NO: 16.

In certain embodiments, the one or more isolated nucleic acid molecules encode an anti-CD47 antibody molecule comprising: a heavy chain variable region (VH) of the amino acid sequence set forth in SEQ ID NO: 4, or a sequence substantially identical (e.g., at least 85%, 90%, 92%, 95%, 97%, 98%, or 99% identical) to SEQ ID NO: 4; and/or a light chain variable region (VL) of the amino acid sequence set forth in SEQ ID NO: 6, or a sequence substantially identical (e.g., at least 85%, 90%, 92%, 95%, 97%, 98%, or 99% identical) to SEQ ID NO: 6.

In another aspect, the invention provides a vector comprising a nucleic acid molecule described herein (e.g., one or more isolated nucleic acid molecules encoding an anti-CD47 antibody molecule comprising a nucleic acid sequence encoding a heavy chain complementarity determining region 1 (HC CDR1) of the amino acid sequence set forth in SEQ ID NO: 7, a heavy chain complementarity determining region 2 (HC CDR2) of the amino acid sequence set forth in SEQ ID NO: 8, a heavy chain complementarity determining region 3 (HC CDR3) of the amino acid sequence set forth in SEQ ID NO: 9, and/or a light chain complementarity determining region 1 (LC CDR1) of the amino acid sequence set forth in SEQ ID NO: 10, a light chain complementarity determining region 2 (LC CDR2) of the amino acid sequence set forth in SEQ ID NO: 11, and a light chain complementarity determining region 3 (LC CDR3) of the amino acid sequence set forth in SEQ ID NO: 12).

In another aspect, the invention provides cells comprising one or more vectors described herein (e.g., vectors comprising a nucleic acid molecule described herein (e.g., one or more isolated nucleic acid molecules encoding an anti-CD47 antibody molecule, comprising a nucleic acid sequence encoding a heavy chain complementarity determining region 1 (HC CDR1) of the amino acid sequence set forth in SEQ ID NO: 7, a heavy chain complementarity determining region 2 (HC CDR2) of the amino acid sequence set forth in SEQ ID NO: 8, a heavy chain complementarity determining region 3 (HC CDR3) of the amino acid sequence set forth in SEQ ID NO: 9, and/or a light chain complementarity determining region 1 (LC CDR1) of the amino acid sequence set forth in SEQ ID NO: 10, a light chain complementarity determining region 2 (LC CDR2) of the amino acid sequence set forth in SEQ ID NO: 11, and a light chain complementarity determining region 3 (LC CDR3) of the amino acid sequence set forth in SEQ ID NO: 12)).

BRIEF DESCRIPTION OF THE FIGURES

FIG. 4A-B is a fluorescence activated cell sorting (FACS) dot plot depicting the level of phagocytosed target cells in the presence of control antibody polyclonal hIgG (FIG. 4A) or the anti-CD47 antibody 2.3D11 (FIG. 4B). Events shown are gated on CD14 and doublets are excluded. FIG. 4C is a legend that identifies the sector corresponding to phagocytosed targets in FIG. 4A and FIG. 4B.

FIGS. 9A and 9B are bar charts depicting the percent of macrophages that have phagocytosed human red blood cells (FIG. 9A) and cyno red blood cells (FIG. 9B) in the presence of each of the indicated anti-CD47 antibodies or control.

FIG. 10A shows the anti-tumor effects of the anti-CD47 antibodies in the Raji lymphoma xenograft model. Isotype control (filled circles) 2.3D11 IgG4mt (open diamonds) and 2.3D11 IgG4 (filled triangles) were dosed at 200 µg per mouse, t.i.w. for 3 weeks. Tumor volume measurement are presented as means+/−SEM (n=10). FIG. 10B shows the anti-tumor effects of 2.3D11 IgG4mt in combination with rituximab in the Raji lymphoma xenograft model. Isotype control (filled circles) and 2.3D11 IgG4mt (open diamonds) were dosed at 200 µg t.i.w., rituximab (open circles) was dosed at 5 mg/kg q.w. and the 2.3D11 IgG4mt/rituximab combination (open squares) was dosed at 200 µg t.i.w. and 5 mg/kg q.w., respectively; all antibodies were dosed for three weeks. Tumor volume measurements are presented as mean+/−SEM (n=8). FIG. 10C shows the anti-tumor effects of 2.3D11 IgG4 in combination with rituximab in the Raji lymphoma xenograft model. Isotype control (filled circles) and 2.3D11 IgG4 (filled triangles) were dosed at 100 µg t.i.w., rituximab (open circles) was dosed at 5 mg/kg q.w. and the 2.3D11 IgG4/rituximab combination (open squares) was dosed at 100 µg t.i.w. and 5 mg/kg q.w., respectively; all antibodies were dosed for three weeks. Tumor volume measurements are presented as mean+/−SEM (n=8).

FIGS. 12A-12D are bar graphs showing the percent of CD14+ cells that were CFSE+ in a phagocytosis assay with polarized macrophages. Primary human monocytes were differentiated in media containing 100 ng/mL recombinant human macrophage colony-stimulating factor (M-CSF) for 6 days. On the sixth day, macrophages were replated in the presence of either M-CSF alone (FIG. 12A), M-CSF plus interleukin-10 (IL-10), transforming growth factor β (TGFβ) and interleukin-4 (IL-4) (FIG. 12B), M-CSF plus interferon γ and lipopolysaccharide (LPS) (FIG. 12C), or M-CSF plus Dexamethasone (FIG. 12D) overnight. Phagocytosis assays were performed on day 7, as described in Example 4, using CFSE-labeled Jurkat cells as targets. Antibody concentrations used are indicated by: open bars, 0.08 µg/mL; lined bars, 0.4 µg/mL; hatched bars, 2 µg/mL.

DETAILED DESCRIPTION OF THE INVENTION

Figure 1:
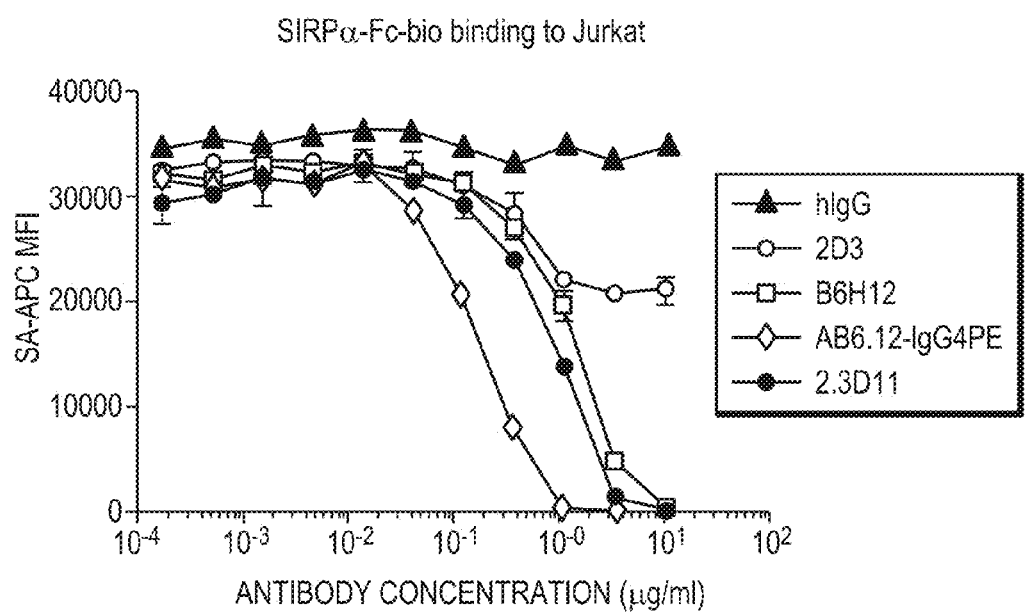
FIG. 1 is a line graph depicting the binding of a biotinylated fusion protein of SIRPα (SIRPα-Fc-bio) to Jurkat cells in the presence of certain antibodies including the anti-CD47 antibodies 2D3, B6H12, AB6.12-IgG4PE, and 2.3D11, and a hIgG control.

The invention relates to antibody molecules that specifically bind CD47, including human CD47, and modulate, e.g., block, inhibit, reduce, antagonize, neutralize or otherwise interfere with the interaction between CD47 and signal regulatory protein α (SIRPα), without causing significant aggregation of cells, for example, hemagglutination of erythrocytes. Many other CD47 antibodies, e.g., B6H12, MABL, BRIC126, and CC2C6, have been reported to cause hemagglutination of human erythrocytes (e.g., U.S. Pat. No. 9,045,541, Uno S, Kinoshita Y, Azuma Y et al. (2007) ONCOL. REP. 17: 1189-94; Kikuchi Y, Uno S, Yoshimura Y et al. (2004) BIOCHEM. BIOPHYS. RES. COMMUN. 315: 912-8). The aggregation of cells represents an important limitation of many therapeutic anti-CD47 antibodies. The anti-CD47 antibody molecules of the present disclosure, including the 2.3D11 antibody molecule, avoid the undesirable effects of agglutination, for example hemagglutination, thereby increasing the efficacy of therapeutically targeting CD47, while maintaining the ability to block the interaction of CD47 with SIRPα, thereby promoting phagocytosis of cells expressing CD47. It has also been discovered that the 2.3D11 antibody unexpectedly cross competes with the anti-CD47 antibody B6H12 for binding to CD47, even though, unlike B6H12, 2.3D11 does not induce hemagglutination or red blood cell phagocytosis.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the present specification. See e.g., Sambrook et al. (1989) MOLECULAR CLONING: A LABORATORY MANUAL (2nd ed., Cold Spring Harbor Laboratory Press, Cold Spring Harbor, N.Y.). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

CD47

CD47, also known as integrin-associated protein (IAP), ovarian cancer antigen OA3, Rh-related antigen and MER6, is a multi-spanning transmembrane receptor belonging to the immunoglobulin superfamily CD47 expression and/or activity has been implicated in a number of diseases and disorders, e.g., cancer. CD47 interacts with SIRPα (signal-regulatory-protein α) on macrophages and thereby inhibits phagocytosis.

An amino acid sequence of an exemplary human CD47 protein is provided in SEQ ID NO: 1 (NCBI Reference Sequence: NP_001768.1). An mRNA sequence encoding an exemplary human CD47 protein is provided in SEQ ID NO: 2 (NCBI Reference Sequence: NM_001777).

Antibody Molecules

As used herein, the term "antibody molecule" refers to a polypeptide or combination of polypeptides that comprise sufficient sequence from an immunoglobulin heavy chain variable region and/or sufficient sequence from an immunoglobulin light chain variable region, to specifically bind to an antigen. The term comprises full length antibodies as well as fragments thereof, e.g., Fab, F(ab') or F(ab')$_2$ fragments. Typically, an antibody molecule comprises heavy chain CDR1, CDR2, and CDR3 and light chain CDR1, CDR2, and CDR3 sequences. Antibody molecules include human, humanized, CDR-grafted antibodies and antigen binding fragments thereof. In certain embodiments, an antibody molecule comprises a protein that comprises at least one immunoglobulin variable region segment, e.g., an amino acid sequence that provides an immunoglobulin variable domain or immunoglobulin variable domain sequence.

The VH or VL chain of the antibody molecule can further include all or part of a heavy or light chain constant region, to thereby form a heavy or light immunoglobulin chain, respectively. The antibody molecule can be a typical tetramer of two heavy immunoglobulin chains and two light immunoglobulin chains where the two heavy chains are linked by optionally at least one disulfide bond and each pair of heavy and light chains are linked by a disulfide bond.

An antibody molecule can comprise one or both of a heavy (or light) chain immunoglobulin variable region segment. As used herein, the term "heavy (or light) chain immunoglobulin variable region segment," refers to an entire heavy (or light) chain immunoglobulin variable region, or a fragment thereof, that is capable of binding antigen. The ability of a heavy or light chain segment to bind antigen is measured with the segment paired with a light or heavy chain, respectively. In certain embodiments, a heavy or light chain segment that is less than a full length variable region will, when paired with the appropriate chain, bind with an affinity that is at least 20, 30, 40, 50, 60, 70, 80, 90, or 95% of what is observed when the full length chain is paired with a light chain or heavy chain, respectively.

An immunoglobulin variable region segment may differ from a reference or consensus sequence. As used herein, to "differ," means that a residue in the reference sequence or consensus sequence is replaced with either a different residue or an absent or inserted residue.

The compositions and methods of the present invention encompass polypeptides and nucleic acids having the sequences specified, or sequences substantially identical or similar thereto, e.g., sequences at least 85%, 90%, 95% identical or higher to a specified sequence. In the context of an amino acid sequence, the term "substantially identical" as used herein refers to a first amino acid sequence that contains a sufficient or minimum number of amino acid residues that are: i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein.

In the context of nucleotide sequence, the term "substantially identical" as used herein refers to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50% or 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) J. MOL. BIOL. 48:444-453) algorithm which has been incorporated into the GAP program in the GCG software package (available on the world wide web at gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available on the world wide web at gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blosum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) J. MOL. BIOL. 215:403-10. BLAST nucleotide searches can be performed with the NBLAST program, score=100, wordlength=12 to obtain nucleotide sequences homologous to a nucleic acid molecule of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (1997) NUCLEIC ACIDS RES. 25:3389-3402. When utilizing BLAST and Gapped BLAST programs, the default parameters of the respective programs (e.g., XBLAST and NBLAST) can be used (available on the world wide web at ncbi.nlm.nih.gov).

It is understood that the molecules of the present invention may have additional conservative or non-essential amino acid substitutions, which do not have a substantial effect on their functions.

An antibody molecule can comprise a heavy (H) chain variable region (abbreviated herein as VH), and a light (L) chain variable region (abbreviated herein as VL). In another example, an antibody comprises two heavy (H) chain variable regions and two light (L) chain variable regions or an antibody binding fragment thereof. The light chains of the immunoglobulin may be of types kappa or lambda. In one embodiment, the antibody molecule is glycosylated. An antibody molecule can be functional for antibody-dependent cellular cytotoxicity and/or complement-mediated cytotoxicity, or may be non-functional for one or both of these activities. An antibody molecule can be an intact antibody or an antigen-binding fragment thereof.

Antibody molecules include "antigen-binding fragments" of a full length antibody, e.g., one or more fragments of a full-length antibody that retain the ability to specifically bind to a target antigen of interest. Examples of antigen binding fragments encompassed within the term "antigen-binding fragment" of a full length antibody include (i) a Fab fragment, a monovalent fragment consisting of the VL, VH, CL and CH1 domains; (ii) a F(ab') or F(ab')$_2$ fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) an scFv consisting of the VL and VH domains of a single arm of an antibody linked together via a polypeptide linker to produce a single chain Fv (scFv), (vi) a dAb fragment (Ward et al. (1989) NATURE 341:544-546), which consists of a VH domain; and (vii) an isolated complementarity determining region (CDR) that retains functionality.

As used herein, an antibody refers to a polypeptide, e.g., a tetrameric or single chain polypeptide, comprising the structural and functional characteristics, particularly the antigen binding characteristics, of an immunoglobulin. Typically, a human antibody comprises two identical light chains and two identical heavy chains. Each chain comprises a variable region.

The variable heavy (VH) and variable light (VL) regions can be further subdivided into regions of hypervariability, termed "complementarity determining regions" ("CDR"), interspersed with regions that are more conserved, termed "framework regions" (FR). Human antibodies have three VH CDRs and three VL CDRs, separated by framework regions FR1-FR4. The extent of the FRs and CDRs has been precisely defined (Kabat, E. A., et al. (1991) SEQUENCES OF PROTEINS OF IMMUNOLOGICAL INTEREST, FIFTH EDITION, U. S. Department of Health and Human Services, NIH Publication No. 91-3242; and Chothia, C. et al. (1987) J. MOL. BIOL. 196:901-917). Each VH and VL is typically composed of three CDRs and four FRs, arranged from amino-terminus to carboxyl-terminus in the following order: FR1, CDR1, FR2, CDR2, FR3, CDR3, and FR4.

The heavy and light immunoglobulin chains can be connected by disulfide bonds. The heavy chain constant region typically comprises three constant domains, CH1, CH2 and CH3. The light chain constant region typically comprises a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has effector function and can fix complement. In other embodiments the antibody does not recruit effector cells or fix complement. In another embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

In one embodiment, the CD47 antibody molecule described herein comprises an IgG4 constant region. In one embodiment, the IgG4 constant region is a wild-type constant region. In another embodiment, the IgG4 constant region comprises a mutation, e.g., one or both of S228P and L235E, e.g., according to EU numbering (Kabat, E. A., et al., supra). In one embodiment, the CD47 antibody molecule described herein comprises an IgG1 constant region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (e.g., EP 388,151 A1, U.S. Pat. No. 5,624,821 and U.S. Pat. No. 5,648,260). Similar types of alterations could be described which if applied to a murine, or other species immunoglobulin would reduce or eliminate these functions.

The term "immunoglobulin" comprises various broad classes of polypeptides that can be distinguished biochemically. Those skilled in the art will appreciate that heavy chains are classified as gamma, mu, alpha, delta, or epsilon ($\gamma$, $\alpha$, $\delta$, $\epsilon$) with some subclasses among them (e.g., $\gamma$1-$\gamma$4). It is the nature of this chain that determines the "class" of the antibody as IgG, IgM, IgA IgD, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes fall within the scope of the present disclosure. Light chains are classified as either kappa or lambda ($\kappa$, $\lambda$). Each heavy chain class may be bound with either a kappa or lambda light chain.

As used herein, the term antibody molecule comprises intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity.

Suitable antibodies include, but are not limited to, monoclonal, monospecific, polyclonal, polyspecific, human antibodies, primatized antibodies, chimeric antibodies, bi-specific antibodies, humanized antibodies, conjugated antibodies (e.g., antibodies conjugated or fused to other proteins, radiolabels, or cytotoxins), Small Modular ImmunoPharmaceuticals ("SMIPs™"), single chain antibodies, cameloid antibodies, and antibody fragments.

In certain embodiments, an antibody molecule is a humanized antibody. A humanized antibody refers to an immunoglobulin comprising a human framework region and one or more CDRs from a non-human, e.g., mouse or rat, immunoglobulin. The immunoglobulin providing the CDRs is often referred to as the "donor" and the human immunoglobulin providing the framework often called the "acceptor," though in embodiments, no source or no process limitation is implied. Typically a humanized antibody comprises a humanized light chain and a humanized heavy chain immunoglobulin.

An "immunoglobulin domain" refers to a domain from the variable or constant domain of immunoglobulin molecules Immunoglobulin domains typically contain two beta-sheets formed of about seven beta-strands, and a conserved disulfide bond (see, e.g., A. F. Williams and A. N. Barclay (1988) ANN. REV. IMMUNOL. 6:381-405).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that comprises an immunoglobulin variable domain sequence can associate with another immunoglobulin variable domain sequence to form a target binding structure (or "antigen binding site"), e.g., a structure that interacts with the target antigen.

The antibody or antibody molecule can be derived from a mammal, e.g., a rodent, e.g., a mouse or rat, horse, pig, or goat. In certain embodiments, an antibody or antibody molecule is produced using a recombinant cell. In certain embodiments, an antibody or antibody molecule is a chimeric antibody, for example, from mouse, rat, horse, pig, or other species, bearing human constant and/or variable regions domains.

Multi-Specific Antibodies

In certain embodiments the antibody molecule is a multi-specific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second, different epitope. In an embodiment, the first and second epitopes are present on the same antigen, e.g., the same protein (or subunit of a multimeric protein). In another embodiment, the first and second epitopes overlap. In an embodiment, the first and second epitopes do not overlap. In an embodiment, the first and second epitopes are on different antigens, e.g., on different proteins (or different subunits of a multimeric protein). In another embodiment, a multi-specific antibody molecule comprises a third, fourth or fifth immunoglobulin variable domain. In an embodiment, a multi-specific antibody molecule is a bispecific antibody molecule, a trispecific antibody molecule, or tetraspecific antibody molecule.

A bispecific antibody is an antibody molecule capable of binding specifically to two antigens. A bispecific antibody molecule is characterized by a first immunoglobulin variable domain sequence which has binding specificity for a first epitope and a second immunoglobulin variable domain sequence that has binding specificity for a second, different epitope. The first and second epitopes can be on the same antigen, e.g., the same protein (or subunit of a multimeric protein). The first and second epitopes may or may not overlap. In certain embodiments, the first and second epitopes are on different antigens, e.g., on different proteins (or different subunits of a multimeric protein). The bispecific antibody molecule may comprise a heavy chain variable domain sequence and a light chain variable domain sequence which together define an antigen binding site with binding specificity for a first epitope and a heavy chain variable domain sequence and a light chain variable domain sequence which together define an antigen binding site with binding specificity for a second epitope. In one embodiment, a bispecific antibody molecule comprises a half antibody having binding specificity for a first epitope and a half antibody having binding specificity for a second epitope. The bispecific antibody molecule may comprises a half antibody, or fragment thereof, containing an antigen binding site having binding specificity for a first epitope and a half antibody, or fragment thereof, containing an antigen binding site having binding specificity for a second, different epitope. In one embodiment, a bispecific antibody molecule comprises a scFv, or fragment thereof, have binding specificity for a first epitope and a scFv, or fragment thereof, have binding specificity for a second, different epitope. In an embodiment, the first epitope is located on CD47 and the second epitope is located on CD19, CD20, CD38, or the HER2/neu receptor.

Anti-CD47 Antibody Molecules

The present invention provides isolated, recombinant and/or synthetic anti-CD47 human, primate, rodent, mammalian, chimeric, humanized and/or CDR-grafted antibodies as well as compositions and encoding nucleic acid molecules comprising at least one polynucleotide encoding at least a portion of one anti-CD47 antibody molecule. The present invention further includes, but is not limited to, methods of making and using such nucleic acids and antibodies including diagnostic and therapeutic compositions, methods and devices.

The terms "isolated protein" or "isolated antibody molecule" referred to herein means a protein or antibody molecule, which by virtue of its origin or source of derivation (1) is not associated with proteins found in nature, (2) is free of other proteins from the same source, (3) is expressed by a cell from a different species, or (4) does not occur in nature.

Exemplary antibody molecules of the invention include the 2.3D11 antibody having a variable heavy chain region (VH) and/or variable light (VL) chain region, heavy chain CDR1, CD2, and CD3, light chain CDR1, CD2, and CDR3, and full heavy and light chains, as shown in the sequences below.

Antibody 2.3D11

As shown in the Examples, it has been discovered that antibody 2.3D11 is a novel antibody that is capable of interrupting the interaction between CD47 and SIRPα without inducing significant hemagglutination of erythrocytes. The sequences of the individual heavy and light chain variable regions of the 2.3D11 antibody, and antibody molecules containing such variable region sequences are described below.

Variable Heavy Chain (VH) with leader sequence:

(SEQ ID NO: 3)
MKHLWFFLLLVAAPRWVLSQVQLQESGPGLVKPSGTLSLTCAVSGVSIRS

INWWNWVRQPPGKGLEWIGEIYHSGSTNYNPSLKSRVTISVDKSKNQFSL

KLNSVTAADTAVYYCARDGGIAVTDYYYYGLDVWGQGTTVTVSS.

Variable Heavy Chain (VH) without leader sequence:

(SEQ ID NO: 4)
QVQLQESGPGLVKPSGTLSLTCAVSGVSIRSINWWNWVRQPPGKGLEWIG

EIYHSGSTNYNPSLKSRVTISVDKSKNQFSLKLNSVTAADTAVYYCARDG

GIAVTDYYYYGLDVWGQGTTVTVSS.

Variable Light Chain (VL) with leader sequence:

(SEQ ID NO: 5)
MEAPAQLLFLLLLWLPDTTGEIVLTQSPATLSLSPGERATLSCRASESVS

SNLAWYQQKPGQAPRLLIYGAFNRATGIPARFSGSGSGTDFTLTISSLEP

EDFAVYYCQQRSDWFTFGGGTKVEIK.

Variable Light Chain (VL) without leader sequence:

(SEQ ID NO: 6)
EIVLTQSPATLSLSPGERATLSCRASESVSSNLAWYQQKPGQAPRLLIYG

AFNRATGIPARFSGSGSGTDFTLTISSLEPEDFAVYYCQQRSDWFTFGGG

TKVEIK.

VH Complementarity Determining Region 1 (VH CDR1):
SINWWN (SEQ ID NO: 7).

VH Complementarity Determining Region 2 (VH CDR2):
EIYHSGSTNYNPSLKS (SEQ ID NO: 8).

VH Complementarity Determining Region 3 (VH CDR3):
DGGIAVTDYYYYGLDV (SEQ ID NO: 9).

VL Complementarity Determining Region 1 (VL CDR1):
RASESVSSNLA (SEQ ID NO: 10).

VL Complementarity Determining Region 2 (VL CDR2):
GAFNRAT (SEQ ID NO: 11).

VL Complementarity Determining Region 3 (VL CDR3):
QQRSDWFT (SEQ ID NO: 12).

Full Heavy Chain Sequence without leader sequence, including an annotation of the framework regions 1-4 (FR1-FR4), complementary determining regions 1-3 (CDR1-CDR3) and constant region (FR1-CDR1-FR2-CDR2-FR3-CDR3-FR4-Constant region):

(SEQ ID NO: 15)
QVQLQESGPGLVKPSGTLSLTCAVSGVSIRSINWWNWVRQPPGKGLEWIG

EIYHSGSTNYNPSLKSRVTISVDKSKNQFSLKLNSVTAADTAVYYCARDG

GIAVTDYYYYGLDVWGQGTTVTVSSAETTAPSVYPLAPGTALKSNSMV

TLGCLVKGYFPEPVTVTWNSGALSSGVHTFPAVLQSGLYTLTSSVT

VPSSTWPSQTVTCNVAHPASSTKVDKKIVPRNCGGDCKPCICTGSE

VSSVFIFPPKPKDVLTITLTPKVTCVVVDISQDDPEVHFSWFVDD

VEVHTAQTRPPEEQFNSTFRSVSELPILHQDWLNGRTFRCKVTSA

AFPSPIEKTISKPEGRTQVPHVYTMSPTKEEMTQNEVSITCMVKG

FYPPDIYVEWQMNGQPQENYKNTPPTMDTDGSYFLYSKLNVKKEK

WQQGNTFTCSVLHEGLHNHHTEKSLSHSPG.

Full Heavy Chain Sequence with leader sequence (Leader sequence-FR1-CDR1-FR2-CDR2-FR3-CDR3-FR4-Constant region):

(SEQ ID NO: 13)
MKHLWFFLLLLVAAPRWVLSQVQLQESGPGLVKPSGTLSLTCAVSGVSIRS

INWWNWVRQPPGKGLEWIGEIYHSGSTNYNPSLKSRVTISVDKSKNQFSL

KLNSVTAADTAVYYCARDGGIAVTDYYYYGLDVWGQGTTVTVSSAETTA

PSVYPLAPGTALKSNSMVTLGCLVKGYFPEPVTVWNSGALSSGVHT

FPAVLQSGLYTLTSSVTVPSSTWPSQTVTCNVAHPASSTKVDKKIV

PRNCGGDCKPCICTGSEVSSVFIFPPKPKDVLTITLTPKVTCVVV

DISQDDPEVHFSWFVDDVEVHTAQTRPPEEQFNSTFRSVSELPILHQ

DWLNGRTFRCKVTSAAFPSPIEKTISKPEGRTQVPHVYTMSPTKEE

MTQNEVSITCMVKGFYPPDIYVEWQMNGQPQENYKNTPPTMDTDGS

YFLYSKLNVKKEKWQQGNTFTCSVLHEGLHNHHTEKSLSHSPG.

Full Light Chain Sequence without leader sequence including an annotation of the framework regions 1-4 (FR1-FR4), complementary determining regions 1-3 (CDR1-CDR3) and constant region (FR1-CDR1-FR2-CDR2-FR3-CDR3-FR4-Constant region):

(SEQ ID NO: 16)
EIVLTQSPATLSLSPGERATLSCRASESVSSNLAWYQQKPGQAPRLLIYG

AFNRATGIPARFSGSGSGTDFTLTISSLEPEDFAVYYCQQRSDWFT**FGGG

TKVEIK**RADAAPTVSIFPPSTEQLATGGASVVCLMNNFYPRDISVKW

KIDGTERRDGVLDSVTDQDSKDSTYSMSSTLSLTKADYESHNLYTCE

VVHKTSSSPVVKSFNRNEC.

Full Light Chain Sequence with leader sequence: (Leader sequence-FR1-CDR1-FR2-CDR2-FR3-CDR3-FR4-Constant region):

(SEQ ID NO: 14)
MEAPAQLLFLLLLWLPDTTGEIVLTQSPATLSLSPGERATLSCRASESVS

SNLAWYQQKPGQAPRLLIYGAFNRAT**GIPARFSGSGSGTDFTLTISSLEP

EDFAVYYCQQRSDWFTFGGGTKVEIK**RADAAPTVSIFPPSTEQLATGG

ASVVCLMNNFYPRDISVKWKIDGTERRDGVLDSVTDQDSKDSTYSM

SSTLSLTKADYESHNLYTCEVVHKTSSSPVVKSFNRNEC.

In certain embodiments, an exemplary antibody of the invention comprises a heavy chain variable domain with complementary determining sequences CDR1-3 corresponding to residues 31-36, 51-66, and 99-114, respectively, of SEQ ID NO: 4. In certain embodiments, an exemplary antibody of the invention comprises a heavy chain variable domain with framework sequences FR1-FR4 corresponding to residues 1-30, 37-50, 67-98, and 115-125, respectively, of SEQ ID NO: 4. In certain embodiments, an exemplary antibody of the invention comprises a light chain variable domain with complementary determining sequences CDR1-3 corresponding to residues 24-34, 50-56, and 89-96, respectively, of SEQ ID NO: 6. In certain embodiments, an exemplary antibody of the invention comprises a light chain variable domain with framework sequences FR1-FR4 corresponding to residues 1-23, 35-49, 57-88, and 97-106, respectively, of SEQ ID NO: 6.

In certain embodiments, it is contemplated that a heavy chain variable region sequence, for example, the VH sequence of SEQ ID NO: 4, may be covalently linked to a variety of heavy chain constant region sequences known in the art. Similarly, it is contemplated that a light chain variable region sequence, for example, the VL of SEQ ID NO: 6, maybe be covalently linked to a variety of light chain constant region sequences known in the art. For example, the heavy chain variable region sequence may be used with a heavy chain constant region sequence derived from an IgG1, IgG2, IgG3, or IgG4 molecule.

In certain embodiments, the constant region of the heavy chain of the antibody is of human IgG1 isotype, having an amino acid sequence:

(SEQ ID NO: 17)
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVF

SCSVMHEALHNHYTQKSLSLSPGK.

In certain embodiments, the human IgG1 constant region is modified at amino acid Asn297 (Boxed) to prevent to glycosylation of the antibody, for example Asn297Ala (N297A). In certain embodiments, the constant region of the antibody is modified at amino acid Leu235 (Boxed) to alter Fc receptor interactions, for example Leu235Glu (L235E) or Leu235Ala (L235A). In certain embodiments, the constant region of the antibody is modified at amino acid Leu234 (Boxed) to alter Fc receptor interactions, e.g., Leu234Ala (L234A). In certain embodiments, the constant region of the antibody is modified at amino acid Glu233 (Boxed), e.g., Glu233Pro (E233P). In some embodiments, the constant region of the antibody is altered at both amino acid 234 and 235, for example Leu234Ala and Leu235Ala (L234A/L235A). In certain embodiments, the constant region of the antibody is altered at amino acids 233, 234, and 234, for example, Glu233Pro, Leu234Ala, and Leu235Ala (E233P L234A/L235A) (Armour K L. et al. (1999) EUR. J. IMMUNOL. 29(8):2613-24). All residue numbers are according to EU numbering (Kabat, E. A., et al., supra).

In certain embodiments, the constant region of the heavy chain of the antibody is of human IgG2 isotype, having an amino acid sequence:

(SEQ ID NO: 18)
ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSD

ISVEWESNGQPENNYKTTPPMLDSDGSFFLYSKLTVDKSRWQQGNVFSCSV

MHEALHNHYTQKSLSLSPGK.

In certain embodiments, the human IgG2 constant region is modified at amino acid Asn297 (Boxed) to prevent to glycosylation of the antibody, e.g., Asn297Ala (N297A), where the residue numbers are according to EU numbering (Kabat, E. A., et al., supra).

hl certain embodiments, the constant region of the heavy chain of the antibody is of human IgG3 isotype, having an amino acid sequence:

(SEQ ID NO: 19)
ASTKGPSVFPLAPCSRSTSGGTAALGCLVKDYFPEPVTVSWNSGALTSGVH

TFPAVLQSSGLYSLSSVVTVPSSSLGTQTYTCNVNHKPSNTKVDKRVELKT

PLGDTTHTCPRCPEPKSCDTPPPCPRCPEPKSCDTPPPCPRCPEPKSCDTP

PPCPRCPAPELLGGPSVFLFPPKPKDTLMISRTPEVTCVVVDVSHEDPEVQ

FKWYVDGVEVHNAKTKPREEQYNSTFRVVSVLTVLHQDWLNGKEYKCKVSN

KALPAPIEKTISKTKGQPREPQVYTLPPSREEMTKNQVSLTCLVKGFYPSD

IAVEWESSGQPENNYNTTPPMLDSDGSFFLYSKLTVDKSRWQQGNIFSCSV

MHEALHNRFTQKSLSLSPGK.

In certain embodiments, the human IgG3 constant region is modified at amino acid Asn297 (Boxed) to prevent to glycosylation of the antibody, e.g., Asn297Ala (N297A). In some embodiments, the human IgG3 constant region is modified at amino acid Arg435 (Boxed) to extend the half-life, e.g., Arg435H (R435H). All residue numbers are according to EU numbering (Kabat, E. A., et al., supra).

In certain embodiments, the constant region of the heavy chain of the antibody is of human IgG4 isotype, having an amino acid sequence:

(SEQ ID NO: 20)
ASTKGPSVFPLAPCSRSTSESTAALGCLVKDYFPEPVTVSWNSGALTSGVH

TFPAVLQSSGLYSLSSVVTVPSSSLGTKTYTCNVDHKPSNTKVDKRVESKY

GPPCPSCPAPEFLGGPSVFLFPPKPKDTLMISRTPEVTCVVVDVSQEDPEV

QFNWYVDGVEVHNAKTKPREEQFNSTYRVVSVLTVLHQDWLNGKEYKCKVS

NKGLPSSIEKTISKAKGQPREPQVYTLPPSQEEMTKNQVSLTCLVKGFYPS

DIAVEWESNGQPENNYKTTPPVLDSDGSFFLYSRLTVDKSRWQEGNVFSCS

VMHEALHNHYTQKSLSLSLGK.

In certain embodiments, human IgG4 constant region is modified within the hinge region to prevent or reduce strand exchange, e.g., in some embodiments human IgG4 constant region is modified at Ser228 (Boxed), e.g., Ser228Pro (S228P). In other embodiments, the human IgG4 constant region is modified at amino acid Leu235 (Boxed) to alter Fc receptor interactions, e.g., Leu235Glu (L235E). In some embodiments, the human IgG4 constant region is modified at both Ser228 and Leu335, e.g., Ser228Pro and Leu235Glu (S228P/L235E), and comprises the amino acid sequence of SEQ ID NO: 21. In some embodiments, the human IgG4 constant region is modified at amino acid Asn297 (Boxed) to prevent to glycosylation of the antibody, e.g., Asn297Ala (N297A). All residue numbers are according to EU numbering (Kabat, E. A., et al., supra).

In certain embodiments, the constant region of the heavy chain of the antibody is of human IgM isotype, having an amino acid sequence:

(SEQ ID NO: 33)
GSASAPTLFPLVSCENSPSDTSSVAVGCLAQDFLPDSITLSWKYKNNSDIS

STRGFPSVLRGGKYAATSQVLLPSKDVMQGTDEHVVCKVQHPNGNKEKNVP

LPVIAELPPKVSVFVPPRDGFFGNPRKSKLICQATGFSPRQIQVSWLREGK

QVGSGVTTDQVQAEAKESGPTTYKVTSTLTIKESDWLGQSMFTCRVDHRGL

TFQQNASSMCVPDQDTAIRVFAIPPSFASIFLTKSTKLTCLVTDLTTYDSV

TISWTRQNGEAVKTHTNISESHPNATFSAVGEASICEDDWNSGERFTCTVT

HTDLPSPLKQTISRPKGVALHRPDVYLLPPAREQLNLRESATITCLVTGFS

PADVFVQWMQRGQPLSPEKYVTSAPMPEPQAPGRYFAHSILTVSEEEWNTG

ETYTCVAHEALPNRVTERTVDKSTGKPTLYNVSLVMSDTAGTCY.

In certain embodiments, the human IgG constant region is modified to enhance FcRn binding. Examples of Fc mutations that enhance binding to FcRn are Met252Tyr, Ser254Thr, Thr256Glu (M252Y, S254T, T256E, respectively) (Dall'Acqua et al. (2006) J. BIOL. CHEM. 281(33): 23514-23524), or Met428Leu and Asn434Ser (M428L, N434S) (Zalevsky et al. (2010) NATURE BIOTECH. 28(2): 157-159). All residue numbers are according to EU numbering (Kabat, E. A., et al., supra).

In some embodiments, the human IgG constant region is modified to alter antibody-dependent cellular cytotoxicity (ADCC) and/or complement-dependent cytotoxicity (CDC), e.g., the amino acid modifications described in Natsume et al. (2008) CANCER RES. 68(10): 3863-72; Idusogie et al. (2001) J. IMMUNOL. 166(4): 2571-5; Moore et al. (2010) MABS 2(2): 181-189; Lazar et al. (2006) PROC. NATL. ACAD. SCI. USA 103(11): 4005-4010, Shields et al. (2001) J. BIOL. CHEM. 276(9): 6591-6604; Stavenhagen et al. (2007) CANCER RES. 67(18): 8882-8890; Stavenhagen et al. (2008) ADVAN. ENZYME REGUL. 48: 152-164; Alegre et al. (1992) J. IMMUNOL. 148: 3461-3468.

In some embodiments, the human IgG constant region is modified to induce heterodimerization. For example, a heavy chain having an amino acid modification within the CH3 domain at Thr366, e.g., a substitution with a more bulky amino acid, e.g., Try (T366W), is able to preferentially pair with a second heavy chain having a CH3 domain having amino acid modifications to less bulky amino acids at positions Thr366, Leu368, and Tyr407, e.g., Ser, Ala and Val, respectively (T366S/L368A/Y407V). Heterodimerization via CH3 modifications can be further stabilized by the introduction of a disulfide bond, for example by changing Ser354 to Cys (S354C) and Y349 to Cys (Y349C) on opposite CH3 domains (see, Carter (2001) J. IMMUNOL. METHODS 248: 7-15).

In certain embodiments, the constant region of the light chain of the antibody is a human kappa constant region having an amino acid sequence:

(SEQ ID NO: 22)
TVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFN

RGEC.

In certain embodiments, the constant region of the light chain of the antibody is a human lambda constant region having an amino acid sequence:

(SEQ ID NO: 34)
GQPKANPTVTLFPPSSEELQANKATLVCLISDFYPGAVTVAWKADGSPVKA

GVETTKPSKQSNNKYAASSYLSLTPEQWKSHRSYSCQVTHEGSTVEKTVAP

TEC.

In certain embodiments, an exemplary antibody of the invention comprises a heavy chain variable domain of the 2.3D11 antibody and a human IgG1 heavy chain constant domain depicted as follows (FR1-CDR1-FR2-CDR2-FR3-CDR3-FR4-Constant region; without the leader sequence):

(SEQ ID NO: 23)
QVQLQESGPGLVKPSGTLSLTCAVSGVSIRS̲I̲N̲W̲W̲N̲WVRQPPGKGLEWIG

R̲I̲Y̲H̲S̲G̲S̲T̲N̲Y̲N̲P̲S̲L̲K̲S̲RVTISVDKSKNQFSLKLNSVTAADTAVYYCARD̲G̲

G̲I̲A̲V̲T̲D̲Y̲Y̲Y̲G̲L̲D̲V̲WGQGTTVTVSS*ASTKGPSVPLAPSSKSTSGGTAAL*

*GCLVKDYFPEPVTVSWNSGALTSGVHTFPAVLQSSGLYSLSSVVTV*

*PSSSLGTQTICNVNHKPSNTKVDKKVEPKSCDKTHTCPPCPAPELL*

*GGPSVFLFPPKPKDTLMISRTPEVTCVVVDVSHEDPEVKFNWYVDG*

*VEVHNAKTKPREEQYNSTYRVVSVLTVLHQDWLNGKEYKCKVSNKA*

*LPAPIEKTISKAKGQPREPQVYTLPPSRDELTKNQVSLTCLVKGFYP*

*SDIAVEWESNGQPENNYKTTPPVLDSDGSFFLYSKLTVDKSRWQQGN*

*VFSCSVMHEALHNHYTQKSLSLSPGK.*

In certain embodiments, an exemplary antibody of the invention comprises a heavy chain variable domain of the 2.3D11 antibody and a human IgG4 heavy chain constant domain depicted as follows (FR1-CDR1-FR2-CDR2-FR3-CDR3-FR4-Constant region; without the leader sequence):

(SEQ ID NO: 24)
QVQLQESGPGLVKPSGTLSLTCAVSGVSIRS̲I̲N̲W̲W̲N̲WVRQPPGKGLEWI

G̲R̲I̲Y̲H̲S̲G̲S̲T̲N̲Y̲N̲P̲S̲L̲K̲S̲RVTISVDKSKNQFSLKLNSVTAADTAVYYCAR

D̲G̲G̲I̲A̲V̲T̲D̲Y̲Y̲Y̲G̲L̲D̲V̲WGQGTTVTVSS*ASTKGPSVFPLAPCSRSTSES*

-continued

```
TAALGCLVKDYFPEPVTVSWNSGALTSGVHTFPAVLQSSGLYSLSS

VVTVPSSSLGTKTYTCNVDHKPSNTKVDKRVESKYGPPCPSCPAP

EFLGGPSVFLFPPKPKDTLMISRTPEVTCVVVDVSQEDPEVQFNW

YVDGVEVHNAKTKPREEQFNSTYRVVSVLTVLHQDWLNGKEYKCK

VSNKGLPSSIEKTISKAKGQPREPQVYTLPPSQEEMTKNQVSLTCL

VKGFYPSDIAVEWESNGQPENNYKTTPPVLDSDGSFFLYSRLTVDK

SRWQEGNVFSCSVMHEALHNHYTQSLSLSLGK.
```

In certain embodiments, an exemplary antibody of the invention comprises a heavy chain variable domain of the 2.3D11 antibody and a human IgG4 heavy chain constant domain with Ser228Pro and Leu235Glu substitutions depicted as follows (FR1-CDR1-FR2-CDR2-FR3-CDR3-FR4-Constant region; without the leader sequence, mutated residues boxed):

(SEQ ID NO: 25)
```
QVQLQESGPGLVKPSGTLSLTCAVSGVSIRSINWNWVRQPPGKGLEWI

GEIYHSGSTNYNPSLKSRVTISVDKSKNQFSLKLNSVTAADTAVYYCAR

DGGIAVTDYYYGLDVWGQGTTVTVSSASTKGPSVFPLAPCSRSTSES

TAALGCLVKDYFPEPVTVSWNSGALTSGVHTFPAVLQSSGLYSLSS

VVTVPSSSLGTKTYTCNVDHKPSNTKVDKRVESKYGPPCPPCPAP

EFEGGPSVFLFPPKPKDTLMISRTPEVTCVVVDVSQEDPEVQFNW

YVDGVEVHNAKTKPREEQFNSTYRVVSVLTVLHQDWLNGKEYKCK

VSNKGLPSSIEKTISKAKGQPREPQVYTLPPSQEEMTKNQVSLTCL

VKGFYPSDIAVEWESNGQPENNYKTTPPVLDSDGSFFLYSRLTVD

KSRWQEGNVFSCSVMHEALHNHYTQSLSLSLGK.
```

In certain embodiments, an exemplary antibody of the invention comprises a light chain variable domain of the 2.3D11 antibody and a human kappa constant domain depicted as follows (FR1-CDR1-FR2-CDR2-FR3-CDR3-FR4-Constant region; without the leader sequence):

(SEQ ID NO: 26)
```
EIVLTQSPATLSLSPGERATLSCRASESVSSNLAWYQQKPGQAPRLLIYG

AFNRATGIPARFSGSGSGTDFTLTISSLEPEDFAVYYCQQRSDWPTFGGG

TKVEIKTVAAPSVFIFPPSDEQLKSGTASVVCLLNNFYPREAKVQW

KVDNALQSGNSQESVTEQDSKDSTYSLSSTLTLSKADYEKHKVYACE

VTHQGLSSPVTKSFNRGEC.
```

In certain embodiments, the anti-CD47 antibody molecule comprises one or both of (a) and (b), wherein (a) and (b) are as follows:

(a)(i) light chain CDR1, CDR2 and CDR3, e.g., Chothia or Kabat light chain CDRs, from SEQ ID NO: 16, (a)(ii) light chain CDR1 of SEQ ID NO: 10, light chain CDR2 of SEQ ID NO: 11, and light chain CDR3 of SEQ ID NO: 12, (a)(iii) light chain CDRs CDR1, CDR2 and CDR3, that collectively, differ by no more than 1, 2, 3, 4, 5, or 6 amino acid residues from the light chain CDRs of (a)(i) and (a)(ii);

(a)(iv) a light chain variable region of SEQ ID NO: 6;

(a)(v) an antigen binding fragment of SEQ ID NO: 6;

(a)(vi) an amino acid sequence that differs by no more than 1, 2, 3, 4, 5, 6, 7, 8, 9, or 10, residues from the sequence of (a)(iv) or a)(v);

(a)(vii) an amino acid sequence that is substantially identical (e.g., at least 85%, 90%, 92%, 95%, 97%, 98%, or 99% identical) to the sequence of (a)(iv) or (a)(v); and (b)(i) heavy chain CDR1, CDR2 and CDR3, e.g., Chothia or Kabat heavy chain CDRs, from SEQ ID NO: 15, (b)(ii) heavy chain CDR1 of SEQ ID NO: 7, heavy chain CDR2 of SEQ ID NO: 8, and heavy chain CDR3 of SEQ ID NO: 9, (b)(iii) heavy chain CDRs CDR1, CDR2 and CDR3, that collectively, differ by no more than 1, 2, 3, 4, 5, or 6 amino acid residues from the heavy chain CDRs of (b)(i) and (b)(ii);

(b)(iv) a heavy chain variable region of SEQ ID NO: 4;

(b)(v) an antigen binding fragment of SEQ ID NO: 4;

(b)(vi) an amino acid sequence that differs by no more than 1, 2, 3, 4, 5, 6, 7, 8, 9, or 10, residues from the sequence of (b)(iv) or (b)(v); and (b)(vii) an amino acid sequence that is substantially identical (e.g., at least 85%, 90%, 92%, 95%, 97%, 98%, or 99% identical) to the sequence of (b)(iv) or (b)(v).

In certain configurations, the antibody molecule comprises: (a)(i) and any one of (b); (a)(ii) and any one of (b); (a)(iii) and any one of (b); (a)(iv) and any one of (b); (a)(v) and any one of (b); (a)(vi) and any one of (b); (a)(vii) and any one of (b); (b)(i) and any one of (a); (b)(ii) and any one of (a); (b)(iii) and any one of (a); (b)(iv) and any one of (a); (b)(v) and any one of (a); (b)(vi) and any one of (a); (b)(vii) and any one of (a). In certain configurations, the antibody molecule comprises: (a)(i) and (b)(i); (a)(ii) and (b)(ii); (a)(iii) and (b)(iii); (a)(iv) and (b)(iv); (a)(v) and (b)(v); or (a)(vi) and (b)(vi).

It is contemplated that, with respect to certain of the uses, for example, therapeutic interventions described herein, the anti-CD47 antibody having little or no hemagglutination activity includes one or more of the antibodies described herein, for example, the 2.3D11 antibody and variants thereof, as well as the antibodies known in the art to bind CD47 and disrupt the CD47-SIRPα interaction with little or no hemagglutination activity, including the antibodies described in U.S. Pat. No. 9,045,541, including, for example, the antibodies referred to as 2A1, 2A1-xi, AB6.12, AB6.12-IgG1, AB6.12-IgG4P and AB6.12-IgG4PE. For example antibody AB6.12 comprises the variable heavy chain sequence of SEQ ID NO: 11 and the variable light chain sequence of SEQ ID NO: 42 as set forth in Table 1 of U.S. Pat. No. 9,045,541 (corresponding to SEQ ID NOs. 27 and 28, respectively, as disclosed herein). An additional exemplary antibody is the anti-CD47 antibody, 5F9G4, which comprises a variable heavy chain of SEQ ID NO: 29 and a variable light chain of SEQ ID NO: 30, and is described in Liu et al. (2016) PLoS One 10(9):e0137345.

The antibody molecules described herein may have minor variations in the amino acid sequences compared to a reference, and, for example, may have at least 80%, 90%, 95%, 96%, 97%, 98% or 99% identity relative to a reference sequence, for example, the heavy chain of SEQ ID NO: 15 or the light chain of SEQ ID NO: 16. The mutations may include conservative amino acid substitutions, which are substitutions that take place within a family of amino acids related in their side chains, for example, aspartic acid and glutamic acid.

Antibody molecules of the present invention can be expressed in a modified form. For instance, a region of additional amino acids, particularly charged amino acids, can be added to the N-terminus of an antibody molecule to improve stability and persistence in the host cell, during purification, or during subsequent handling and storage. Also, peptide moieties can be added to an antibody molecule of the present invention to facilitate purification. Such regions can be removed prior to final preparation of an antibody molecule or at least one fragment thereof. Such methods are described in many standard laboratory manuals, such as Sambrook, supra; Ausubel, et al., ed., CURRENT PROTOCOLS IN MOLECULAR BIOLOGY, John Wiley & Sons, Inc., NY, N.Y. (1987-2001).

It is contemplated that the antibodies provided may be used in the generation of anti-idiotype antibodies thereto, as well as compositions comprising an anti-idiotype antibody molecule and encoding nucleic acid molecules comprising at least one polynucleotide encoding at least a portion of an anti-idiotype antibody molecule.

The antibody molecules bind CD47 with an equilibrium binding constant of ≤1 µM, e.g., ≤100 nM, preferably ≤10 nM, and more preferably ≤1 nM, as measured using standard binding assays, for example, the BIACore-based binding assay.

Antibody molecules of the present invention may be characterized relative to a reference anti-CD47 antibody, for example, B6H12, 2D3, MABL, CC2C6, or BRIC126. Antibody B6H12 is described, for example, in U.S. Pat. Nos. 5,057,604 and 9,017,675, is commercially available from Abcam, PLC, Santa Cruz Biotechnology, Inc., and eBioscience, Inc., and comprises a heavy chain variable region of SEQ ID NO: 31 and a light chain variable region of SEQ ID NO: 32. Antibody MABL is described, for example, in Uno S, Kinoshita Y, Azuma Y et al. (2007) ONCOL. REP. 17: 1189-94, and Kikuchi Y, Uno S, Yoshimura Y et al. (2004) BIOCHEM. BIOPHYS. RES. COMMUN. 315: 912-8. Antibody CC2C6 is described, for example, in Martina Seiffert et al. (1997) BLOOD 94(11): 3633-3643, and is commercially available from Santa Cruz Biotechnology, Inc. Antibody BRIC126 is described, for example, in Avent et al. (1988) BIOCHEM. J. 251: 499-505. Antibody 2D3 is commercially available from eBioscience, Inc., and unlike the other reference antibodies does not interfere with the binding between CD47 and SIRPα.

Antibody Molecule Expression

Nucleic acids of the present invention can be expressed in a host cell that contains endogenous DNA encoding an antibody molecule of the present invention. Such methods are well known in the art, e.g., as described in U.S. Pat. Nos. 5,580,734, 5,641,670, 5,733,746, and 5,733,761. Also see, e.g., Sambrook, et al., supra, and Ausubel, et al., supra. Those of ordinary skill in the art are knowledgeable in the numerous expression systems available for expression of a nucleic acid encoding a protein of the present invention. Illustrative of cell cultures useful for the production of the antibody molecules, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, hep G2 cells, P3X63Ag8.653, SP2/0-Ag14, HeLa cells and the like, which are readily available from, for example, American Type Culture Collection, Manassas, Va. Yeast and bacterial host cells may also be used and are well known to those of skill in the art. Other cells useful for production of nucleic acids or proteins of the present invention are known and/or available, for instance, from the American Type Culture Collection Catalogue of Cell Lines and hybridomas or other known or commercial sources.

Expression vectors can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences). See, e.g., Ausubel et al., supra; Sambrook, et al., supra.

Expression vectors optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017), ampicillin, neomycin (G418), mycophenolic acid, or glutamine synthetase (GS, U.S. Pat. Nos. 5,122,464; 5,770,359; and 5,827,739), resistance for eukaryotic cell culture, and tetracycline or ampicillin resistance genes for culturing in E. coli and other bacteria or prokaryotes. Appropriate culture media and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra; Ausubel, supra.

The nucleic acid insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al. (1983) J. VIROL. 45:773-781). Additionally, gene sequences to control replication in the host cell can be incorporated into the vector, as known in the art.

Antibody Molecule Isolation and Purification

Antibody molecules described herein can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography (HPLC) can also be employed for purification. See, e.g., Colligan, Current Protocols in Immunology, or Current Protocols in Protein Science, John Wiley & Sons, New York, N.Y., (1997-2001).

Antibody molecules described herein can include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody molecule of the present invention can be glycosylated or can be non-glycosylated, with glycosylated preferred. Such methods are described in many standard laboratory manuals, such as Sambrook, supra; Ausubel, supra, Colligan, Protein Science, supra.

Nucleic Acid Molecules

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain (e.g., SEQ ID NOs: 7-9) or light chain (e.g., SEQ ID NOs: 10-12); nucleic acid molecules comprising the coding sequence for an anti-CD47 antibody molecule or variable region (e.g., SEQ ID NOs: 4 and 6); and nucleic acid molecules which comprise a nucleotide sequence substantially different from those described above but which, due to the degeneracy of the genetic code, still encode at least one anti-CD47 antibody molecule as described herein and/or as known in the art. Given that the genetic code is well known in the art, it is routine for one skilled in the art to generate such degenerate nucleic acid variants that code for specific anti-CD47 antibody molecules of the present invention. See, e.g., Ausubel, et al., supra, and such nucleic acid variants are included in the present invention. In certain embodiments, a nucleic acid molecule encoding a heavy chain variable domain of the 2.3D11 antibody and a human IgG1 heavy chain constant domain comprises SEQ ID NO: 35. In certain embodiments, a nucleic acid molecule encoding a heavy chain variable domain of the 2.3D11 antibody and a human IgG4 heavy chain constant domain comprises SEQ ID NO: 36. In certain embodiments, a nucleic acid molecule encoding a heavy chain variable domain of the 2.3D11 antibody and a human IgG4 heavy chain constant domain with Ser228Pro and Leu235Glu substitutions comprises SEQ ID NO: 37. In certain embodiments, a nucleic acid molecule encoding a light chain variable domain of the 2.3D11 antibody and a human kappa constant domain comprises SEQ ID NO: 38

As indicated herein, nucleic acid molecules of the present invention which comprise a nucleic acid encoding an anti-CD47 antibody molecule can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody molecule can be fused to a marker sequence, such as a sequence encoding a peptide that facilitates purification of the fused antibody molecule comprising an antibody molecule fragment or portion.

Construction of Nucleic Acids

The isolated nucleic acids of the present invention can be made using (a) recombinant methods, (b) synthetic techniques, (c) purification techniques, or combinations thereof, as well-known in the art. The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention. Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra)

Antibody Molecule Compositions

For therapeutic use, an antibody preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Accordingly, antibody molecule compositions of the present invention can comprise at least one of any suitable excipients, such as, but not limited to, diluent, binder, stabilizer, buffers, salts, lipophilic solvents, preservative, adjuvant or the like. Pharmaceutically acceptable excipients are preferred. Non-limiting examples of, and methods of preparing such sterile solutions are well known in the art, such as, but not limited to, those described in Gennaro, Ed., REMINGTON'S PHARMACEUTICAL SCIENCES, 18th Edition, Mack Publishing Co. (Easton, Pa.) 1990. Pharmaceutically acceptable carriers can be routinely selected that are suitable for the mode of administration, solubility and/or stability of the antibody molecule, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody molecule components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Antibody molecule compositions can also include a buffer or a pH adjusting agent; typically, the buffer is a salt prepared from an organic acid or base. Representative buffers include organic acid salts such as salts of citric acid, acetic acid, ascorbic acid, gluconic acid, carbonic acid, tartaric acid, succinic acid, or phthalic acid; Tris, trometh-amine hydrochloride, or phosphate buffers.

Additionally, antibody molecule compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the antibody molecule compositions according to the invention are known in the art, e.g., as listed in "REMINGTON: THE SCIENCE & PRACTICE OF PHARMACY", 19th ed., Williams & Williams, (1995), and in the "PHYSICIAN'S DESK REFERENCE", 52nd ed., Medical Economics, Montvale, N.J. (1998). Preferred carrier or excipient materials are carbohydrates (e.g., saccharides and alditols) and buffers (e.g., citrate) or polymeric agents.

The present invention provides for stable compositions, comprising at least one anti-CD47 antibody molecule in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, or 1.0%), 0.1-3% benzyl alcohol (e.g., 0.5, 0.9, 1.1, 1.5, 1.9, 2.0, or 2.5%), 0.001-0.5% thimerosal (e.g., 0.005 or 0.01%), 0.001-2.0% phenol (e.g., 0.05, 0.25, 0.28, 0.5, 0.9, or 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, or 1.0%), and the like.

Pharmaceutical compositions containing antibodies disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for monoclonal antibodies is IV infusion. Useful formulations can be prepared by methods known in the pharmaceutical art. For example, see REMINGTON'S PHARMACEUTICAL SCIENCES (1990) supra. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

In certain embodiments, the pharmaceutically acceptable composition comprises the anti-CD47 antibody in 10 mM histidine, 280 mM sucrose, and 0.01% TWEEN 80 at pH 6.0

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The compositions of this invention may be in a variety of forms. These include, for example, liquid, semi-solid and solid dosage forms, such as liquid solutions (e.g., injectable and infusible solutions), dispersions or suspensions, and liposomes. The preferred form depends on the intended mode of administration and therapeutic application. Typical preferred compositions are in the form of injectable or infusible solutions. The preferred mode of administration is parenteral (e.g., intravenous, subcutaneous, intraocular, intraperitoneal, intramuscular). In a preferred embodiment, the preparation is administered by intravenous infusion or injection. In another preferred embodiment, the preparation is administered by intramuscular or subcutaneous injection.

The phrases "parenteral administration" and "administered parenterally" as used herein means modes of administration other than enteral and topical administration, usually by injection, and includes, without limitation, intravenous, intramuscular, subcutaneous, intraarterial, intrathecal, intracapsular, intraorbital, intravitreous, intracardiac, intradermal, intraperitoneal, transtracheal, inhaled, subcutaneous, subcuticular, intraarticular, subcapsular, subarachnoid, intraspinal, epidural and intrasternal injection and infusion.

Articles of Manufacture

The present invention provides an article of manufacture, comprising packaging material and at least one vial comprising a solution of at least one anti-CD47 antibody molecule with the prescribed buffers and/or preservatives, optionally in an aqueous diluent. The aqueous diluent optionally further comprises a pharmaceutically acceptable preservative. Preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4.0 to about pH 10.0, from about pH 5.0 to about pH 9.0, or about pH 6.0 to about pH 8.0.

Other additives, such as a pharmaceutically acceptable solubilizers like TWEEN 20 (polyoxyethylene (20) sorbitan monolaurate), TWEEN 40 (polyoxyethylene (20) sorbitan monopalmitate), TWEEN 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block copolymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

Therapeutic Applications

In addition, the invention provides methods of treating disorders associated with elevated levels of CD47 expression in certain cell types, for example, certain cancers, whose cells exhibit elevated levels of CD47 expression. As a result, the invention provides a method of treating a subject, for example, a subject with a cancer, in need thereof. The method comprises administering an effective amount of an anti-CD47 antibody or a composition comprising an anti-CD47 antibody to the subject in need thereof.

As used herein, the terms "subject" and "patient" refer to organisms to be treated by the methods of the present invention. Such organisms preferably include, but are not limited to, mammals (e.g., murines, simians, equines, bovines, porcines, canines, felines, and the like), and more preferably includes humans. As used herein, the terms, "treat," "treatment" and "treating" includes any effect, e.g., lessening, reducing, modulating, ameliorating or eliminating, that results in the improvement of the condition, disease, disorder, and the like, or ameliorating a symptom thereof.

As used herein, the term "effective amount" refers to the amount of a compound (e.g., an anti-CD47 antibody molecule) sufficient to effect beneficial or desired results. An effective amount can be administered in one or more administrations, applications or dosages and is not intended to be limited to a particular formulation or administration route. Generally, a therapeutically effective amount of active component is in the range of 0.1 mg/kg to 100 mg/kg, e.g., 1 mg/kg to 100 mg/kg, 1 mg/kg to 10 mg/kg. The dosage administered can vary depending upon known factors, such as the pharmacodynamic characteristics of the particular agent, and its mode and route of administration; the age, health, and weight of the recipient; the type and extent of disease or indication to be treated, the nature and extent of symptoms, kind of concurrent treatment, frequency of treatment, and the effect desired. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the antibody, and the disease being treated. Exemplary dosing frequencies are once per day, once per week and once every two weeks. Formulation of monoclonal antibody-based drugs is within ordinary skill in the art. In some embodiments, a monoclonal antibody is lyophilized, and then reconstituted in buffered saline, at the time of administration The present invention provides a method for treating cancer in a cell, tissue, organ, animal or patient. Examples of cancers include, but are not limited to, solid tumors, soft tissue tumors, hematopoietic tumors and metastatic lesions. Examples of hematopoietic tumors include, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodysplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma). In certain embodiments, the solid tumor is NMDA receptor positive teratoma. In certain embodiments, the cancer is chosen from breast cancer, colon cancer, pancreatic cancer (e.g., pancreatic neuroendocrine tumors (PNETs) or pancreatic ductal adenocarcinoma (PDAC)), stomach, uterine cancer, or ovarian cancer.

In one embodiment, the cancer is a cancer associated with ascites. Ascites is a symptom of many types of cancer and can also be caused by a number of conditions, such as advanced liver disease. The types of cancer that are likely to cause ascites are cancer of the breast, lung, large bowel (colon), stomach, pancreas, ovary, womb (endometrium) and the peritoneum. In some embodiments, the cancer associated with ascites is chosen from breast cancer, colon cancer, pancreatic cancer, stomach, uterine cancer, or ovarian cancer. In some embodiments, the cancer is associated with pleural effusions, e.g., lung cancer.

Additional hematological cancers include, Myelodysplastic syndrome (MDS) (e.g., preleukemia, refractory anemias, Ph-negative chronic myelocytic leukemia, chronic myelomonocytic leukemia, myeloid metaplasia), Non-Hodgkin lymphoma (e.g., diffuse large B cell lymphoma, chronic lymphocytic leukemia, mantle cell lymphoma, B lymphoblastic leukemia/lymphoma, peripheral T cell lymphoma and Burkitt's lymphoma), B-lymphoblastic leukemia/lymphoma; B-cell chronic lymphocytic leukemia/small lymphocytic lymphoma; B-cell prolymphocytic leukemia; Lymphoplasmacytic lymphoma; Splenic marginal zone B-cell lymphoma (±villous lymphocytes); Hairy cell leukemia; Plasma cell myeloma/plasmacytoma; Extranodal marginal zone B-cell lymphoma of the MALT type; Nodal marginal zone B-cell lymphoma (±monocytoid B cells); Follicular lymphoma; Mantle cell lymphoma; Diffuse large B-cell lymphomas; Burkitt's lymphoma; Precursor T-lymphoblastic lymphoma/leukemia; T-cell prolymphocytic leukemia; T-cell granular lymphocytic leukemia; Aggressive NK cell leukemia; Adult T-cell lymphoma/leukemia (HTLV 1-positive); Extranodal NK/T-cell lymphoma, nasal type; Enteropathy-type T-cell lymphoma; Hepatosplenic γ-δ T-cell lymphoma; Subcutaneous panniculitis-like T-cell lymphoma; Mycosis fungoides/Sezary syndrome; Anaplastic large cell lymphoma, T/null cell, primary cutaneous type; Anaplastic large cell lymphoma, T-/null-cell, primary systemic type; Peripheral T-cell lymphoma, not otherwise characterized; Angioimmunoblastic T-cell lymphoma, chronic lymphocytic leukemia (CLL), chronic myelocytic leukemia (CML), multiple myeloma, polycythemia vera or myelofibrosis, cutaneous T-cell lymphoma, small lymphocytic lymphoma (SLL), marginal zone lymphoma, CNS lymphoma, immunoblastic large cell lymphoma, and precursor B-lymphoblastic lymphoma.

Anti CD-47 antibodies, including, e.g., the antibody molecules described herein, can also be used to treat disorders associated with cancer, e.g., cancer-induced encephalopathy Anti CD-47 antibodies, including, e.g., the antibody molecules described herein, can also be used to treat inflammatory, autoimmune, fibrotic, fibroproliferative, atopic, or angiogenic disorders. Examples of inflammatory disorders include but are not limited to chronic obstructive pulmonary disease, asthma, rheumatoid arthritis, inflammatory bowel disease (including Crohn's disease and ulcerative colitis), multiple sclerosis, psoriasis, ischemia-reperfusion injuries, septic shock, age-related macular degeneration (e.g., wet age-related macular degeneration), atherosclerosis, Alzheimer's disease, Parkinson's disease, cardiovascular disease, vasculitis, type I and II diabetes, metabolic syndrome, diabetic retinopathy, restenosis. Examples of autoimmune diseases include but are not limited to asthma, rheumatoid arthritis, inflammatory bowel disease, multiple sclerosis, psoriasis, type I diabetes, systemic lupus erythematosus (SLE), Sjögren's syndrome, Hashimoto's thyroiditis, Graves' disease, Guillain-Barré syndrome, autoimmune hepatitis, and Myasthenia gravis. Examples of fibrotic diseases include but are not limited to scleroderma, liver fibrosis, pancreatic fibrosis, chronic obstructive pulmonary disease, diabetic nephropathy, sarcoidosis, idiopathic pulmonary fibrosis, cirrhosis, cystic fibrosis, neurofibromatosis, endometriosis, post-operative fibroids, and restenosis. Examples of atopic disease include but are not limited to atopic dermatitis, atopic asthma, and allergic rhinitis.

The methods and compositions of the invention can be used in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In one embodiment, the methods of the invention include administering to the subject an anti-CD47 molecule, e.g., an anti-CD47 antibody molecule described herein, e.g., a composition or preparation, described herein, in combination with one or more additional therapies, e.g., surgery, radiation therapy, or administration of another therapeutic preparation. In one embodiment, the additional therapy may include chemotherapy, e.g., a cytotoxic agent. In one embodiment the additional therapy may include a targeted therapy, e.g. a tyrosine kinase inhibitor, a proteasome inhibitor, or a protease inhibitor. In one embodiment, the additional therapy may include an anti-inflammatory, anti-angiogenic, anti-fibrotic, or anti-proliferative compound, e.g., a steroid, a biologic immunomodulator, a monoclonal antibody, an antibody fragment, an aptamer, an siRNA, an antisense molecule, a fusion protein, a cytokine, a cytokine receptor, a bronchodialator, a statin, an anti-inflammatory agent (e.g. methotrexate), or an NSAID. In another embodiment, the additional therapy could include combining therapeutics of different classes. The polysaccharide preparation and the additional therapy can be administered simultaneously or sequentially.

Exemplary cytotoxic agents that can be administered in combination with the polysaccharide preparation include antimicrotubule agents, topoisomerase inhibitors, antimetabolites, protein synthesis and degradation inhibitors, mitotic inhibitors, alkylating agents, platinating agents, inhibitors of nucleic acid synthesis, histone deacetylase inhibitors (HDAC inhibitors, e.g., vorinostat (SAHA, MK0683), entinostat (MS-275), panobinostat (LBH589), trichostatin A (TSA), mocetinostat (MGCD0103), belinostat (PXD101), romidepsin (FK228, depsipeptide)), DNA methyltransferase inhibitors, nitrogen mustards, nitrosoureas, ethylenimines, alkyl sulfonates, triazenes, folate analogs, nucleoside analogs, ribonucleotide reductase inhibitors, vinca alkaloids, taxanes, epothilones, intercalating agents, agents capable of interfering with a signal transduction pathway, agents that promote apoptosis and radiation, or antibody molecule conjugates that bind surface proteins to deliver a toxic agent. In one embodiment, the cytotoxic agent that can be administered with a preparation described herein is a platinum-based agent (such as cisplatin), cyclophosphamide, dacarbazine, methotrexate, fluorouracil, gemcitabine, capecitabine, hydroxyurea, topotecan, irinotecan, azacytidine, vorinostat, ixabepilone, bortezomib, taxanes (e.g., paclitaxel or docetaxel), cytochalasin B, gramicidin D, ethidium bromide, emetine, mitomycin, etoposide, tenoposide, vincristine, vinblastine, vinorelbine, colchicin, anthracyclines (e.g., doxorubicin or epirubicin) daunorubicin, dihydroxy anthracin dione, mitoxantrone, mithramycin, actinomycin D, adriamycin, 1-dehydrotestosterone, glucocorticoids, procaine, tetracaine, lidocaine, propranolol, puromycin, ricin, or maytansinoids.

In one embodiment, the methods of the invention include administering to the subject an anti-CD47 antibody molecule, e.g., an anti-CD47 antibody molecule described herein, in combination with an opsonizing antibody.

In embodiments, the opsonizing antibody can facilitate phagocytosis or antibody dependent cellular cytotoxicity (ADCC), or both, of a target cell, e.g., a tumor cell. In one embodiment, the antigen binding portion of the opsonizing antibody binds to a target antigen, whereas the Fc portion of the opsonizing antibody binds to an Fc receptor on a phagocyte. In other embodiments, the antigen binding portion of the opsonizing antibody binds to a target antigen, whereas the Fc portion of the opsonizing antibody binds to an immune effector cell, e.g., via its Fc domain, thus triggering target cell lysis by the bound effector cell (e.g., monocytes, neutrophils and natural killer cells). In one embodiment, the opsonizing antibody can include one or more of an anti-CD19 antibody, an anti-CD20 antibody, an anti-CD38 antibody, an anti-HER2/neu receptor antibody, an anti-EGFR antibody, an anti-CD30 antibody, or an anti-CD33 antibody, either alone or in combination.

The anti-CD47 antibody molecule, e.g., an anti-CD47 antibody molecule described herein, may be administered to the subject in combination with a CD19 inhibitor. The CD19 inhibitor may be an antibody, a fragment or conjugate of an antibody, or a cell therapy. Exemplary anti-CD19 antibodies or fragments or conjugates thereof include but are not limited to blinatumomab, SAR3419 (Sanofi), MEDI-551 (MedImmune LLC), Combotox, DT2219ARL (Masonic Cancer Center), MOR-208 (also called XmAb-5574; MorphoSys), XmAb-5871 (Xencor), MDX-1342 (Bristol-Myers Squibb), SGN-CD19A (Seattle Genetics), and AFM11 (Affimed Therapeutics). In certain embodiments, the anti-CD47 antibody molecule may be administered to the subject in combination with a CD19 inhibitor for the treatment of cancer, e.g., B-cell lymphomas and leukemias, e.g. acute lymphoblastic leukemia.

The anti-CD47 antibody molecule, e.g., an anti-CD47 antibody molecule described herein, may be administered to the subject in combination with a CD20 inhibitor. The CD20 inhibitor may be a small molecule, an antibody, a fragment or conjugate of an antibody, or a cell therapy. Exemplary anti-CD20 antibodies include but are not limited to rituximab, ofatumumab, ocrelizumab, veltuzumab, obinutuzumab, TRU-015 (Trubion Pharmaceuticals), ocaratuzumab, and Pro131921 (Genentech). In certain embodiments, an anti-CD47 antibody molecule may be administered to the subject in combination with a CD20 inhibitor for the treatment of cancer or a disorder associated with cancer, e.g., non-Hodgkin's lymphoma, diffuse large B-cell lymphoma, chronic lymphocytic leukemia, NMDA receptor positive teratoma, or cancer-induced encephalopathy. In certain embodiments, an anti-CD47 antibody molecule may be administered to the subject in combination with a CD20 inhibitor for the treatment of an autoimmune disease, e.g., rheumatoid arthritis or Myasthenia gravis.

The anti-CD47 antibody molecule, e.g., an anti-CD47 antibody molecule described herein, may be administered to the subject in combination with a CD38 inhibitor. The CD38 inhibitor may be a small molecule, an antibody, a fragment or conjugate of an antibody, or a cell therapy. One exemplary anti-CD38 antibody is daratumumab (Johnson & Johnson). In certain embodiments, the anti-CD47 antibody molecule may be administered to the subject in combination with a CD38 inhibitor for the treatment of cancer, e.g. multiple myeloma, B-cell lymphomas, T-cell lymphomas, and leukemias.

The anti-CD47 antibody molecule, e.g., an anti-CD47 antibody molecule described herein, may be administered to the subject in combination with a HER2/neu receptor inhibitor. The anti-HER2/neu receptor inhibitor may be an antibody, a fragment or conjugate of an antibody, or a cell therapy. One exemplary anti-HER2/neu receptor antibody is trastuzumab (Genentech). In certain embodiments, the anti-CD47 antibody molecule may be administered to the subject in combination with an anti-HER2/neu receptor antibody for the treatment of cancer, e.g., breast cancer, gastric cancer, e.g., stomach adenocarcinoma, ovarian cancer, lung adenocarcinoma, uterine cancer, salivary duct carcinomas, testicular germ cell tumors, and esophageal tumors.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing and method steps.

EXAMPLES

Practice of the invention will be more fully understood from the foregoing examples, which are presented herein for illustrative purposes only, and should not be construed as limiting the invention in any way.

Example 1—Generation of Anti-CD47 Antibody Molecules

This example describes the production of anti-CD47 antibodies in mice.

Genetically engineered mice carrying a human immunoglobulin immune repertoire in place of the murine repertoire (Harbour Antibodies BV) were immunized with soluble CD47-Fc fusion protein. Twenty-eight hybridomas expressing anti-CD47 monoclonal antibody molecules were isolated following fusion of splenocytes with a myeloma cell line, screening and cloning. Isolated hybridomas included hybridomas expressing antibody molecules referred to as 2.3D11, 4.2B4, 4.2C11, 4.1H12, 4.12E2, 2.15A5, 2.7B6, 2.12F6, 2.15E4, 2.3A9, 2.5E6, 2.6D3, 4.2C4, 2.3D3, 2.9F9, and 2.1D2. The isolated hybridomas expressed antibody molecules having both heavy and light chains with fully human variable domains and rat constant domains.

Exemplary isolated anti-CD47 antibody 2.3D11 (hereafter referred to as "2.3D11") was sequenced and further characterized below.

The heavy chain of the isolated 2.3D11 antibody has the following sequence (Leader sequence-FR1-CDR1-FR2-CDR2-FR3-CDR3-FR4-Constant region)

(SEQ ID NO: 13)
MKHLWFFLLLVAAPRWVLSQVQLQESGPGLVKPSGTLSLTCAVSGVSIRS

INWWNWVRQPPGKGLEWIGEIYHSGSTNYNPSLKSKLNSVTAADTAVYY

CARDGGIAVTDYYYGLDVWGQGTTVTVSSAETTAPSVYPLAPGTALK

SNSMVTLGCLVKGYFPEPVTVTWNSGALSSGVHTFPAVLQSGLYTL

TSSVTVPSSTWPSQTVTCNVAHPASSTKVDKKIVPRNCGGDCKPCI

CTGSEVSSVFIFPPKPKDVLTITLTPKVTCVVVDISQDDPEVHFSW

FVDDVEVHTAQTRPPEEQFNSTFRSVSELPILHQDWLNGRTFRCKV

TSAAFPSPIEKTISKPEGRTQVPHVYTMSPTKEEMTQNEVSITCMV

KGFYPPDIYVEWQMNGQPQENYKNTPPTMDTDGSYFLYSKLNVKK

EKWQQGNTFTCSVLHEGLHNHHTEKSLSHSPG.

The light chain of the isolated 2.3D11 antibody has the following sequence (Leader sequence-FR1-CDR1-FR2-CDR2-FR3-CDR3-FR4-Constant region):

(SEQ ID NO: 14)
MEAPAQLLFLLLLWLPDTTGEIVLTQSPATLSLSPGERATLSCRASESVS

SNLAWYQQKPGQAPRLLIYGASNRATGIPARFSGSGSGTDFTLTISSLEP

EDFAVYYCQQRSDWPLTFGGGTKVEIKRADAAPTVSIFPPSTEQLATGG

ASVVCLMNNFYPRDISVKWKIDGTERRDGVLDSVTDQDSKDSTYSM

SSTLSLTKADYESHNLYTCEVVHKTSSSPVVKSFNRNEC.

Once isolated, the constant regions of the heavy chain were replaced with heavy chain constant regions from human IgG1 (SEQ ID NO: 17), human IgG4 (SEQ ID NO: 20) or human IgG4 containing Ser228Pro and Leu235Glu substitutions (SEQ ID NO: 21), and the constant region of the light chain was replaced with a human kappa constant region (SEQ ID NO: 22) using conventional recombinant DNA techniques.

The heavy chain of the 2.3D11 antibody comprising a human IgG1 heavy chain constant domain (hereinafter referred to as "2.3D11 IgG1") has the following sequence (FR1-CDR1-FR2-CDR2-FR3-CDR3-FR4-Constant region; without the leader sequence):

(SEQ ID NO: 23)
QVQLQESGPGLVKPSGTLSLTCAVSGVSIRSINWWNWVRQPPGKGLEWIG

EIYHSGSTNYNPSLKSRVTISVDKSKNQFSLKLNSVTAADTAVYYCARDG

GIAVTDYYYGLDVWGQGTTVTVSSASTKGPSVFPLAPSSKSTSGGTAA

LGCLVKDYFPEPVTVSWNSGALTSGVHTFPAVLQSSGLYSLSSVVTV

PSSSLGTQTYICNVNHKPSNTKVDKKVEPKSCDKTHTCPPCPAPE

LLGGPSVFLFPPKPKDTLMISRTPEVTCVVVDVSHEDPEVKFNWYV

DGVEVHNAKTKPREEQYNSTYRVVSVLTVLHQDWLNGKEYKCKVSN

KALPAPIEKTISKAKGQPREPQVYTLPPSRDELTKNQVSLTCLVKGF

YPSDIAVEWESNGQPENNYKTTPPVLDSDGSFFLYSKLTVDKSRWQQ

GNVFSCSVMHEALHNHYTQKSLSLSPGK.

The heavy chain of the 2.3D11 antibody comprising a wild-type human IgG4 heavy chain constant domain (hereinafter referred to as "2.3D11 IgG4") has the following sequence (FR1-CDR1-FR2-CDR2-FR3-CDR3-FR4-Constant region; without leader sequence):

(SEQ ID NO: 24)
QVQLQESGPGLVKPSGTLSLTCAVSGVSIRSINWWNWVRQPPGKGLEWIG

EIYHSGSTNYNPSLKSRVTISVDKSKNQFSLKLNSVTAADTAVYYCARDG

GIAVTDYYYGLDVWGQGTTVTVSSASTKGPSVFPLAPCSRSTSESTAA

LGCLVKDYFPEPVTVSWNSGALTSGVHTFPAVLQSSGLYSLSSVVTV

PSSSLGTKTYTCNVDHKPSNTKVDKRVESKYGPPCPSCPAPEFLG

GPSVFLFPPKPKDTLMISRTPEVTCVVVDVSQEDPEVQFNWYVDGV

EVHNAKTKPREEQFNSTYRVVSVLTVLHQDWLNGKEYKCKVSNKGL

PSSIEKTISKAKGQPREPQVYTLPPSQEEMTKNQVSLTCLVKGFYPS

DIAVEWESNGQPENNYKTTPPVLDSDGSFFLYSRLTVDKSRWQEGN

VFSCSVMHEALHNHYTQKSLSLSLGK.

The heavy chain of the 2.3D11 antibody comprising a mutant human IgG4 heavy chain constant domain with Ser228Pro and Leu235Glt substitutions (hereinafter referred to as "2.3D11 IgG4mt") has the following sequence (FR1-CDR1-FR2-CDR2-FR3-CDR3-FR4-Constant region; without the leader sequence, mutated residues boxed):

(SEQ ID NO: 25)
QVQLQESGPGLVKPSGTLSLTCAVSGVSIRSINWWNWVRQPPGKGLEWIG

EIYHSGSTNYNPSLKSRVTISVDKSKNQFSLKLNSVTAADTAVYYCARDG

GIAVTDYYYGLDVWGQGTTVTVSSASTKGPSVFPLAPCSRSTSESTAA

-continued

LGCLVKDYFPEPVTVSWNSGALTSGVHTFPAVLQSSGLYSLSSVVT

VPSSSLGTKTYTCNVDHKPSNTKVDKRVESKYGPPCPPCPAPEFEG

GPSVFLFPPKPKDTLMISRTPEVTCVVVDVSQEDPEVQFNWYVDGV

EVHNAKTKPREEQFNSTYRVVSVLTVLHQDWLNGKEYKCKVSNKGL

PSSIEKTISKAKGQPREPQVYTLPPSQEEMTKNQVSLTCLVKGFYPS

DIAVEWESNGQPENNYKTTPPVLDSDGSFFLYSRLTVDKSRWQEGN

VFSCSVMHEALHNHYTQKSLSLSLGK.

The light chain of the 2.3D11 antibody comprising a human kappa constant region has the following sequence (FR1-CDR1-FR2-CDR2-FR3-CDR3-FR4-Constant region; without the leader sequence):

(SEQ ID NO: 26)

EIVLTQSPATLSLSPGERATLSCRASESVSSNLAWYQQKPGQAPRLLIYG

AFNRATGIPARFSGSGSGTDFTLTISSLEPEDFAVYYCQQRSDWPTFGGG

TKVEIKTVAAPSVFIFPPSDEQLKSGTASVVCLLNNFYPREAKVQWK

VDNALQSGNSQESVTEQDSKDSTYSLSSTLTLSKADYEKHKVYACEV

THQGLSSPVTKSFNRGEC.

Example 2: In Vitro Characterization of Anti-CD47 Antibodies

The 2.3D11 antibody generated in Example 1 was tested in a set of in vitro assays to ascertain their biological characteristics and activities. The 2.3D11 antibody was found to potently inhibit the interaction between CD47 and SIRPα and enhance phagocytosis of tumor cells. Surprisingly and unexpectedly, 2.3D11 was found to cross compete with reference antibody B6H12 for binding to CD47, even though, unlike B6H12, 2.3D11 does not induce hemagglutination or red blood cell phagocytosis.

I—SIRPα Blocking Activity

SIRPα is a natural ligand of CD47. The ability of 2.3D11 to block the CD47-SIRPα interaction was measured using a flow cytometry based assay, wherein Jurkat cells, which express CD47, were incubated with an anti-CD47 antibody or a control monoclonal antibody (antibodies titrated 10 μg/ml-0.17 ng/ml in 3 fold dilution series), washed and then incubated with SIRPα-Fc-bio (7.5 μg/ml; determined as ~$EC_{70}$ from previous titration). SIRPα bound to the cells was detected using streptavidin-allophycocyanin (SA-APC). As shown in FIG. 1, the 2.3D11 antibody potently blocked the CD47-SIRPα interaction.

II—2.3D11 Competes with B6H12 for Binding to CD47

Figure 2A:
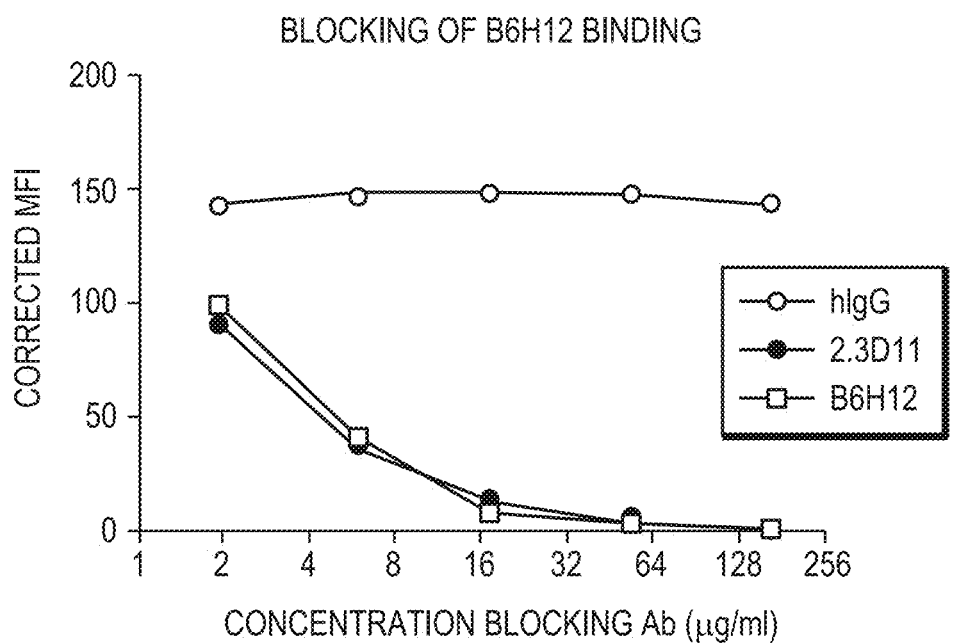
FIG. 2A is a line graph depicting the binding of B6H12-FITC to DU-145 cells pre-incubated with increasing concentrations of unlabeled antibodies 2.3D11, B6H12 or isotype control.
Figure 2B:
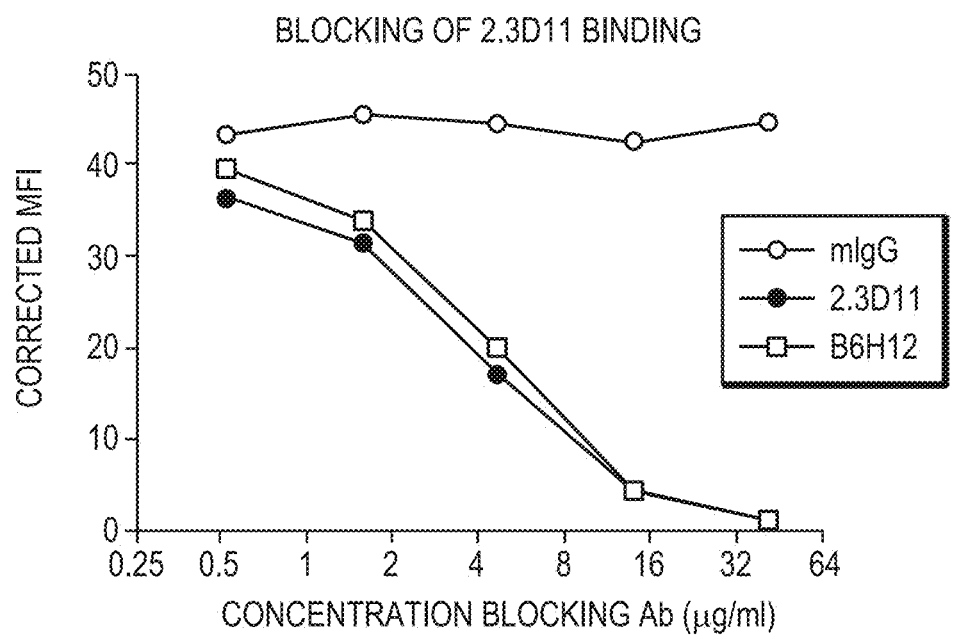
FIG. 2B is a line graph depicting the binding of biotinylated 2.3D11 (2.3D11-bio) to DU-145 cells pre-incubated with increasing concentrations of unlabeled antibodies 2.3D11, B6H12 or isotype control. Binding of 2.3D11-bio was detecting using SA-FITC.
Figure 2C:
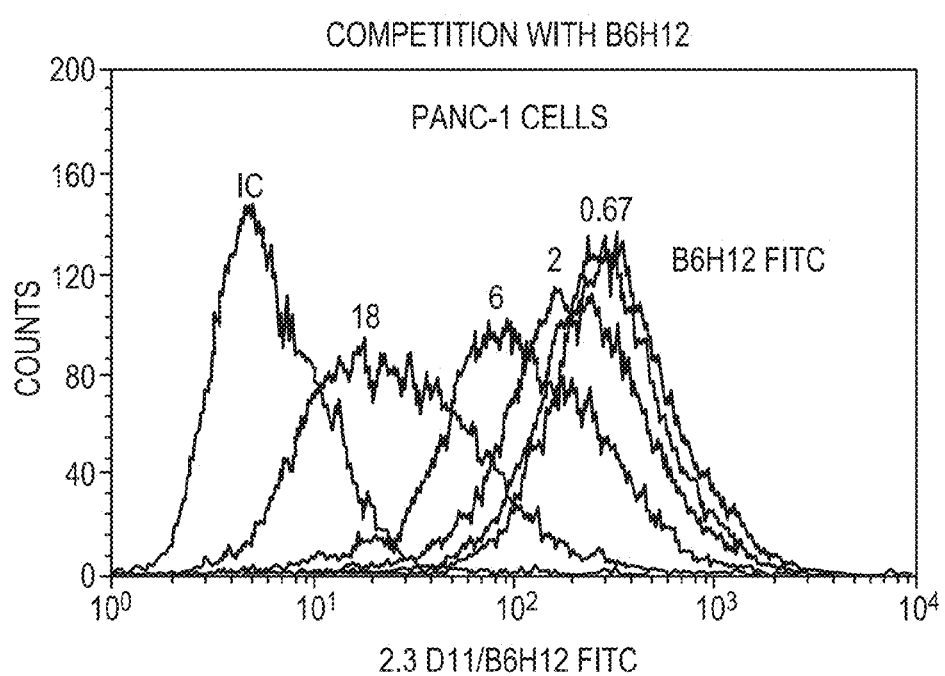
FIG. 2C is a graph depicting the binding of antibody B6H12-FITC (18 µg/ml) to Panc-1 cells, co-incubated with or without unlabeled 2.3D11 antibody at 0.67, 2, 6 or 18 µg/ml. Staining levels are compared to binding of 18 µg/ml of isotype control antibody mouse IgG1-FITC (IC).
Figure 3A:
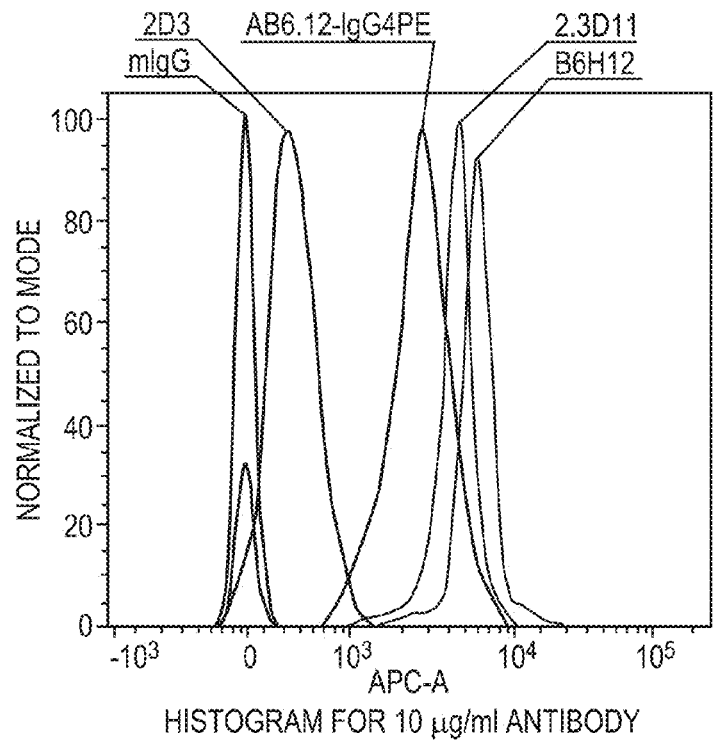
FIG. 3A is a graph depicting the binding of the indicated anti-CD47 antibodies and mIgG1 control to human red blood cells.
Figure 3B:
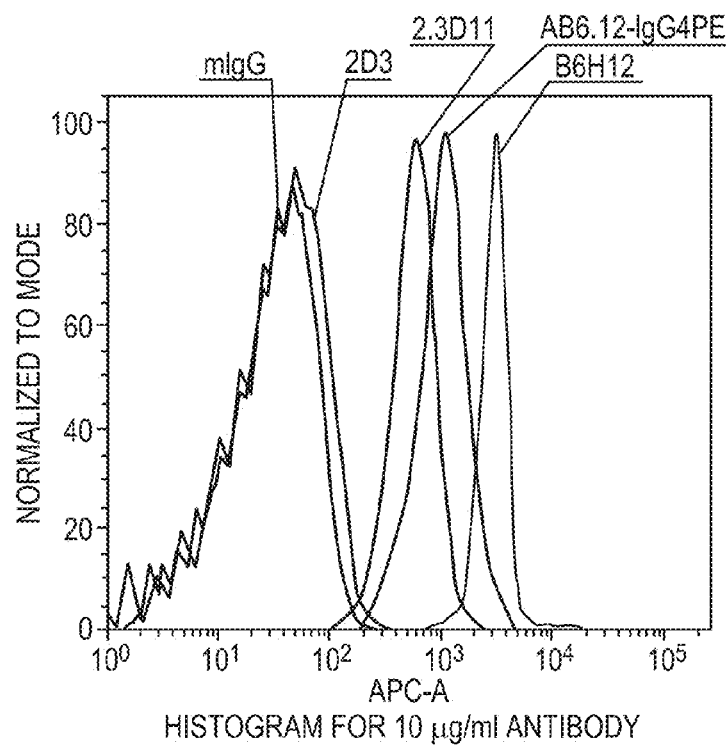
FIG. 3B is a graph depicting the binding of the indicated anti-CD47 antibodies and mIgG1 control to cynomolgus (cyno) red blood cells.
Figure 3C:
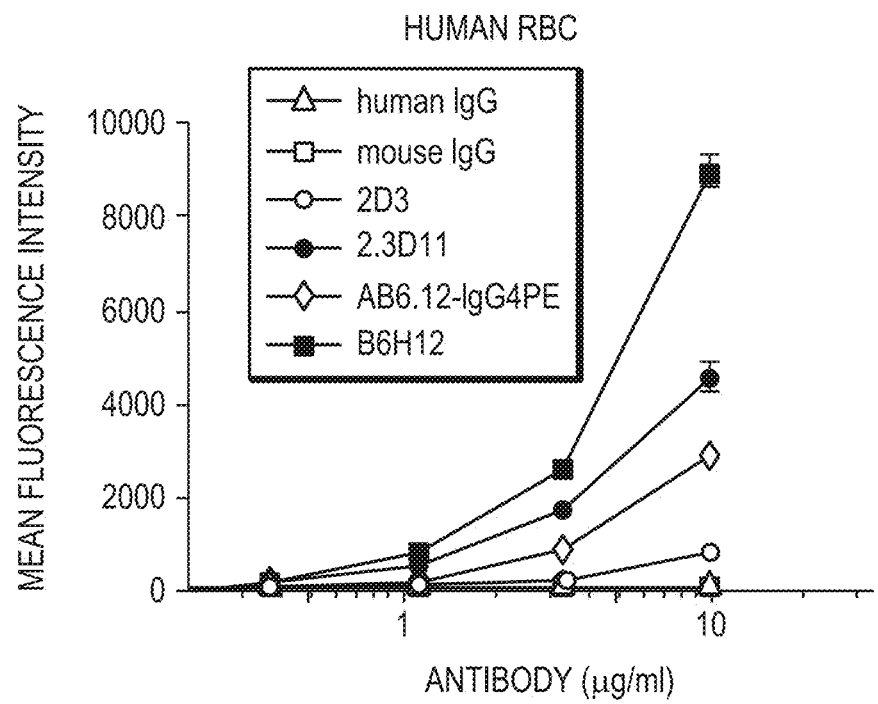
FIG. 3C is a line graph depicting the binding of the indicated anti-CD47 antibodies and mIgG1 control to human red blood cells.
Figure 3D:
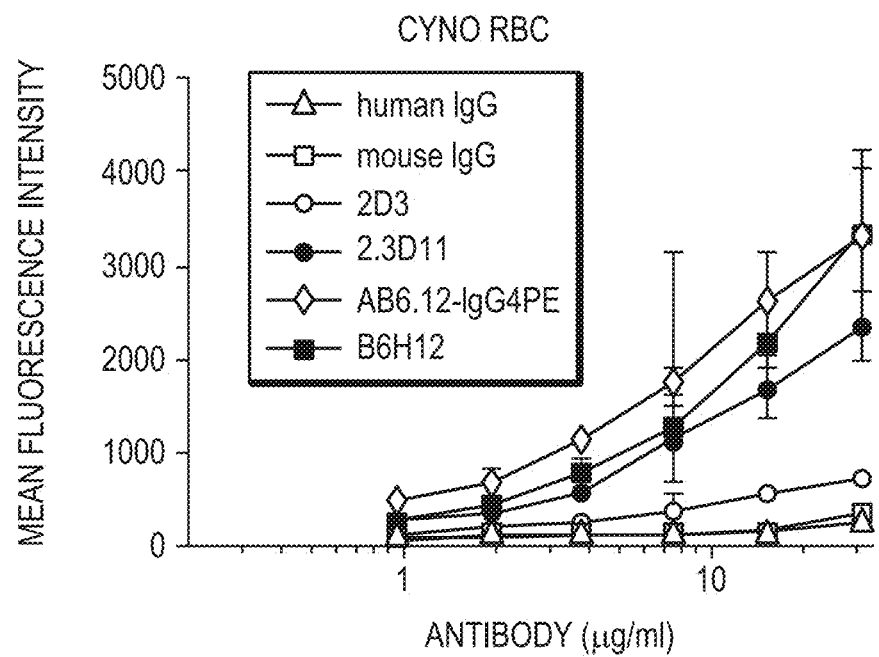
FIG. 3D is a line graph depicting the binding of the indicated anti-CD47 antibodies and mIgG1 control to cyno red blood cells.

As shown in FIGS. 2A-C, the anti-CD47 antibodies B6H12 and 2.3D11 mutually cross compete for (block) binding to CD47, suggesting there is overlap between the binding epitopes of the two antibodies.

Two approaches were used to study their cross competition for CD47.

First, DU-145 (a human prostate cancer cell line that expresses CD47) cells were pre-incubated with varying concentrations of purified anti-CD47 or control antibodies, washed and then stained with biotinylated versions of the antibodies to assess self- and cross-blocking (FIGS. 2A-B). Biotinylated versions of the antibodies were detected with streptavidin fluorescein isothiocyanate (SA-FITC). Second, Panc-1 (pancreatic carcinoma cell line that expresses CD47) cells were co-incubated with B6H12 and increasing concentrations of unlabeled 2.3D11 (FIG. 2C). In both cases, 2.3D11 competed with B6H12 for binding to CD47, which indicates that the two antibodies bind overlapping epitopes.

III—2.3D11 Binding to Cynomolgus Monkey CD47

The ability of 2.3D11 to bind to cynomolgus (cyno) monkey CD47 was assessed. Briefly, human and cyno red blood cells (RBCs) were isolated and reacted with a dilution series of each antibody, and analyzed by flow cytometry. As shown in FIG. 3A-D, 2.3D11 binds to both human and cyno RBCs.

IV—2.3D11 Enhances Phagocytosis of Target Cancer Cells

CD47 is a cell surface receptor that is upregulated on tumor cells and is also thought to contribute to immune evasion through its interaction with its natural ligand SIRPα. Ligation of SIRPα on macrophages by CD47 results in decreased phagocytic activity. The effect of the 2.3D11 antibody on phagocytosis of target cells was assessed.

Figure 5:
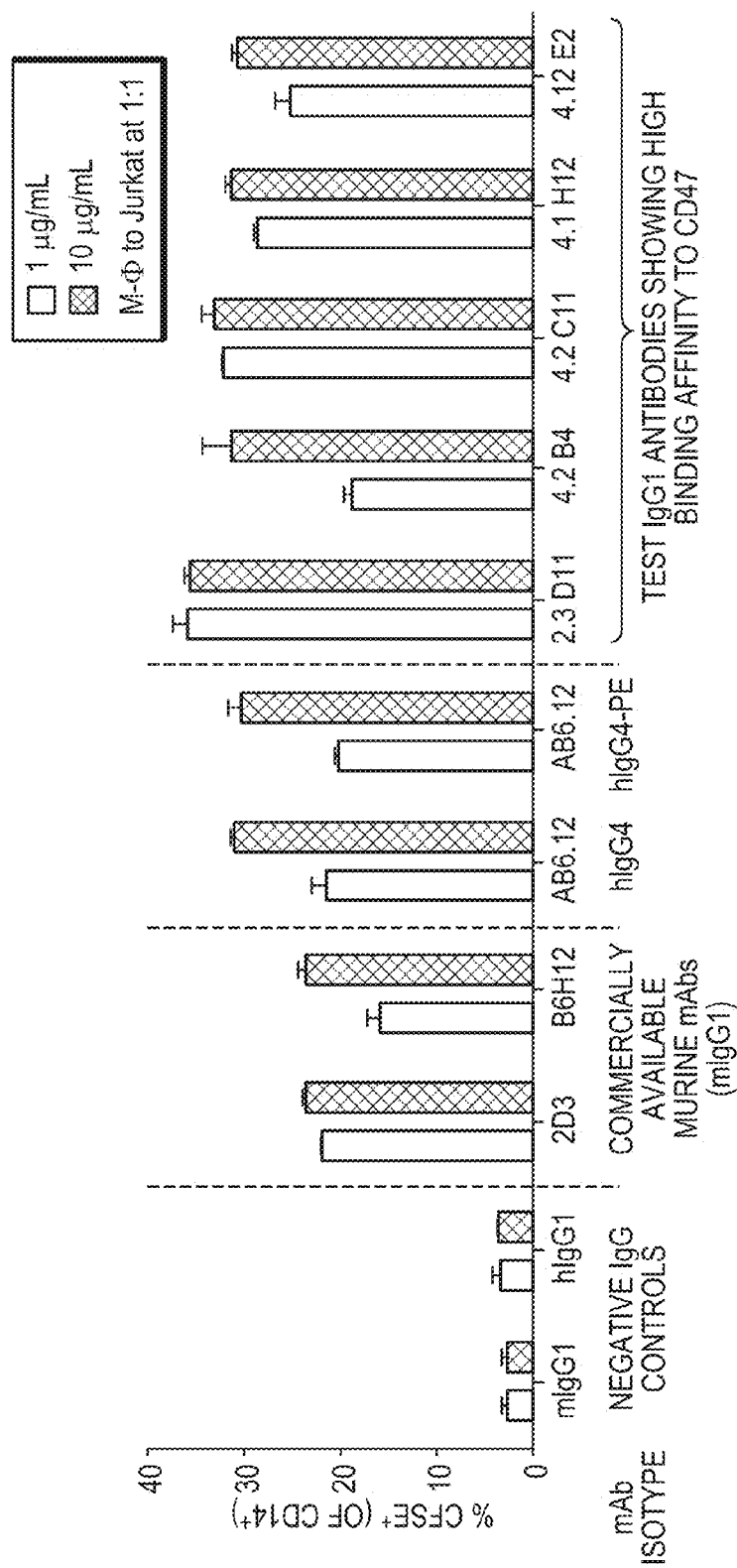
FIG. 5 is a bar chart depicting the percent of macrophages that have phagocytosed target Jurkat cells in the presence of &-control antibodies (monoclonal murine IgG1; mIgG1 or polyclonal human IgG; hIgG) or the indicated anti-CD47 antibody at 1 µg/ml (open bars) or 10 µg/ml (hatched bars).

Briefly, effector cells (primary human macrophages (CD14+ monocytes isolated from human peripheral blood and differentiated with M-CSF for 7 days)), were co-cultured with target cells (carboxyfluorescein succinimidyl ester (CFSE)-labeled Jurkat or Raji cells), at ratios between 1:1 and 1:4 (effector:target), for 2 hours in the presence of anti-CD47 antibodies or isotype control. Phagocytosis was measured as CD14+CFSE+ events as a percent of the total CD14+ cells as measured by flow cytometry. Cytochalasin D, which inhibits phagocytosis, was used as a control. As shown in FIGS. 4A-B and FIG. 5, the presence of 2.3D11 in co-cultures enhanced phagocytosis of target cells.

Figure 6:
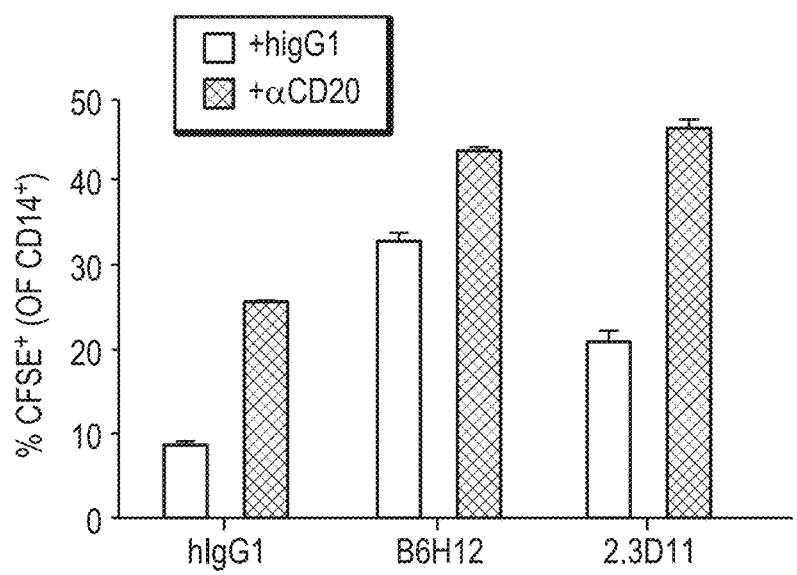
FIG. 6 is a bar chart depicting the percent of macrophages that have phagocytosed Raji target cells in the presence of control antibody (hIgG), B6H12, or 2.3D11 and either a control human IgG antibody or the anti-CD20 antibody rituximab. The anti-CD47 antibodies (B6H12, and 2.3D11) and the anti-CD20 antibodies were used at sub-optimal concentrations (0.3 µg/ml and 0.1 µg/ml, respectively) in order to observe cooperative effects. Isotype control antibody was used at matching concentrations.
Figure 7A:
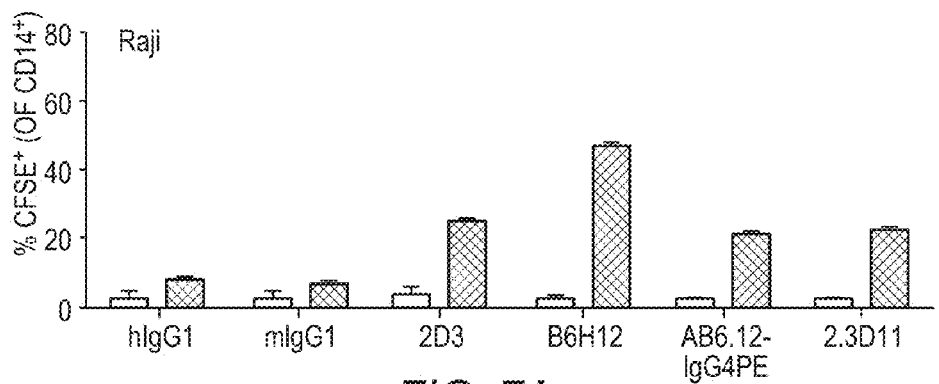
FIG. 7A is a bar chart depicting the percent of macrophages that have phagocytosed target Raji cells in the presence of control antibody or the indicated anti-CD47 antibody.
Figure 7B:
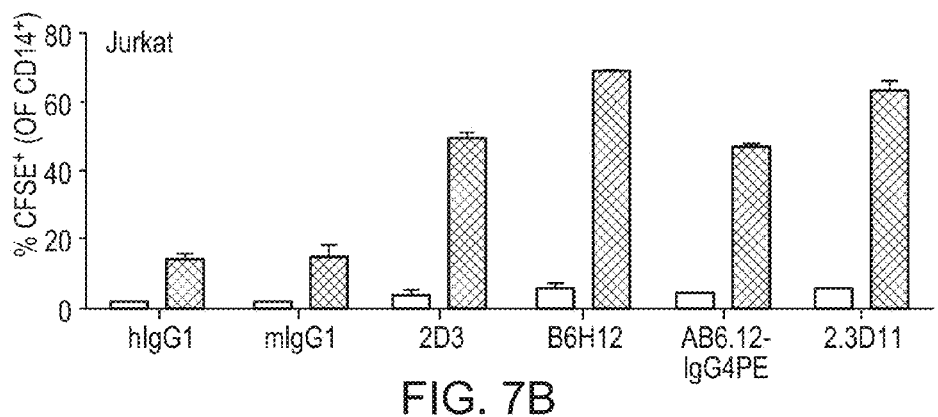
FIG. 7B is a bar chart depicting the percent of macrophages that have phagocytosed Jurkat target cells in the presence of control antibody or the indicated anti-CD47 antibody.
Figure 7C:
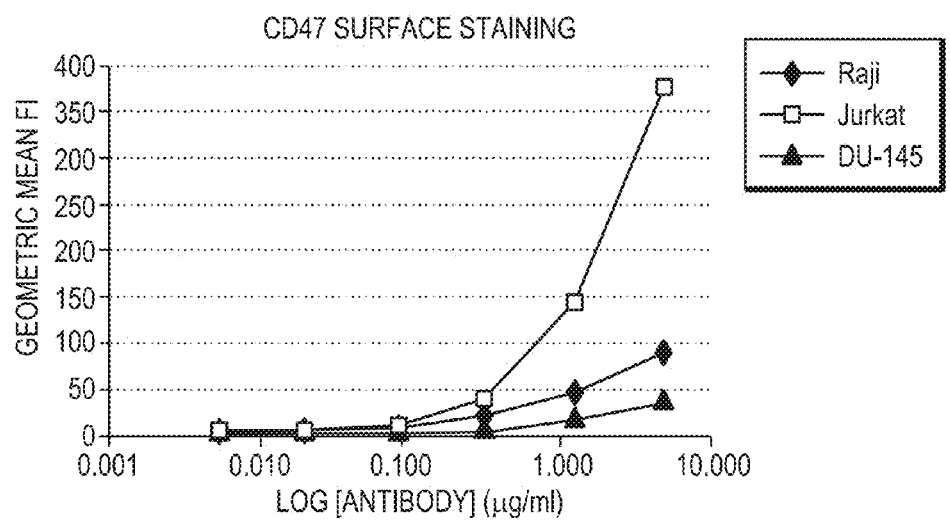
FIG. 7C is a line graph depicting the level of CD47 expression, as determined by 2.3D11 staining, on Raji, Jurkat, and DU-145 cells. Cells were incubated with the indicated concentrations of 2.3D11-bio and staining was detected with SA-FITC.

Further, as shown in FIG. 6, 2.3D11 cooperates with the anti-CD20 antibody rituximab to promote Raji cell phagocytosis. These results suggest that tumor cell phagocytosis can be enhanced in the presence of opsonizing antibodies (e.g., anti-CD20 antibodies) when co-administered with 2.3D11. Additionally, as shown in FIGS. 7A-C, phagocytosis may be influenced by the level of CD47 expression on target cell. 2.3D11 increased phagocytosis of Raji tumor cell line targets with an $EC_{50}$ of ~300 ng/mL (data not shown).

V—Hemagglutination Activity of 2.3D11

To evaluate the hemagglutinating capacity of 2.3D11, human RBCs were incubated with a dose range of anti-CD47 antibody, for example, 2.3D11, 4.2B4, 4.2C11, 4.1H12, 4.12E2, 2D3, B6H12, and AB6.12-IgG4PE, or control in a 96 well plate. Evidence of hemagglutination was demonstrated by the presence of non-settled RBCs, appearing as a haze compared to a punctate dot of non-hemagglutinated RBCs.

Figure 8:
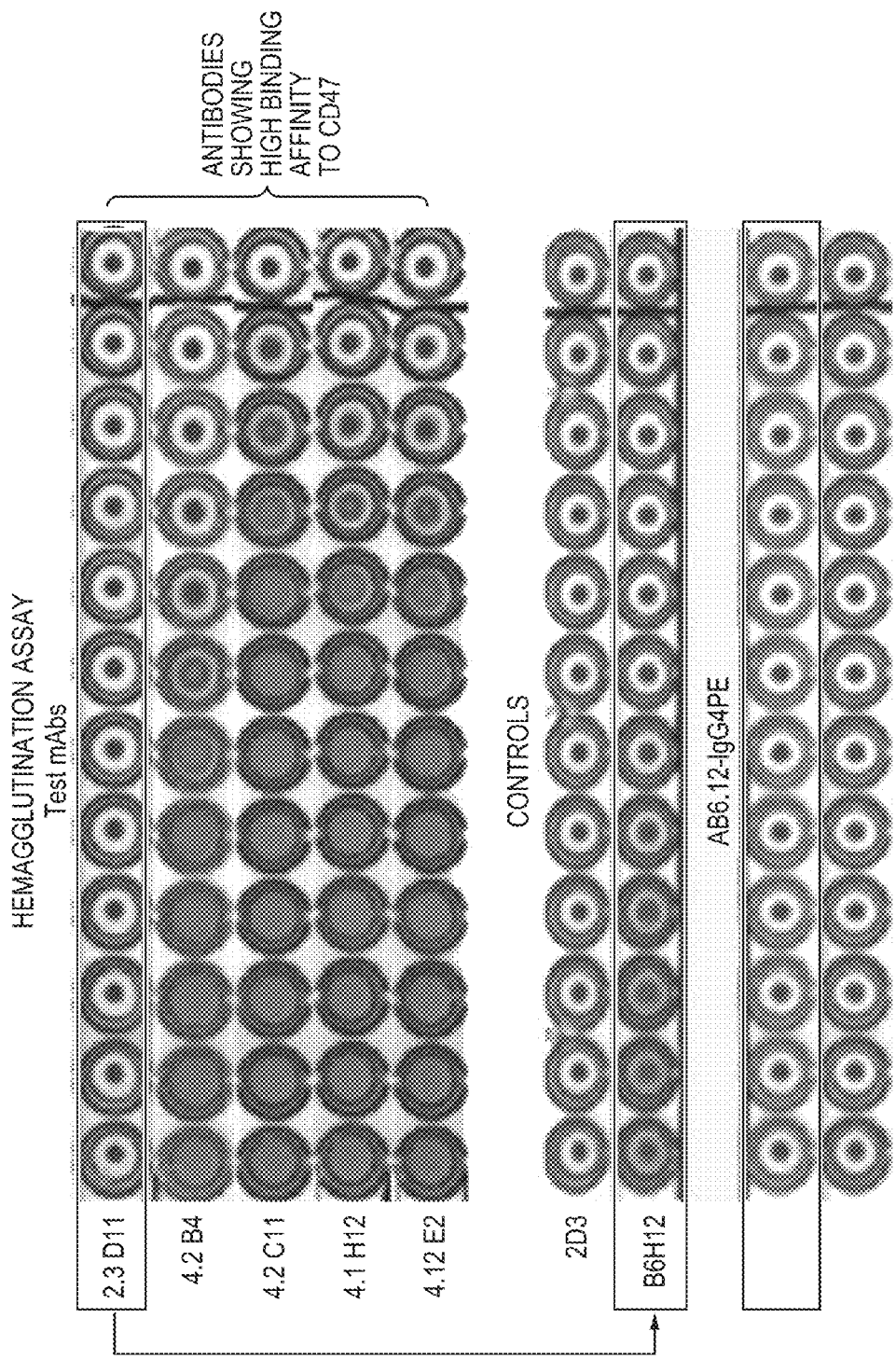
FIG. 8 is a photograph of a 96 well plate depicting the hemagglutination of human red blood cells in the presence of a dose curve for each indicated anti-CD47 antibody or control.

Unexpectedly, as shown in FIG. 8, antibody 2.3D11 did not exhibit hemagglutinating activity at any of the concentrations tested despite binding competition with B6H12 antibody, which is known to cause hemagglutination.

VI—2.3D11 does not Enhance Phagocytosis of Target Red Blood Cells

To evaluate whether binding of 2.3D11 to RBC leads to increased phagocytic uptake by macrophages, phagocytosis assays similar to those described in section IV above were performed, using human or cyno RBC as targets at an effector:target ratio of 1:10. As shown in FIG. 9, 2.3D11 had minimal effect on human and cyno RBC phagocytosis, in contrast to B6H12 which enhanced phagocytosis.

In summary, increased phagocytosis mediated by 2.3D11 is preferential for tumor cells over normal leukocytes and RBC.

Example 3—In Vivo Efficacy of Anti-CD47 Antibody in Tumor Models

The anti-tumor activity of 2.3D11, produced as either a wild-type human IgG4 ("2.3D11 IgG4") or S228P/L235E double mutant human IgG4 ("2.3D11 IgG4mt"), as described in Example 1, was evaluated in the Burkitt's lymphoma Raji xenograft model.

Female CB.17 SCID mice were injected subcutaneously with $1\times10^7$ Raji B tumor cells in 50% Matrigel and treatment was started when tumors reached 100 mm$^3$. Isotype control, 2.3D11 IgG4 and 2.3D11 IgG4mt antibodies were injected intraperitoneally (i.p.) three times per week, for 3 weeks at the indicated doses. Rituximab was injected i.p. at 5 mg/kg once a week for 3 weeks. Body weight and tumor volume were measured twice per week.

Figure 10A:
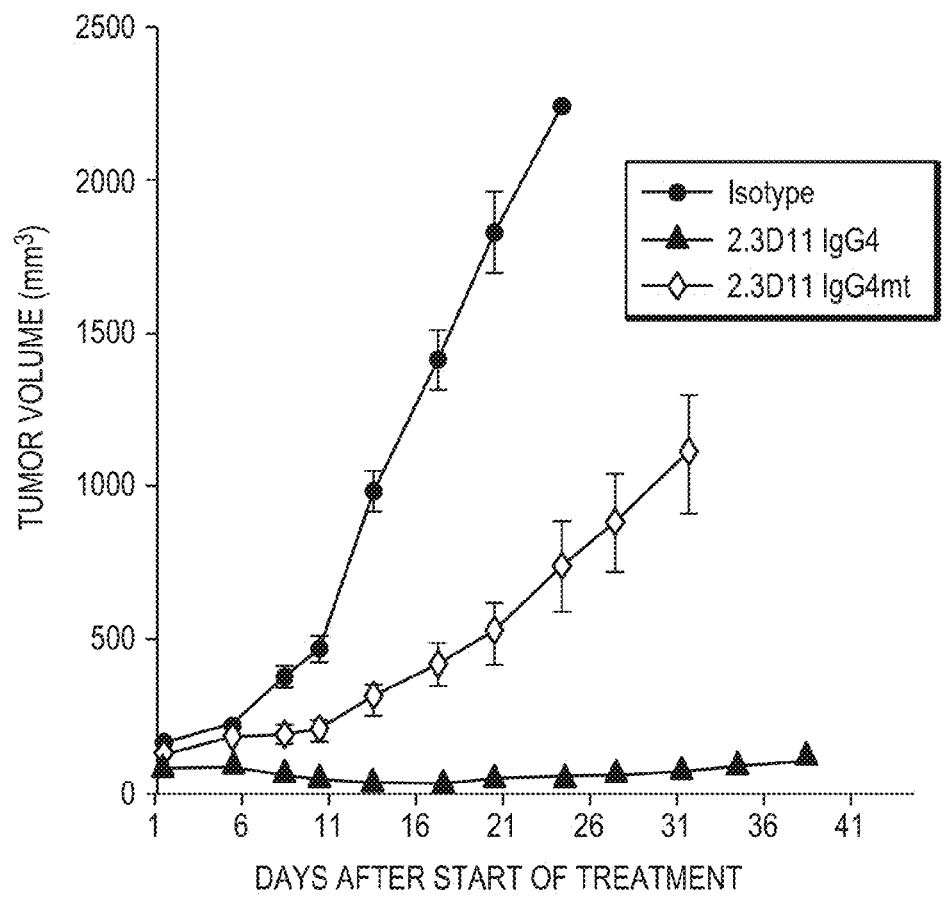
FIGS. 10A-C are line graphs summarizing the effects of the anti-CD47 antibodies 2.3D11 IgG4 or 2.3D11 IgG4mt, alone or in combination with rituximab, in the Raji lymphoma xenograft model.

The antitumor efficacy of 2.3D11 IgG4 and 2.3D11 IgG4mt (200 μg/mouse, t.i.w.) were compared in the Raji model of Burkitt's lymphoma. As shown in FIG. 10A, both the 2.3D11 IgG4 and 2.3D11 IgG4mt antibodies demonstrated anti-tumor activity in this xenograft model. At the time the isotype control group reached 2000 mm$^3$ (day 24), tumor growth inhibition (TGI) activity of the 2.3D11 IgG4 and 2.3D11 IgG4mt antibodies was 97% and 71%, respectively.

In the Raji xenograft model, the anti-tumor activity of 2.3D11 derivatives was at least partially dependent on macrophages, as depletion of macrophages via clodronate administration led to reduced tumor growth inhibition. Tumor-associated macrophage (TAM) numbers and polarization status were also modulated by 2.3D11 derivative treatment (data not shown).

Figure 10B:
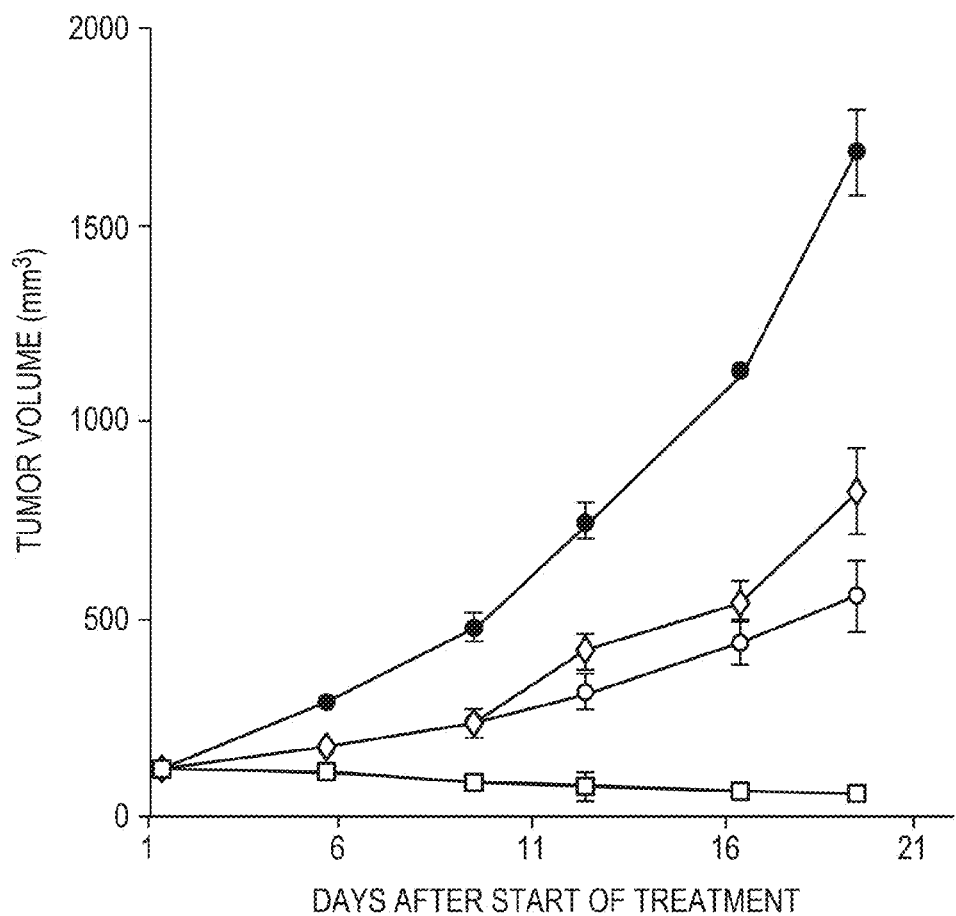
Figure 10C:
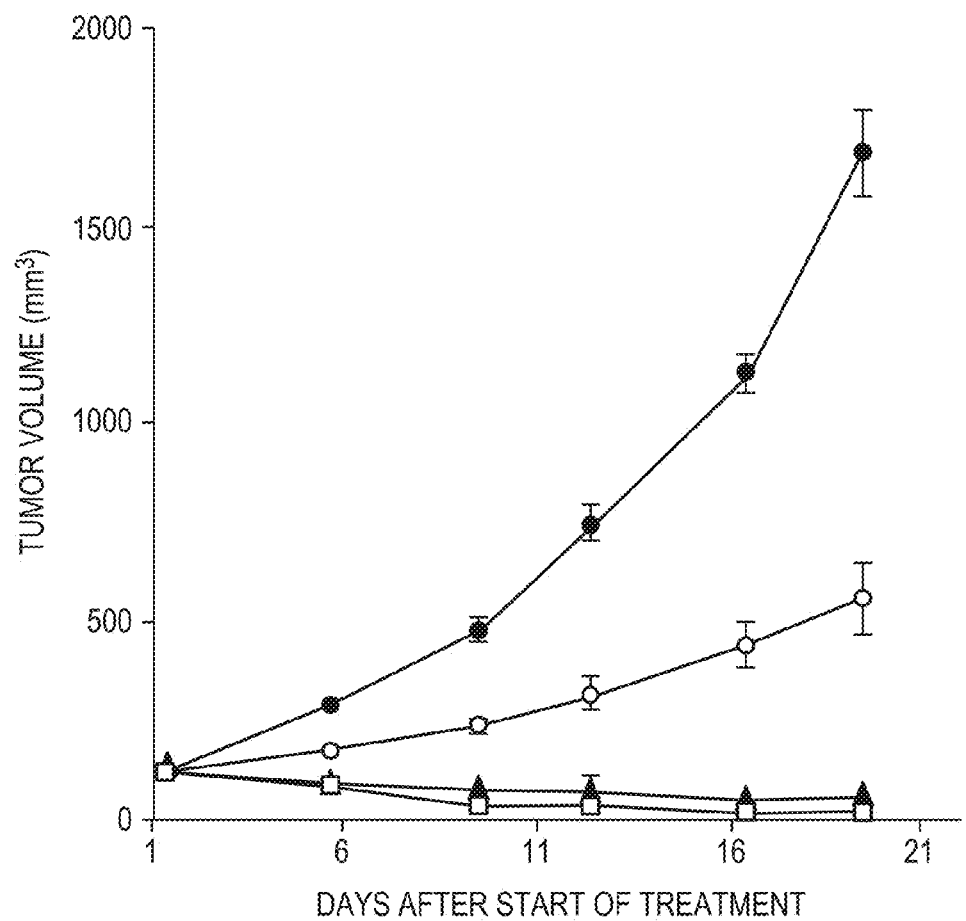

The Raji model has been shown to be sensitive to rituximab, an anti-CD20 antibody used as a first line therapy for diffuse large B-cell lymphoma patients. The antitumor efficacy of 2.3D11 IgG4 (100 μg/mouse, t.i.w.) and 2.3D11 IgG4mt (200 μg/mouse, t.i.w.) in combination with rituximab (5 mg/kg, q.w.) was assessed in the Raji model. The results for 2.3D11 IgG4mt at day 19 after the start of treatment are summarized in FIG. 10B. TGI activity of 2.3D11 IgG4mt antibody alone was 51% and rituximab TGI was 67%. When combined, 2.3D11 IgG4mt and rituximab achieved 96% TGI, indicating synergistic improvement of tumor growth inhibition by the combined antibodies. FIG. 10C summarizes the results for 2.3D11 IgG4 at day 19 after the start of treatment. The data show that 2.3D11 IgG4 is highly potent in a monotherapy setting, leading to tumor regression (from 124 mm$^3$ at the start of treatment to 47 mm$^3$ at day 19) and 96% TGI, similar to the results in the experiment described above but using only half the amount of 2.3D11 IgG4 antibody. The high potency of the 2.3D11 IgG4 makes it difficult to assess the possible additional effect of the combination with rituximab. However, it is noteworthy that at an earlier time point, day 12, the 2.3D11 IgG4 arm had only 1 tumor-free mouse, whereas the combination arm had 5 tumor free mice. In all the experiments described above, no body weight loss was reported.

In summary, 2.3D11 administration led to profound tumor growth inhibition in a model of Burkitt's lymphoma as a single agent and in combination with an opsonizing antibody.

Example 4—Fc Format Variants of Anti-CD47 Antibody

The activity of 2.3D11, produced in three different Fc formats, was evaluated in multiple assays. 2.3D11 was produced with wild-type human IgG4 ("2.3D11 IgG4") or S228P/L235E double mutant human IgG4 ("2.3D11 IgG4mt") or wild type IgG1 ("2.3D11 IgG1").

I—RBC Phagocytosis

Human red blood cells (RBCs) were isolated from healthy donors and labeled with CFSE. Labeled RBCs were cultured with day 7 human macrophages in the presence of a 2.3D11 antibody, isotype control, or anti-CD47 antibody B6H12 for two hours at a target-to-effector ratio of 10:1. After culture, cells were trypsinized and stained with anti-CD14-APC and analyzed by flow cytometry.

Figure 11:
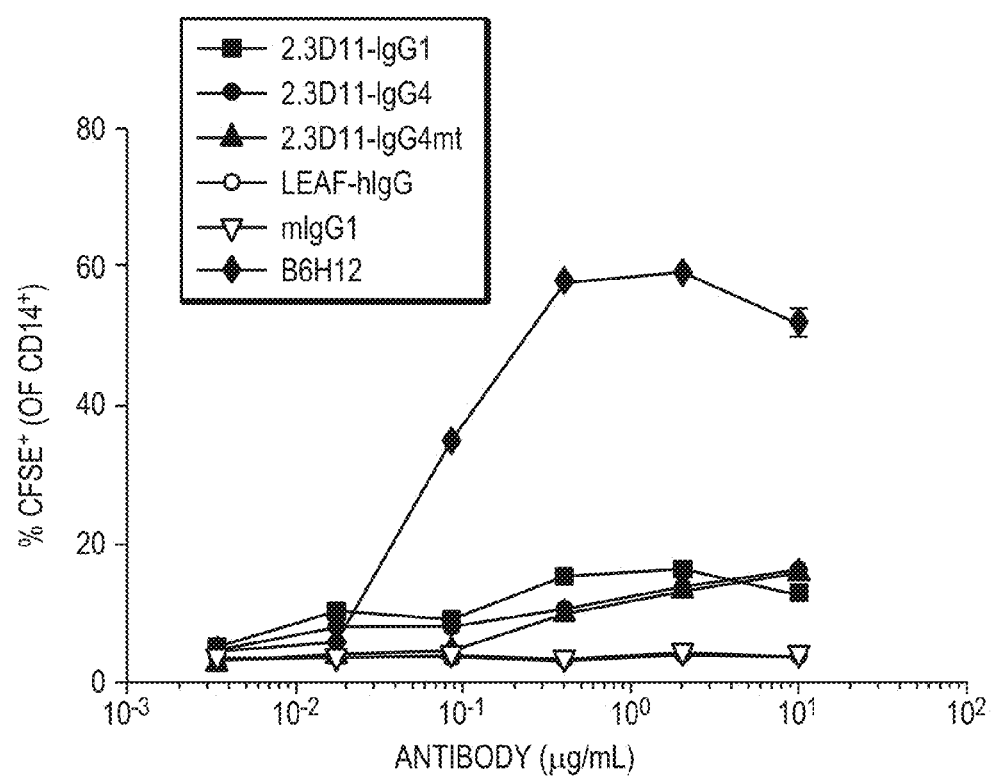
FIG. 11. is a line graph showing the percent of CD14+ cells that were CFSE+ in a red blood cell phagocytosis assay. Human red blood cells were isolated from healthy donors and labeled with CFSE. RBC were cultured with day 7 human macrophages in the phagocytosis assay described in Example 4 at a target-to-effector ratio of 10:1. Representative data from one of three donors shown; filled squares indicates 2.3D11 IgG1, filled circles indicate 2.3D11 IgG4, filled triangles indicate 2.3D11 IgG4mt, open circles indicate human IgG4 isotype control, open triangles indicate murine IgG1 isotype control, and closed diamonds indicate B6H12.

Phagocytosis was quantitated as the percent of CD14+ events (macrophages) that were also CFSE+ and had therefore engulfed a target (events were gated on singlets). No significant difference was observed between the isotype controls or the 2.3D11 IgG1, 2.3D11IgG4 or 2.3D11IgG4mt antibodies, but B6H12 strongly induced RBC phagocytosis. Representative data is shown in FIG. 11.

II—Phagocytosis by Polarized Macrophages

Primary human monocytes were differentiated in 100 ng/mL recombinant human macrophage colony-stimulating factor (M-CSF) for 6 days. On the sixth day, macrophages were replated in the presence of either (A) M-CSF alone, producing unpolarized macrophage, (B) M-CSF plus interleukin-10 (IL-10), transforming growth factor β (TGFβ) and interleukin-4 (IL-4), polarizing the macrophage to the M2 phenotype, (C) M-CSF plus interferon γ and lipopolysaccharide (LPS), polarizing the macrophage to the M1 phenotype, or (D) M-CSF plus dexamethasone (Dex), polarizing the macrophage to a strong M2 phenotype, overnight.

Phagocytosis assays were performed on day 7, as described above, using CFSE-labeled Jurkat cells as targets. The results are summarized in FIGS. 12A-12D, which demonstrate that the anti-CD47 antibody 2.3D11, regardless of Fc format, enhances phagocytosis by both M1 and M2 polarized macrophages.

III—Tumor Cell Phagocytosis

Figure 13:
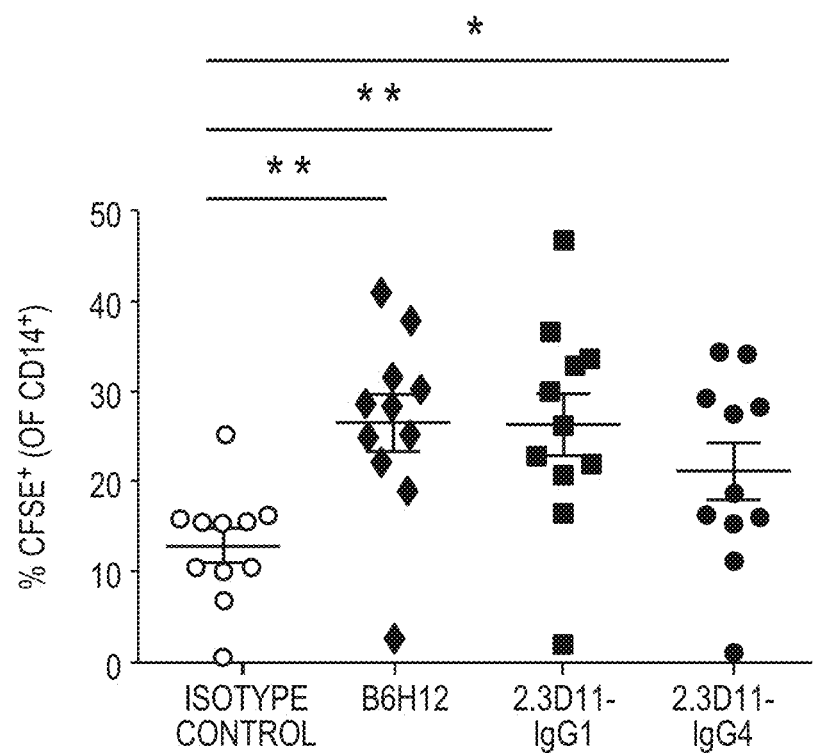
FIG. 13 is a chart showing the percent of CD14+ cells that were CFSE+ in a phagocytosis assay of tumor cells. Primary human monocytes were differentiated in media containing 100 ng/mL recombinant human macrophage colony-stimulating factor (M-CSF) for 7 days. Frozen bone marrow samples from AML patients were thawed, labelled with CFSE and cultured with differentiated macrophages for 2 hours at a target-to-effector ratio of 1:1, in the presence of the indicated antibodies. Phagocytosis was quantitated as described in Example 4. Results from three independent experiments are pooled. Each datapoint shown is an individual donor. * p≤0.05; ** p≤0.01 as measured by an upaired Student's t-Test.

Primary human monocytes were differentiated in 100 ng/mL recombinant human macrophage colony-stimulating factor (M-CSF) for 7 days. Frozen bone marrow samples from AML patients or healthy donors were thawed, labelled with CFSE and cultured with differentiated macrophages for 2 hours at a target-to-effector ratio of 1:1, in the presence of either 10 or 5 μg/mL of the indicated antibodies. Phagocytosis was quantitated as described above. The results are summarized in FIG. 13, which demonstrate that both the 2.3D11 IgG1 and 2.3D11 IgG4 anti-CD47 antibodies stimulate phagocytosis of bone marrow cells from AML patients.

IV—Burkitt's Lymphoma Raji Xenograft Model

SCID-Beige mice were injected subcutaneously with $1\times10^7$ Raji B tumor cells in 50% Matrigel and treatment was started when tumor reached 100 mm$^3$. Isotype control (polyclonal human IgG), 2.3D11 IgG4, 2.3D11 IgG4mt and 2.3D11IgG1 antibodies were injected intraperitoneally (i.p.) with 200 μg of antibody three times per week for 3 weeks. Body weight and tumor volume were measured twice per week.

Figure 14:
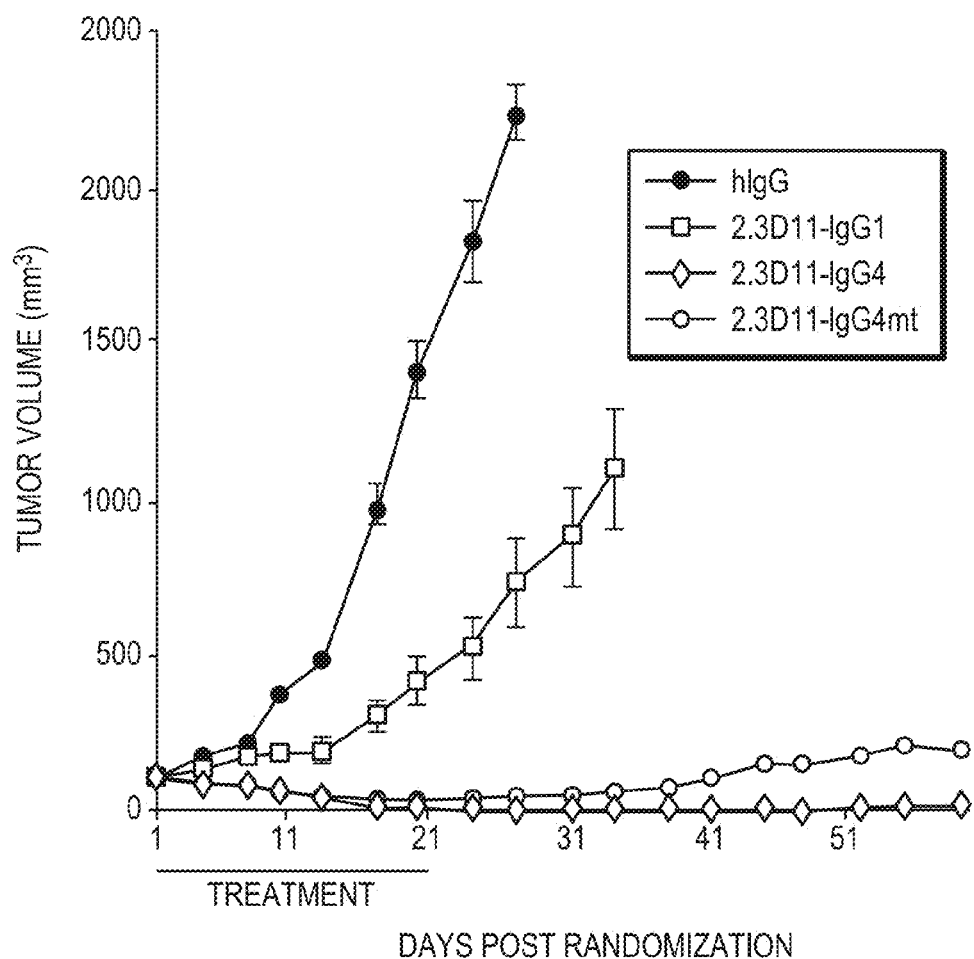
FIG. 14 is a graph showing tumor volume in the Raji lymphoma xenograft model after treatment with the anti-CD47 antibodies 2.3D11 IgG1, 2.3D11 IgG4, or 2.3D11 IgG4mt. SCID-Beige mice were implanted subcutaneously with Raji tumor cells and randomized when the tumors reached ~100 mm$^3$ to receive the indicated antibodies at 200 µg/mouse t.i.w. for 3 weeks. Closed circles indicate human polyclonal IgG, open circles indicate 2.3D11 IgG4mt, open diamonds indicate 2.3D11 IgG4, and open squares indicate 2.3D11 IgG1. In the 2.3D11 IgG4mt arm, 2 tumors reached 2000 mm$^3$ at day 38 and the mice were terminated, so average tumor volumes were not reported after this timepoint.

As shown in FIG. 14, the 2.3D11 IgG1, 2.3D11 IgG4 and 2.3D11 IgG4mt anti-CD47 antibodies demonstrated antitumor activity in this xenograft model, but the 2.3D11

Example 5—Antibody 2.3D11 and Anti-CD38 Antibody Act Synergistically to Enhance Macrophage Phagocytosis of Multiple Myeloma Cells This example shows that a 2.3D11 derived antibody acts synergistically with an anti-CD38 opsonizing antibody.

Primary human monocytes were differentiated in 100 ng/mL recombinant human macrophage colony-stimulating factor (M-CSF) for 7 days. A primary multiple myeloma bone marrow sample was CFSE labeled and co-cultured with differentiated human macrophages at a ratio of 2:1, in the presence of 10 µg/mL of antibody 2.3D11 IgG4, an anti-human CD38-hIgG1 antibody (MAB1135, G&P Biosciences), or both (single-agent conditions were supplemented with 10 µg/mL of isotype control).

Figure 15:
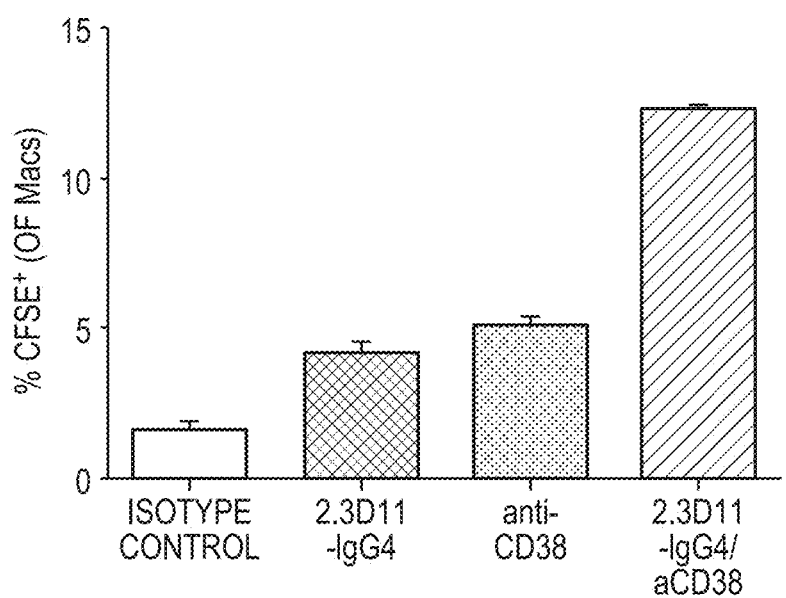
FIG. 15 is a bar chart showing the percent of CD14+ cells that were CFSE+ in a phagocytosis assay of multiple myeloma cells. A primary multiple myeloma bone marrow sample was CFSE labelled and co-cultured with differentiated human macrophages at a ratio of 2:1, in the presence of 10 μg/mL isotype control, 10 μg/mL of 2.3D11, anti-human CD38-hIgG1, or both. Note that single-agent conditions were supplemented with 10 μg/mL of isotype control.

Phagocytosis was assessed by flow cytometry and reported as percent of macrophages that are CFSE-positive. The results are summarized in FIG. 15, which shows that the combination of an anti-CD47 antibody with an anti-CD38 antibody synergistically enhances phagocytosis of multiple myeloma cells as compared to either antibody alone.

In summary, the results presented herein demonstrate that the anti-CD47 antibody 2.3D11 induces robust tumor cell phagocytosis and tumor clearance both alone and in combination with opsonizing antibodies in preclinical models of multiple myeloma.

Example 6—Antibody 2.3D11 and an Anti-CD38 Antibody Act Synergistically to Reduce Tumor Burden in Murine Xenograft Model of Multiple Myeloma This example describes the synergistic properties that can be observed when a 2.3D11 derived antibody is combined with an anti-CD38 opsonizing antibody in a murine model of multiple myeloma.

Figure 16:
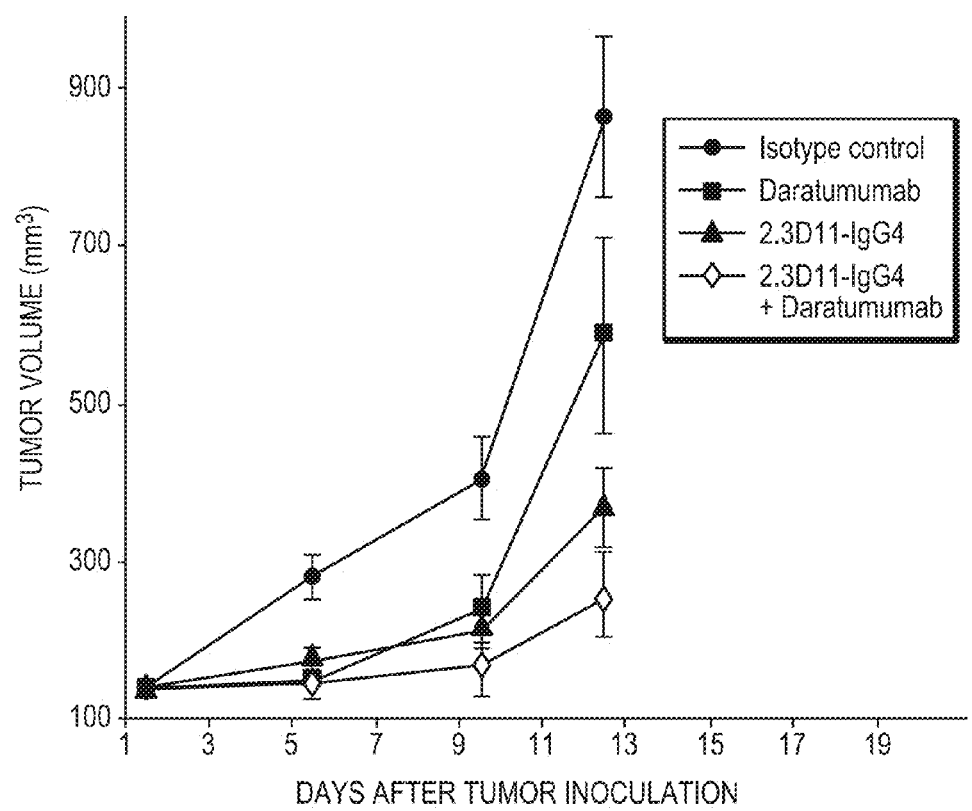
FIG. 16 is a graph showing the decrease in tumor volume in mice treated with 2.3D11 IgG4 either alone or in combination with Daratumumab. CB.17 SCID mice were implanted with H929 tumor cells. When tumors reached an average size of 100-150 $mm^3$, animals were randomized to control or treatment arms. Filled circles indicate isotype control, filled squares indicate Daratumumab administered as a single dose at 10 μg/mouse, filled triangles indicate 2.3D11 IgG4 administered three times per week for 3 weeks at 30 μg/mouse, and open diamonds indicate a combination of 2.3D11 IgG4 and Daratumumab at the monotherapy doses.

8-12 week old CB.17 SCID female mice (Charles River) were injected subcutaneously with $1 \times 10^7$ H929 tumor cells in 50% Matrigel in the right flank. Cell injection volume was 0.1 mL/mouse. When tumors reached an average size of 100-150 mm$^3$, animals were randomized to control or treatment. Treatment groups included 2.3D11 IgG4 at 30 µg/mouse (injected intraperitoneally (i.p.) three times per week for 3 weeks), daratumumab at 10 µg/mouse (injected i.p. at a single dose), and a combination of the two antibodies. Tumor volumes were measured twice weekly with a caliper using the formula (length*width2*0.52). The results are show in FIG. 16 and demonstrate that anti-tumor activity of the combination of 2.3D11 IgG4 and daratumumab is greater than either single agent alone.

Example 7—Antibody 2.3D11 Enhances Phagocytosis of Chronic Lymphocytic Leukemia (CLL) Cells This example describes enhanced phagocytosis of chronic lymphocytic leukemia (CLL) cells mediated by a 2.3D11 derived antibody.

Primary human monocytes were differentiated in 100 ng/mL recombinant human macrophage colony-stimulating factor (M-CSF) for 7 days. CD19+/CD5+ tumor cells from the peripheral blood of a CLL patient were CFSE labeled and co-cultured with differentiated human macrophages at a ratio of 2:1 for two hours, in the presence of antibody 2.3D11 IgG4, or isotype control (anti-DNP antibody with a hIgG4 constant region). Phagocytosis was assessed by flow cytometry, as described above, and reported as percent of CD14+macrophages that are CFSE-positive.

Figure 17:
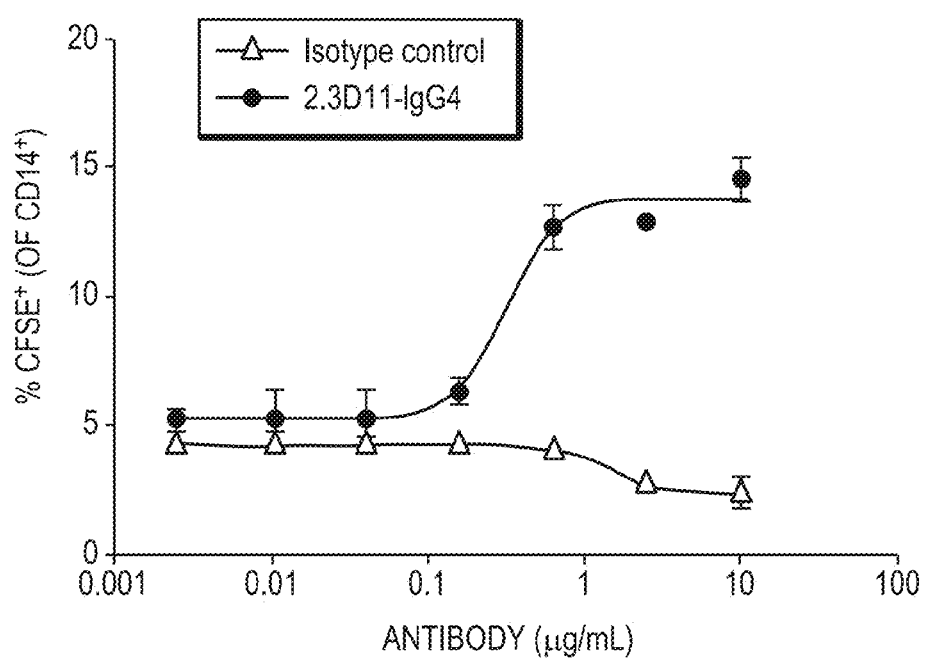
FIG. 17 is a graph showing the percent of CD14+ cells that were CFSE+ in a phagocytosis assay of chronic lymphocytic leukemia (CLL) cells. $CD19^+/CD5^+$ tumor cells from the peripheral blood of a CLL patient were CFSE labelled and co-cultured with differentiated human macrophages at a ratio of 2:1, in the presence of different concentrations of 2.3D11 IgG4 (circles) and isotype control (triangles).
Figure 14:
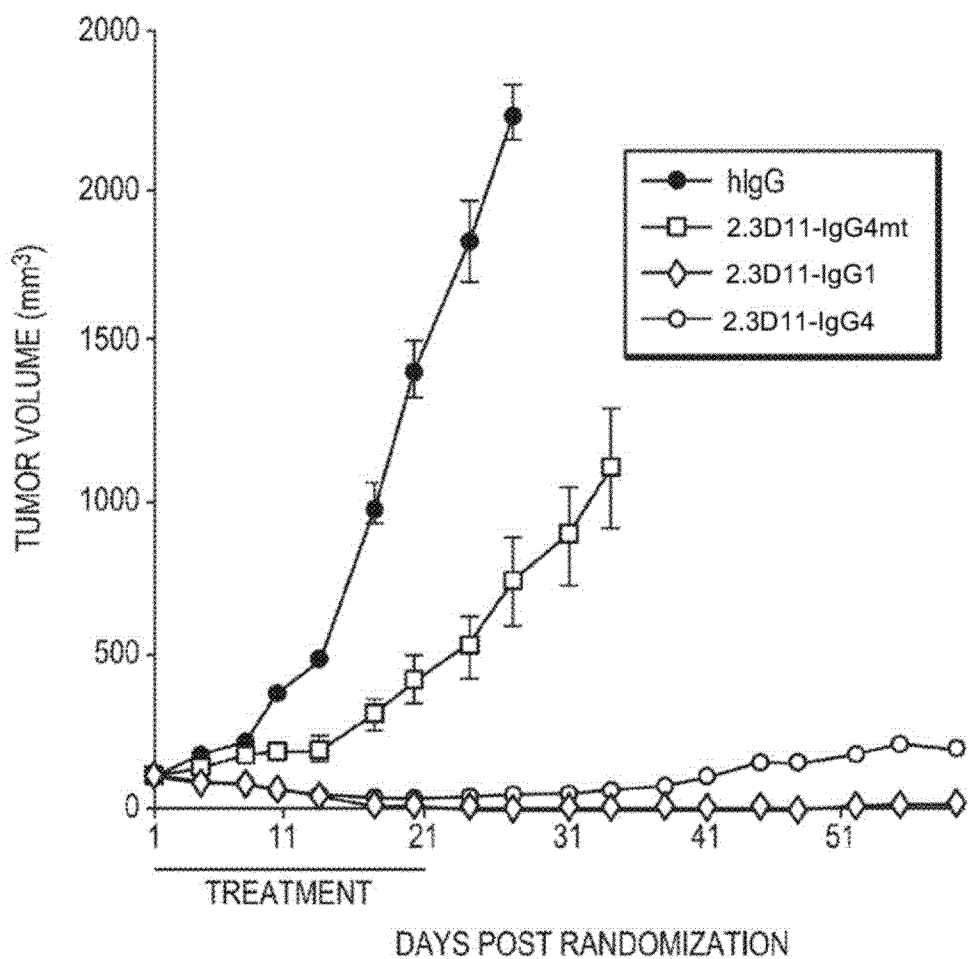

The results are summarized in FIG. 17, which demonstrate the ability of 2.3D11 IgG4 to significantly boost the phagocytosis of primary CLL cells by macrophages in vitro. These data suggest that different stages of CLL may respond to 2.3D11 IgG4 treatment.

INCORPORATION BY REFERENCE

The entire disclosure of each of the patent documents and scientific articles cited herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

---

What is claimed is:

1. An isolated monoclonal antibody that specifically binds human CD47, or antigen binding fragment thereof, wherein the monoclonal antibody or antigen binding fragment thereof comprises:
 a heavy chain complementarity determining region 1 (HC CDR1) comprising the amino acid sequence set forth in SEQ ID NO: 7;
 a heavy chain complementarity determining region 2 (HC CDR2) comprising the amino acid sequence set forth in SEQ ID NO: 8;
 a heavy chain complementarity determining region 3 (HC CDR3) comprising the amino acid sequence set forth in SEQ ID NO: 9;
 a light chain complementarity determining region 1 (LC CDR1) comprising the amino acid sequence set forth in SEQ ID NO: 10;
 a light chain complementarity determining region 2 (LC CDR2) comprising the amino acid sequence set forth in SEQ ID NO: 11; and
 a light chain complementarity determining region 3 (LC CDR3) comprising the amino acid sequence set forth in SEQ ID NO: 12.

2. The isolated monoclonal antibody or antigen-binding fragment of claim 1, wherein the antibody or antigen-binding fragment inhibits the interaction between human CD47 and SIRPα.

3. The isolated monoclonal antibody or antigen-binding fragment of claim 1, wherein the antibody or antigen-binding fragment does not cause significant, or detectable, hemagglutination of human erythrocytes relative to a reference monoclonal antibody that specifically binds human CD47 and causes significant, or detectable, hemagglutination of human erythrocytes, or antigen binding fragment thereof.

4. The isolated monoclonal antibody or antigen-binding fragment of claim 1, wherein the antibody is a human antibody.

5. The isolated monoclonal antibody or antigen-binding fragment of claim 1, wherein the antibody comprises a wild type human IgG1 or wild type human IgG4 heavy chain constant region.

6. The isolated monoclonal antibody or antigen-binding fragment of claim 1, wherein the antibody comprises a mutant IgG1 heavy chain constant region.

7. The isolated monoclonal antibody or antigen-binding fragment of claim 6, wherein the mutant IgG1 heavy chain constant region comprises a substitution at Glu233, Leu234, Leu235, Asn297, or a combination thereof, numbering according to EU numbering.

8. The isolated monoclonal antibody or antigen-binding fragment of claim 6, wherein the mutant IgG1 heavy chain constant region comprises an E233P substitution, an L234A or L234E substitution, an L235A substitution, an N297A substitution, or a combination thereof, numbering according to EU numbering.

9. The isolated monoclonal antibody or antigen-binding fragment of claim 1, wherein the antibody comprises a wild type human IgG4 heavy chain constant region.

10. The isolated monoclonal antibody or antigen-binding fragment of claim 1, wherein the antibody comprises a mutant IgG4 heavy chain constant region.

11. The isolated monoclonal antibody or antigen-binding fragment of claim 10, wherein the mutant IgG4 heavy chain constant region comprises a substitution at Ser228, Leu235, Asn297, or a combination thereof, numbering according to EU numbering.

12. The isolated monoclonal antibody or antigen-binding fragment of claim 10, wherein the mutant IgG4 heavy chain constant region comprises an S228P substitution, an L235E substitution, an N297A substitution, or a combination thereof, numbering according to EU numbering.

13. The isolated monoclonal antibody or antigen-binding fragment of claim 10, wherein the mutant IgG4 heavy chain constant region comprises an S228P substitution and an L235E substitution, numbering according to EU numbering.

14. The isolated monoclonal antibody or antigen-binding fragment of claim 5, wherein the antibody comprises a human kappa constant region.

15. An isolated monoclonal antibody that specifically binds human CD47 or an antigen-binding fragment thereof, wherein the monoclonal antibody comprises a heavy chain variable region (VH) comprising the amino acid sequence set forth in SEQ ID NO: 4 and a light chain variable region (VL) comprising the amino acid sequence set forth in SEQ ID NO: 6.

16. The isolated monoclonal antibody or antigen-binding fragment of claim 15, wherein the antibody or antigen-binding fragment inhibits the interaction between human CD47 and SIRPα.

17. The isolated monoclonal antibody or antigen-binding fragment of claim 15, wherein the antibody or antigen-binding fragment does not cause significant, or detectable, hemagglutination of human erythrocytes relative to a reference monoclonal antibody that specifically binds human CD47 and causes significant, or detectable, hemagglutination of human erythrocytes, or antigen binding fragment thereof.

18. The isolated monoclonal antibody or antigen-binding fragment of claim 15, wherein the antibody is a human antibody.

19. The isolated monoclonal antibody or antigen-binding fragment of claim 15, wherein the antibody comprises a wild-type human IgG1 or wild-type human IgG4 heavy chain constant region.

20. The isolated monoclonal antibody or antigen-binding fragment of claim 19, wherein the antibody comprises a human kappa constant region.

21. The isolated monoclonal antibody or antigen-binding fragment of claim 19, wherein the wild-type human IgG4 heavy chain constant region comprises the amino acid sequence set forth in SEQ ID NO: 20.

22. The isolated monoclonal antibody or antigen-binding fragment of claim 20, wherein the human kappa constant region comprises the amino acid sequence set forth in SEQ ID NO: 22.

23. An isolated monoclonal antibody that specifically binds human CD47, wherein the monoclonal antibody comprises: a heavy chain comprising the amino acid sequence set forth in SEQ ID NO: 15, SEQ ID NO: 23, SEQ ID NO: 24, or SEQ ID NO: 25; and a light chain comprising the amino acid sequence set forth in SEQ ID NO: 16 or SEQ ID NO: 26.

24. The isolated monoclonal antibody of claim 23, wherein the antibody inhibits the interaction between human CD47 and SIRPα.

25. The isolated monoclonal antibody of claim 23, wherein the antibody does not cause significant, or detectable, hemagglutination of human erythrocytes relative to a reference monoclonal antibody that specifically binds human CD47 and causes significant, or detectable, hemagglutination of human erythrocytes, or antigen binding fragment thereof.

26. The isolated monoclonal antibody of claim 23, wherein the antibody is a human antibody.

27. An isolated monoclonal antibody that specifically binds human CD47, wherein the monoclonal antibody comprises: a heavy chain comprising the amino acid sequence set forth in SEQ ID NO: 24; and a light chain comprising the amino acid sequence set forth in SEQ ID NO: 26.

28. The isolated monoclonal antibody of claim 27, wherein the antibody inhibits the interaction between human CD47 and SIRPα.

29. The isolated monoclonal antibody of claim 27, wherein the antibody does not cause significant, or detectable, hemagglutination of human erythrocytes relative to a reference monoclonal antibody that specifically binds human CD47 and causes significant, or detectable, hemagglutination of human erythrocytes, or antigen binding fragment thereof.

30. A composition comprising the isolated monoclonal antibody or antigen-binding fragment of claim 1 and a pharmaceutically acceptable carrier or diluent.

\* \* \* \* \*

UNITED STATES PATENT AND TRADEMARK OFFICE
CERTIFICATE OF CORRECTION

PATENT NO. : 9,803,016 B2
APPLICATION NO. : 15/473206
DATED : October 31, 2017
INVENTOR(S) : Frank Grosveld et al.

Page 1 of 1

It is certified that error appears in the above-identified patent and that said Letters Patent is hereby corrected as shown below:

On the Title Page

In item (71), delete "Erasmus University Medical Center, Rotterdam (NL)" and insert --Erasmus University Medical Center, Rotterdam (NL); Surface Oncology, Inc., Cambridge, MA (US)--.

Signed and Sealed this
Fifth Day of December, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

| | |
|---|---|
| PATENT NO. | : 9,803,016 B2 |
| APPLICATION NO. | : 15/473206 |
| DATED | : October 31, 2017 |
| INVENTOR(S) | : Frank Grosveld et al. |

It is certified that error appears in the above-identified patent and that said Letters Patent is hereby corrected as shown below:

In the Drawings

On sheet 18 of 21, in FIG. 14, delete "2.3D11-IgG1", and insert -- 2.3D11-IgG4mt --, therefor.
On sheet 18 of 21, in FIG. 14, delete "2.3D11-IgG4", and insert -- 2.3D11-IgG1 --, therefor.
On sheet 18 of 21, in FIG. 14, delete "2.3D11-IgG4mt", and insert -- 2.3D11-IgG4 --, therefor.
See attached replacement drawing sheet 18 of 21 reflecting the above-mentioned changes.

In the Specification

In Column 10, Line 62, delete "circles", and insert -- squares --, therefor.
In Column 10, Line 63, delete "diamonds", and insert -- circles --, therefor.
In Column 10, Line 63, delete "squares", and insert -- diamonds --, therefor.

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*